(12) United States Patent
Kang

(10) Patent No.: US 11,739,120 B2
(45) Date of Patent: Aug. 29, 2023

(54) WATER SOLUBLE SALTS OF LIPIDATED PEPTIDES AND METHODS FOR PREPARING AND USING THE SAME

(71) Applicant: Bridge Biotherapeutics, Inc., Seongnam-si (KR)

(72) Inventor: Sang Uk Kang, Seongnam-si (KR)

(73) Assignee: Bridge Biotherapeutics, Inc., Seongnam-Si (KR)

( * ) Notice: Subject to any disclaimer, the term of this patent is extended or adjusted under 35 U.S.C. 154(b) by 47 days.

(21) Appl. No.: 16/288,571

(22) Filed: Feb. 28, 2019

(65) Prior Publication Data
US 2019/0263859 A1    Aug. 29, 2019

Related U.S. Application Data

(60) Provisional application No. 62/636,552, filed on Feb. 28, 2018.

(51) Int. Cl.
| | | |
|---|---|---|
| C07K 5/00 | (2006.01) | |
| C07K 5/117 | (2006.01) | |
| C07K 1/02 | (2006.01) | |
| A61K 47/54 | (2017.01) | |
| A61K 38/00 | (2006.01) | |

(52) U.S. Cl.
CPC .......... C07K 5/1024 (2013.01); A61K 47/542 (2017.08); C07K 1/02 (2013.01); *A61K 38/00* (2013.01)

(58) Field of Classification Search
CPC .............................. C07K 5/1024; C07K 1/02
See application file for complete search history.

(56) References Cited

U.S. PATENT DOCUMENTS

| | | | |
|---|---|---|---|
| 5,068,242 A | 11/1991 | Nickel et al. | |
| 6,069,254 A | 5/2000 | Costanzo et al. | |
| 6,114,361 A | 9/2000 | Robinson et al. | |
| 9,227,997 B2 | 1/2016 | Park et al. | |
| 2003/0022938 A1 | 1/2003 | Burstein et al. | |
| 2013/0172231 A1 | 7/2013 | Park et al. | |
| 2013/0237484 A1 | 9/2013 | Chung et al. | |
| 2017/0008924 A1* | 1/2017 | Lee .......................... A61P 1/00 |

FOREIGN PATENT DOCUMENTS

| | | |
|---|---|---|
| KR | 101151878 B1 | 5/2012 |
| KR | 20120048864 A | 5/2012 |
| KR | 20130038426 A | 4/2013 |
| KR | 20130075934 A | 7/2013 |
| WO | 96/13507 A1 | 5/1996 |
| WO | 2006113942 A2 | 10/2006 |
| WO | 2008060552 A2 | 5/2008 |
| WO | 2010059922 A1 | 5/2010 |
| WO | 2013190497 A2 | 12/2013 |

OTHER PUBLICATIONS

Saal et al., European Journal of Pharmaceutical Sciences, 2013, 49, 614-623. (Year: 2013).*
Bastin et al., Organic Process Research & Development 2000, 4, 427-435. (Year: 2000).*
Yu, M., et al., "Interleukin-6 cytokine family member oncostatin M is a hair-follicle-expressed factor with hair growth inhibitory properties", Experimental Dermatology, vol. 17, pp. 12-19 (2007).
Zhao, H., et al., "Isoliquiritigenin, a flavonoid from licorice, blocks M2 macrophage polarization in colitis-associated tumorigenesis through downregulating PGE2 and IL-6", Toxicology and Applied Pharmacology, vol. 279, pp. 311-321 (2014).
Akira, S. , et al., "Biology of multifunctional cytokines: IL 6 and related molecules (IL 1 and TNF)", The FASEB Journal, vol. 4, pp. 2860-2867 (1990).
Ardeljan, D. , et al., "Aging is not a disease: Distinguishing age-related macular degeneration from aging", Progress in Retinal and Eye Research, vol. 37, pp. 68-89 (2013).
Barlas, S. , "Medicare Part B Drug Reimbursement Program Distresses Pharmacy Players", P&T, 41(6), (2016).
Beck, P.L. , et al., "Transforming Growth Factor-b Mediates Intestinal Healing and Susceptibility to Injury in Vitro and in Vivo Through Epithelial Cells", American Journal of Pathology, 162(2), pp. 597-608 (2003).
Bennett, J.A. , et al., "Pellino-1 Selectively Regulates Epthelial Cell Responses to Rhinovirus", Journal of Virology, 86 (12), pp. 6595-6604 (2012).
Bertola, A. , et al., "Mouse model of chronic and binge ethanol feeding (the NIAAA model)", Nature Protocols, 8(3), pp. 627-637 (2013).
Brajac, I. , et al., "Human Hair Follicle: An Update on Biology and Perspectives in Hair Growth Disorders Treatment", Hair The Transplant, 4(1), 6 pages (2014).
Butler, M. , et al., "Modulation of dendritic cell phenotype and function in an in vitro model of the intestinal epithelium", European Journal of Immunology, vol. 36, pp. 864-874 (2006).

(Continued)

*Primary Examiner* — Jeanette M Lieb
(74) *Attorney, Agent, or Firm* — Servilla Whitney LLC

(57) ABSTRACT

Provided herein are water soluble salts of Formula I, wherein R¹, A, and M are defined herein. Also provided herein are methods of preparing the salts of Formula I and methods of using the same.

5 Claims, 21 Drawing Sheets

Formula I

(56) References Cited

OTHER PUBLICATIONS

Chen, Q.K., et al., "Characteristics and therapeutic efficacy of sulfasalazine in patients with mildly and moderately active ulcerative colitis", World Journal of Gastroenterology, 11 (16), pp. 2462-2466 (2005).
Choi, Kyung-Chul, et al., "Smad6 negatively regulates interleukin 1-receptor- Toll-like receptor signaling through direct interaction with the adaptor Pellino-1", Nature Immunology, vol. 7, No. 10, pp. 1057-1065 (2006).
Contractor, N., et al., "Cutting Edge: Peyer's Patch Plasmacytoid Dendritic Cells (pDCs) Produce Low Levels of Type I Interferons: Possible Role for IL-10, TGFb, and Prostaglandin E2 in Conditioning a Unique Mucosal pDC Phenotype", The Journal of Immunology, vol. 179, pp. 2690-2694 (2007).
Covic, Lidija, et al., "Activation and inhibition of G protein-coupled receptors by cell-penetrating membrane-tethered peptides", PNAS, vol. 99, No. 2, pp. 643-648 (2002).
Covic, Lidija, et al., "Pepducin-based intervention of thrombin-receptor signaling and systematic platelet activation", Nature Medicine, vol. 8, No. 10, pp. 1161-1165 (2002).
Cui, L., et al., "The anti-inftammation effect of baicalin on experimental colitis through inhibiting TLR4/NF-kB pathway activation", International Immunopharmacology, vol. 23, pp. 294-303 (2014).
D'haens, G., "Risks and Benefits of Biologic Therapy for Inflammatory Bowel Diseases", GUT, vol. 56, pp. 725-732 (2007).
Ghosh, S., et al., "NF-κB and REL Proteins: Evolutionarily Conserved Mediators of Immune Responses", Annu Rev. Immunol., vol. 16, pp. 225-260 (1998).
Gregoriou, S., et al., "Cytokines and other Mediators in Alopecia Areata", Mediators of Inflammation, vol. 2010, Article IDS 928030, 5 pages (2010).
Grivennikov, S.I., et al., "Immunity, Inflammation, and Cancer", Cell, 140(6), pp. 883-899 (Mar. 19, 2010).
Grossman, R.M., et al., "Interleukin 6 is expressed in high levels in psoriatic skin and stimulates proliferation of cultured human keratinocytes", Proc. Natl. Acad. Sci. USA, vol. 86, pp. 6367-6371 (1989).
Gu, S.M., et al., "CCR5 knockout suppresses experiemental autoimmune encephalomyelitis in C57BL/6 mice", Oncotarget, 7(13), pp. 15382-15393 (2016).
Horii, Y., et al., "Involvement of IL-6 in Mesangial Proliferative Glomerulonephritis", The Journal of Immunology, 143 (12), pp. 3949-3955 (1989).
Jones, S.A., "Directing Transition from Innate to Acquired Immunity: Defining a Role for IL-61", The Journal of Immunology, vol. 175, pp. 3463-3468 (2005).
Kabanov, Alexander V., et al., "Lipid modification of proteins and their membrane transport", Protein Engineering, vol. 3, No. 1, pp. 39-42 (1989).
Kawano, M., et al., "Autocrine generation and requirement of BSF-2/IL-6 for human multiple myelomas", Nature, 332 (3), pp. 83-85 (1988).
Kobayashi, M., et al., "Toll-like receptor-dependent production of IL-12p40 causes chronic enterocolitis in myeloid cell-specific Stat3-deficient mice", The Journal of Clinical Investigation, 111 (9), pp. 1297-1308 (2003).
Kwack, M.H., et al., "Dihydrotestosterone-Inducible IL-6 Inhibits Elongation of Human Hair Shafts by Suppressing Matrix Cell Proliferation and Promotes Regression of Hair Follicles in Mice", The Socieity for Investigative Dermatology, vol. 132, pp. 43-49 (2012).
Lee, Youn Sook, et al., "Inhibition of lethal inftammatory responses through the targeting of membrane-associated Toll-like receptor 4 signaling complexes with a Smad6-derived peptide", EMBO Molecular Medicine, 7(5), pp. 577-592 (2015).
Li, Z., et al., "Fatty acid conjugation enhances the activities of antimicrobial peptides", Recent Pat Food Nutr Agric. Apr. 2013; 5(1):52-6.
Maric, I., et al., "Bone Morphogenetic Protein-7 Reduces the Severity of Colon Tissue Damage and Accelerates the Healing of Inflammatory Bowel Disease in Rats", Journal of Cellular Physiology, vol. 196, pp. 258-264 (2003).
Masschelein, Joleen, et al., "A combination of polyunsaturated fatty acid, nonribosomal peptide and polyketide biosynthetic machinery is used to assemble the zeamine antibiotics", Chem. Sci., 2015, 6, pp. 923-929.
McElwee, K.J., et al., "Hair physiology and its disorders", Drug Discovery Today: Disease Mechanisms, 5(2), pp. e163-e171 (2008).
Miranda-Hernandez, S., et al., "Role for MyD88, TLR2 and TLR9 but not TLR1, TLR4 or TLR6 in Experimental Autoimmune Encephalomyelitis", The Journal of Immunology, vol. 187, pp. 1-14 (2011).
Neurath, M.F., et al., "The Many Roads to Inflammatory Bowel Diseases", Immunity, vol. 25, pp. 189-191 (2006).
Papassotiropoulos, A., et al., "Genetics of interleukin 6: implications for Alzheimer's disease", Neurobiology of Aging, vol. 22, pp. 863-871 (2001).
Park, H.Y., et al., "Pellino 1 promotes lymphomagenesis by deregulating BCL6 polyubiquitination", The Journal of Clinical Investigation, 124(11 }, pp. 4976-4988 (2014 ).
Rakoff-Nahoum, S., et al., "Recogniation of Commensal Microftora by Toll-Like Receptors is Required for Intestinal Homeostasis", Cell, vol. 118, pp. 229-241 (2004).
Rimoldi, M., et al., "Intestinal immune homeostasis is regulated by the crosstalk between epithelial cells and dendritic cells", Nature Immunology, 6(5), pp. 507-515 (2005).
Rothwarf, D.M., et al., "IKK-g is an essential regulatory subunit of the IκB kinase complex", Nature, vol. 395, pp. 297-300 (1998).
Sen, R., et al., "Multiple Nuclear Factors Interact with the Immunoglobulin Enhancer Sequences", Cell, vol. 46, pp. 705-716 (1986).
Sun, Haiying, et al., "Design of Small-Molecule Peptidic and Nonpeptidic Smac Mimetics", Accounts of Chemical Research, vol. 41, No. 10, pp. 1264-1277 (2008).
Takeda, K., et al., "Enhanced TH1 Activity and Development of Chronic Enterocolitis in Mice Devoid of Stat3 in Macrophages and Neutrophils", Immunity, vol. 10, pp. 39-49 (1999).
Tarallo, V., et al., "DICER1 Loss and Alu RNA Induce Age-Related Macular Degeneration via the NLRP3 Inflammasome and MyD88", Cell, 149(4), pp. 847-859 (2012).
Travis, M.A., et al., "Loss of integrin avb8 on dendritic cells causes autoimmunity and colitis in mice", Nature, vol. 449, pp. 361-366 (2007).
Voraberger, G., et al., "Cloning of the Human Gene for Intercellular Adhesion Molecule 1 and Analysis of its 5'-Regulatory Region", The Journal of Immunology, 147(8), pp. 2777-2786 (1991).
Waldner, M.J., et al., "Master regulator of intestinal disease: IL-6 in chronic inflammation and cancer development", Seminars In Immunology, vol. 26, pp. 75-79 (2014).
Walsh, G.M., "Anti-IL-4/-13 based therapy in asthma", Expert Opinion on emerging drugs, 20(3), pp. 349-352 (2015).
Xiao, Y., et al., "Peli1 promotes microglia-mediated CNS inflammation by regulating Traf3 degradation", Nature Medicine, 19(5), pp. 595-602 (2013).
Yamaoka, S., et al., "Complementation Cloning of NEMO, a Component of the IκB Kinase Complex Essential for NF-κB Activation", Cell, vol. 143, pp. 1231-1240 (1998).

* cited by examiner

WATER SOLUBLE SALTS OF LIPIDATED PEPTIDES AND METHODS FOR PREPARING AND USING THE SAME

BACKGROUND

In various embodiments, the present invention generally relates to novel water soluble pharmaceutically acceptable salts of lipidated peptides and peptido-mimetics, and methods of preparing and using the same.

Various diseases or disorders are mediated by formation of a Pellino-1 induced inflammatory signal transduction complex such as MyD88 and/or RIP1. As shown in U.S. application Ser. No. 15/205,853, published as US2017/0008924, certain lipidated peptides and peptido-mimetics such as the pyrrolidine carboxamido derivatives were shown to be effective in modulating Pellino-1 induced biological pathways and thus were effective in treating various autoimmune and inflammatory diseases. However, lipidated peptides and peptido-mimetics are mostly insoluble in aqueous media and therefore belong to Class IV drugs according to the Biopharmaceutics Classification System (BCS IV). As the solubility of drug candidates in water is an important consideration in drug development, there is a need to prepare lipidated peptides and peptido-mimetics with improved aqueous solubility.

BRIEF SUMMARY OF THE INVENTION

In various embodiments, the present invention relates to novel water soluble salts of Formula I, e.g., substantially pure compound of Formula I,

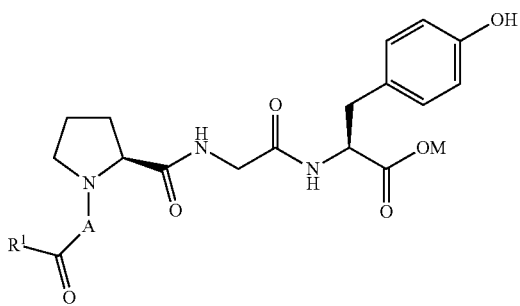

Formula I wherein M, A, R¹ are defined herein. In some embodiments, the present invention also relates to pharmaceutical compositions comprising a compound of Formula I. In some embodiments, the present invention further relates to methods of preparing the compound of Formula I and/or the pharmaceutical composition, and methods of using the same.

Certain embodiments are directed to substantially pure compounds of Formula I. In some embodiments, the substantially pure compound of Formula I is a sodium salt or potassium salt or lithium salt. In some embodiments, the substantially pure compound has a sodium or potassium or lithium content of about 80% to about 125% of the respective theoretical sodium or potassium or lithium content based on Formula I. In some embodiments, the substantially pure compound of Formula I has a purity by weight and/or by HPLC area of at least 90%. In some embodiments, the substantially pure compound is a substantially pure sodium palmitoyl-L-prolyl-L-prolylglycyl-L-tyrosinate (Compound I-1). In some embodiments, the substantially pure Compound I-1 has a sodium content by weight of about 2% to about 5%.

Certain embodiments are directed to pharmaceutical compositions comprising the compound of Formula I (e.g., the substantially pure compound herein). In some embodiments, the compound of Formula I is present in a therapeutically effective amount, for example, for treating a disease or disorder described herein, for example, an inflammatory bowel disease. In some embodiments, the pharmaceutical composition can be formulated for oral, nasal, pulmonary, rectal, buccal, vaginal, ocular, topical, parenteral or transdermal administration. In some embodiments, the pharmaceutical composition can be a solid or liquid. In some embodiments, the pharmaceutical composition can be a capsule or tablet. In any of the embodiments described herein, the pharmaceutical composition can be enteric coated.

In some embodiments, the pharmaceutical composition can comprise a therapeutically effective amount of Compound I-1, for example, for treating a disease or disorder described herein, for example, an inflammatory bowel disease. In some embodiments, Compound I-1 in the pharmaceutical composition is in a form chosen from one or more of amorphous, Form A, Form B, Form C, Form D, Form E, and Form F. In any of the embodiments described herein, Compound I-1 in a pharmaceutical composition can be in an amorphous form.

In some embodiments, the pharmaceutical composition can be storage stable. In some embodiments, the pharmaceutical composition comprises amorphous Compound I-1, wherein upon storage at 40° C. at a relative humidity of 75% or at 25° C. at a relative humidity of 60% for 1 month or more (e.g., 1 month or 6 months), the pharmaceutical composition is substantially free of Compound I-1 in a crystalline form. In some embodiments, the pharmaceutical composition comprises amorphous Compound I-1 and is substantially free of one or more of Form A, Form B, Form C, Form D, Form E, and Form F of Compound I-1.

In some embodiments, the pharmaceutical composition comprises a therapeutically effective amount of any one or more of Compound I-2 to I-10. In some embodiments, the pharmaceutical composition comprises Compound I-2. In some embodiments, Compound I-2 is in a crystalline Form A2. In some embodiments, the active ingredient of the pharmaceutical composition consists essentially of Compound I-1. In some embodiments, the active ingredient of the pharmaceutical composition consists essentially of Compound I-2. In some embodiments, the active ingredient of the pharmaceutical composition consists essentially of Compound I-3.

The pharmaceutical composition can also be characterized by an in vitro dissolution profile, e.g., any of those described herein.

Certain embodiments are also directed to methods of treating various diseases or disorders described herein. In some embodiments, the method is for treating an inflammatory bowel disease in a subject in need thereof, such as ulcerative colitis, Behcet's disease, and/or Crohn's disease. In some embodiments, the method comprises administering to the subject a therapeutically effective amount of any of the substantially pure compounds herein or any of the pharmaceutical compositions described herein. Suitable amounts and routes of administration include any one of those described herein.

In some embodiments, the method is for treating a disease or disorder mediated by formation of a Pellino-1 induced inflammatory signal transduction complex such as MyD88 and/or RIP1 in a subject in need thereof. In some embodiments, the method comprises administering to the subject a therapeutically effective amount of any of the substantially pure compounds herein or any of the pharmaceutical compositions described herein. In some embodiments, the disease or disorder is one or more of multiple sclerosis, psoriasis, sepsis, geographic atrophy, wet age-related macular disease, dry age-related macular disease, diabetic retinopathy, infectious lung diseases, bacterial pneumonia, viral pneumonia, diffuse large B-cell lymphoma, viral infection, autoimmune disease, obesity, blood cancer including lymphoma, and tumors in internal organs. Suitable amounts and routes of administration include any one of those described herein.

In some embodiments, the method is for treating alopecia in a subject in need thereof. In some embodiments, the method comprises administering to the subject a therapeutically effective amount of any of the substantially pure compounds herein or any of the pharmaceutical compositions described herein. Suitable amounts and routes of administration include any one of those described herein.

In some embodiments, the method is for treating geographic atrophy, wet age-related macular disease, dry age-related macular disease, and/or diabetic retinopathy in a subject in need thereof. In some embodiments, the method comprises administering to the subject a therapeutically effective amount of any of the substantially pure compounds herein or any of the pharmaceutical compositions described herein. Suitable amounts and routes of administration include any one of those described herein.

In some embodiments, the present invention also provides a method of inhibiting formation of an inflammatory signal transduction complex MyD88, formation of an inflammatory signal transduction complex mediated by Pellino-1, or formation of an inflammatory signal transduction complex Rip1; suppressing expression of at least one protein selected from the group consisting of G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1; and/or suppressing activity of NF-κB in a cell. In some embodiments, the method comprises contacting the cell with an effective amount of any of the substantially pure compounds herein or any of the pharmaceutical compositions described herein. Suitable amounts and routes of administration include any one of those described herein.

Certain embodiments are also directed to an aqueous composition comprising a compound of Formula I (e.g., Compound I-1 or I-2). In some embodiments, the aqueous composition comprises Compound I-1 or I-2. In some embodiments, the concentration of the compound I-1 or I-2 is at least 50 mg/mL (e.g., at least 100 mg/mL, at least 200 mg/mL) of the composition. In some embodiments, the concentration of the compound I-1 or I-2 is 0.1 mg/mL to 50 mg/mL of the composition. In some embodiments, the lower concentrated composition can be prepared from diluting the higher concentrated composition herein. In some embodiments, the aqueous composition comprises one or more of sodium phosphate, sodium chloride, polysorbate, sucrose, meglumine, Cremophor RH40, Tween 80, HPβCD, and HPMC E3. For example, in some embodiments, the aqueous composition comprises meglumine and Cremophor RH40, wherein the weight ratio of meglumine to Cremophor RH40 is about 1:5 to about 5:1. In some embodiments, the aqueous composition comprises meglumine, e.g., in a concentration of about 2% to about 5% (weight to volume). In some embodiments, the aqueous composition comprises Compound I-1 in a concentration of at least 200 mg/mL and meglumine in a concentration of about 2% to about 5% (weight to volume). In some embodiments, the aqueous composition comprises Compound I-1 (e.g., at a concentration of at least 200 mg/mL) and meglumine (e.g., at a concentration of about 2% to about 5% (weight to volume)) is storage stable at 25° C. For example, in some embodiments, such composition is substantially free of precipitates upon storage at 25° C. for 1 week or 2 weeks. The aqueous composition or a diluted composition therefrom can be included in a pharmaceutical composition and can be used for any of the methods herein.

BRIEF DESCRIPTION OF THE DRAWINGS/FIGURES

FIG. 1A provides an exemplary X-ray powder diffraction (XRPD) spectrum of Compound I-1-Acid in Form 1. FIG. 1B presents a graph showing the thermogravimetric analysis (TGA) and differential scanning calorimetry (DSC) analysis of Compound I-1-Acid in Form 1.

FIG. 2 provides an exemplary XRPD spectrum of Compound I-1-Acid in amorphous form.

FIG. 3 provides an exemplary XRPD spectrum of Compound I-1 in amorphous form.

FIG. 4A provides two exemplary XRPD spectra of Form A of Compound I-1, one for solids obtained from small scale and another for solids obtained from a scale-up. FIG. 4B presents a graph showing the TGA and DSC analysis of Form A of Compound I-1.

FIG. 5 presents a graph showing the TGA and DSC analysis of Form B of Compound I-1.

FIG. 6A provides an exemplary XRPD spectrum of Form C of Compound I-1, overlaid with Form A of Compound I-1. FIG. 6B presents a graph showing the TGA and DSC analysis of Form C of Compound I-1.

FIG. 7 provides an exemplary XRPD spectrum of a solid form identified in a solubility test, Form D of Compound I-1, overlaid with Form A of Compound I-1. FIG. 7 also shows that, upon drying, Form D is converted into Form A.

FIG. 8A provides an exemplary XRPD spectrum of Form E of Compound I-1, overlaid with Forms A and C of Compound I-1. FIG. 8B presents a graph showing the TGA and DSC analysis of Form E of Compound I-1.

FIG. 9A provides an exemplary XRPD spectrum of Form F of Compound I-1, overlaid with Forms A and E of Compound I-1. FIG. 9B presents a graph showing the TGA and DSC analysis of Form F of Compound I-1.

FIG. 10A provides exemplary XRPD spectra of Form A2 of Compound I-2, for solids obtained from small scale or scale-up. FIG. 10B presents a graph showing the TGA and DSC analysis of Form A2 of Compound I-2.

Acid and Ca(OH)$_2$ in the molar ratio of 1:1 in ethanol or IPA, stirring the solution until it becomes transparent and then evaporating the solution at room temperature to obtain the desired form or adding acetonitrile as an antisolvent to the solution at room temperature to obtain the desired form.

Figure 14:
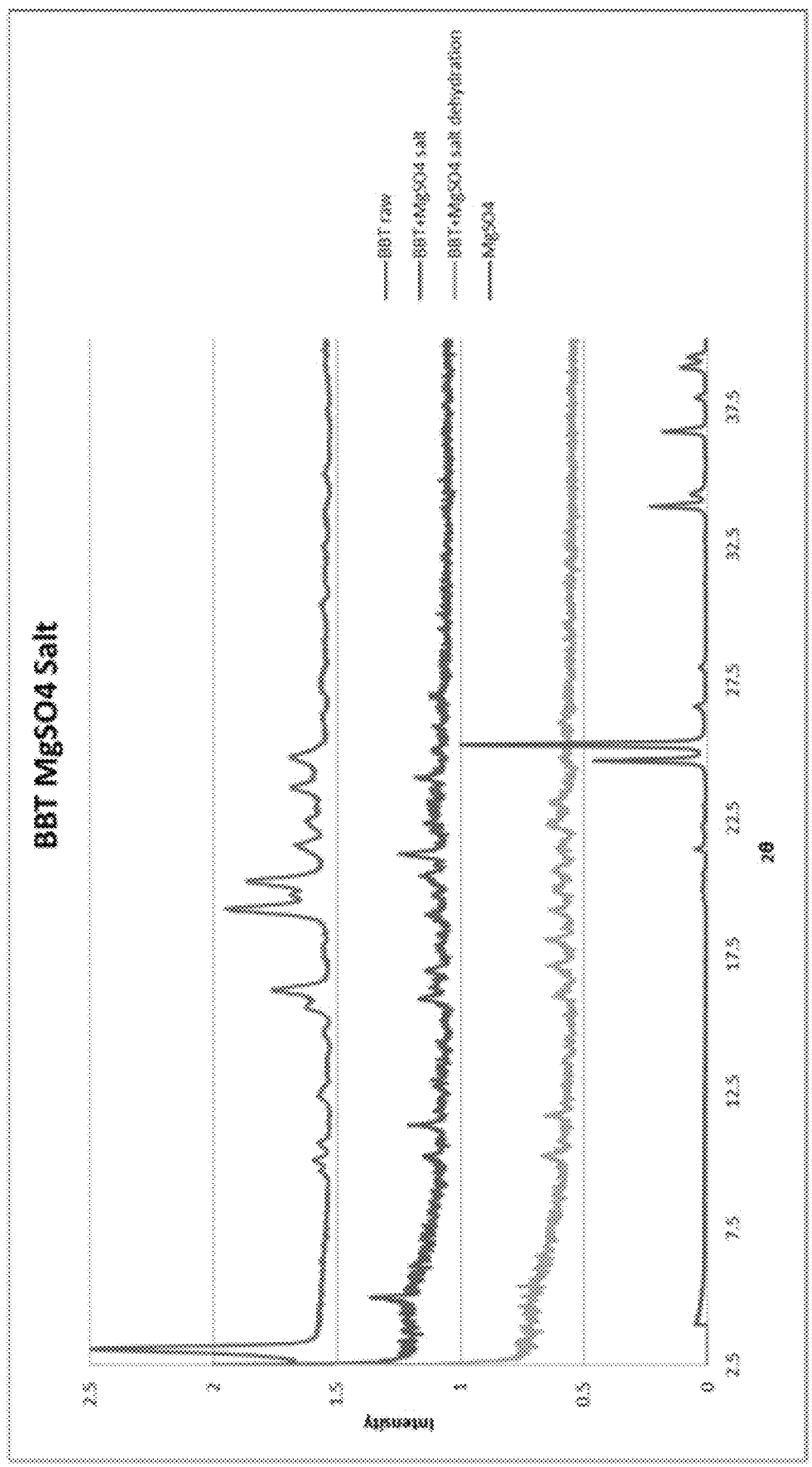

FIG. 14 shows XRPD spectrum of Compound I-1-Acid magnesium salt prepared by taking Compound I-1-Acid and MgSO$_4$ in 1:1 molar ratio, dissolving pH=12 solution and slurring for 1-2 days to obtain the desired product.

Figure 15:
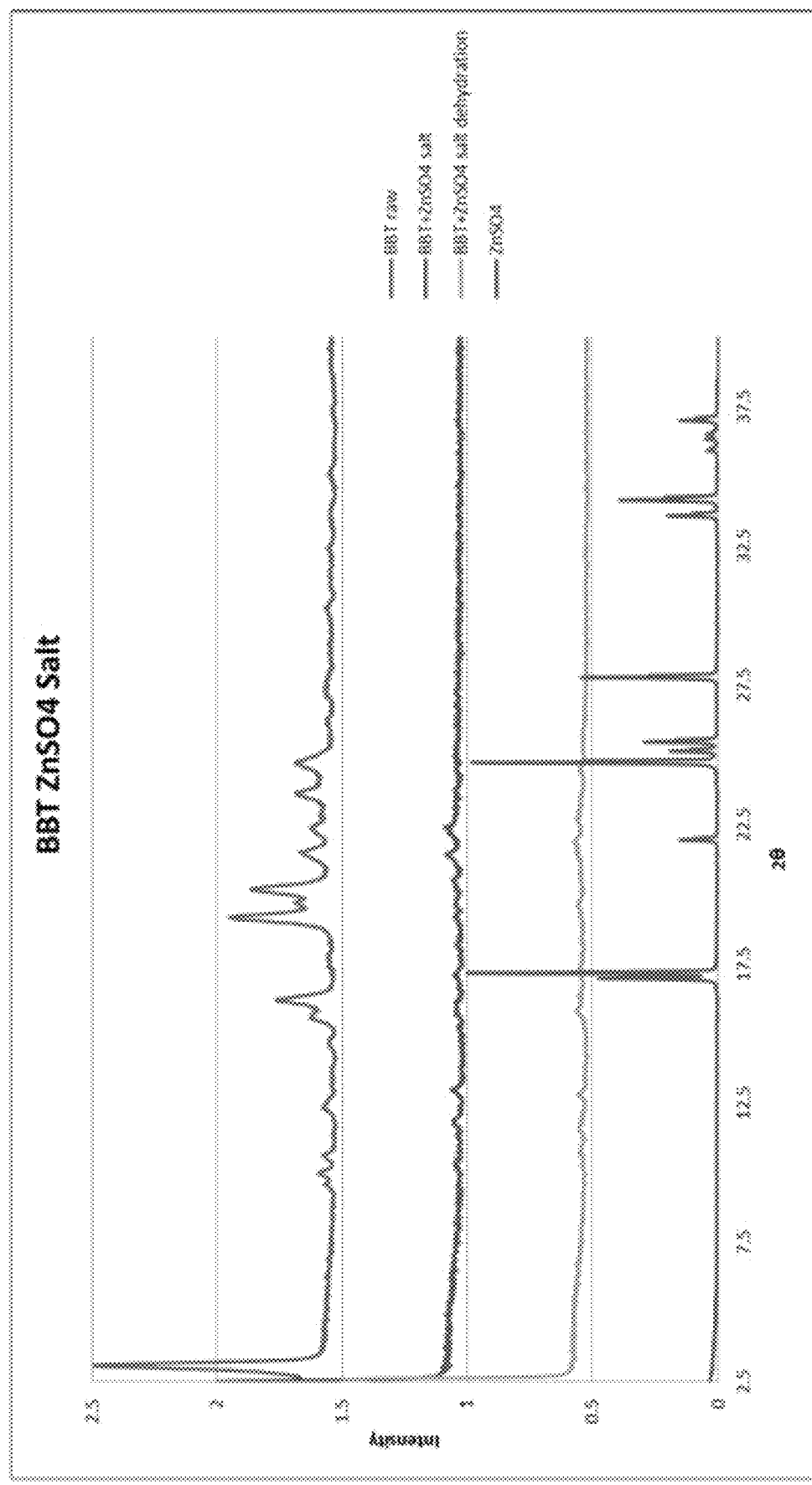

FIG. 15 shows XRPD spectrum of Compound I-1-Acid zinc salt prepared by taking Compound I-1-Acid and ZnSO$_4$ in 1:1 molar ratio, dissolving pH=12 solution and slurring for 1-2 days to obtain the desired product.

DETAILED DESCRIPTION OF THE INVENTION

In various embodiments, the present invention relates to the discovery of water soluble salt of some lipidated peptides and peptido-mimetics. By choosing appropriate salts and additives, aqueous solubility of some lipidated peptides and peptido-mimetics can be dramatically improved, by as much as 50,000 fold or more. Accordingly, in various embodiments, the present invention provides salts of lipidated peptides and peptide-mimetics, which can have improved aqueous solubility, as well as methods for preparing the salts and methods of using the salts.

Salts

In some embodiments, the present invention provides a salt of a compound having Formula I-Acid:

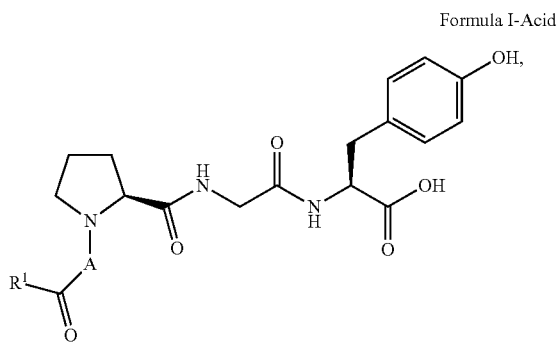

Formula I-Acid an optical isomer thereof, a solvate or hydrate thereof, or a prodrug thereof, wherein A and R$^1$ are as defined herein. In some embodiments, the salt is a Lithium (Li), Sodium (Na), Potassium (K), Strontium (Sr), Magnesium (Mg), Calcium (Ca), Zinc (Zn), Meglumine, Arginine, or Lysine salt. In some embodiments, the salt is an isolated salt that is substantially pure, for example, with a purity by weight of at least 70% (e.g., at least 75%, at least 80%, at least 85%, at least 90%, at least 95%, or at least 97%). In some embodiments, the salt is an isolated salt with a purity by weight of about 70%, about 75%, about 80%, about 85%, about 90%, about 95%, about 97%, about 99%, or any ranges between the specified values. In some embodiments, the salt has an enantiomeric purity, expressed as enantiomeric excess or ee, of about 50% ee or more, e.g., about 60% ee, about 65% ee, about 70% ee, about 75% ee, about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more, and up to 100% ee. In some embodiments, the salt has a diastereomeric purity, expressed as diastereomeric excess or de, of about 50% de or more, e.g., about 60% de, about 65% de, about 70% de, about 75% de, about 80% de, about 85% de, about 90% de, about 91% de, about 92% de, about 93% de, about 94% de, about 95% de, about 96% de, about 97% de, about 98% de, about 99% de, about 99.5% de or more, and up to 100% de. In some embodiments, the salt is substantially free (e.g., less than 5%, less than 2%, less than 1%, or non-detectable) of a salt of a stereoisomer other than the stereoisomer shown in Formula I-Acid. As used herein, a substantially pure compound or salt herein refers to the compound or salt having a purity by weight of at least 60% (e.g., at least 65%, at least 70%, at least 75%, at least 80%, at least 85%, at least 90%, at least 95%, or at least 97%). Unless otherwise obvious from context, for the purpose of calculating the weight percentage of the compound/salt in the substantially pure compound or salt, anything other than the compound or salt, or a solvate or hydrate form thereof, is regarded as an impurity, which includes for example residual solvents, moisture contents, enantiomers, diastereomers, etc. For avoidance of doubt, a composition comprising the substantially pure compound or salt herein and one or more other ingredients should be understood as a composition obtained directly or indirectly from mixing the substantially pure compound or salt herein with the one or more other ingredients, such as water, pharmaceutically acceptable excipients, etc.

In some embodiments, the present invention provides a substantially pure compound having Formula I,

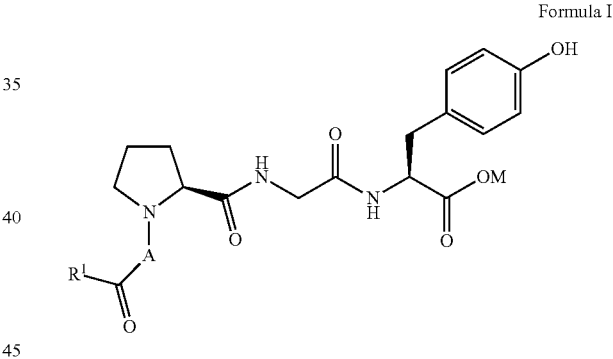

Formula I wherein
M is a monovalent cation, such as an alkali metal cation, e.g., Li, Na, or K,
or M is a multivalent cation, balanced with appropriate counterions, such as SrX, MgX, CaX or ZnX, wherein X is a monovalent anion or a monovalent anion of Formula I-Acid;
A is a bond, or
A represents a monopeptide or dipeptide linker, wherein the monopeptide or dipeptide is comprised of one or two amino acid units, each independently selected from the group consisting of alanine, (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V), wherein the N and C terminals of the monopeptide or dipeptide are linked to R$^1$C(=O) and the pyrrolidine nitrogen atom through amide bonds, respectively; and R¹ is a straight chain or branched chain $C_{1-36}$ alkyl, a straight chain or branched chain $C_{2-36}$ alkenyl, or a straight chain or branched chain $C_{2-36}$ alkynyl. The alkyl, alkenyl, or alkynyl chain can be optionally substituted. In some embodiments, the compound of Formula I can exist in a form of a solvate or hydrate. For example, in some embodiments, the compound of Formula I exists in a form of a pharmaceutically acceptable solvate. In some embodiments, the compound of Formula I is in a hydrate form. In some embodiments, the compound of Formula I is in an anhydrous form.

In some embodiments, M is a monovalent cation. In some specific embodiments, M is Na. In some specific embodiments, M is K. Other monovalent cations are also suitable, for example, those based on an ammonium ion or a cation formed from an organic amine, e.g., meglumine, or an amino acid, such as lysine.

In some embodiments, M can also be a multivalent cation, balanced with appropriate counterions. In some embodiments, M is a divalent cation balanced with one monovalent anion. For example, M can be SrX, MgX, CaX or ZnX, wherein X is a monovalent anion, which can be a pharmaceutically acceptable monovalent anion. In some embodiments, X is

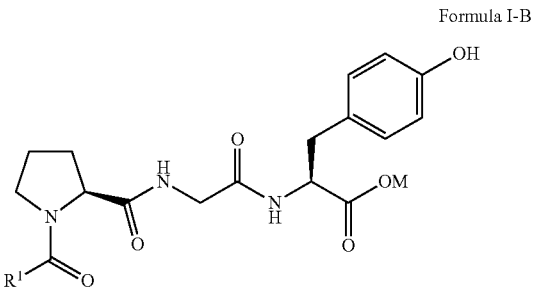

wherein R¹ and A are defined herein. In some embodiments, X is such that two identical carboxylates are attached to the divalent cation in Formula I. For example, in some embodiments, the salt of Formula I has a Formula I-A:

(Formula I-A)

wherein M² is Sr, Mg, Ca, or Zn, R¹ and A are defined herein.

In some embodiments, A is a bond and the compound is characterized as having a Formula I-B:

Formula I-B wherein M and R¹ are defined herein.

In some embodiments, A is a monopeptide (i.e., single amino acid) or dipeptide linker. As used herein, monopeptide linker can also be expressed as an amino acid linker. For example, in some embodiments, A can be an L-amino acid linker. As used herein, a monopeptide or dipeptide linker is linked to R¹C(=O) and the pyrrolidine nitrogen atom of Formula I through the monopeptide or dipeptide's N and C terminals by amide bonds, respectively. For example, in some embodiments, A can be an L-proline linker, and the compound of Formula I has a Formula I-C:

Formula I-C wherein M and R¹ are defined herein. In some embodiments, A can be a glycine linker. In some embodiments, A can be an L-phenylalanine linker. In some embodiments, A can be an L-alanine linker. In some embodiments, A can be an L-valine linker. Other suitable groups for A are described herein.

Various R¹ groups are suitable. In some embodiments, R¹ is a straight chain or branched chain $C_{1-36}$ alkyl, for example, a straight chain $C_5$, $C_7$, $C_9$, $C_{15}$, or $C_{17}$ alkyl. In some embodiments, R¹ is a straight chain or branched chain $C_{2-36}$ alkenyl, for example, containing 1, 2, 3, 4, 5, or 6 double bonds. For example, $R^1$ can be a straight chain $C_{17}$ alkenyl with 1 double bond. In any of the embodiments herein, the alkyl, alkenyl, or alkynyl can be unsubstituted. However, in some embodiments, the alkyl alkenyl, or alkynyl can also be optionally substituted.

In some embodiments, the substantially pure compound having Formula I (e.g., Formula I-B or I-C) is characterized by a purity by weight and/or by HPLC area of least 70% (e.g., at least 75%, at least 80%, at least 85%, at least 90%, at least 95%, or at least 97%). In some embodiments, the substantially pure compound having Formula I (e.g., Formula I-B or I-C) is characterized by a purity by weight and/or by HPLC area of about 70%, about 75%, about 80%, about 85%, about 90%, about 95%, about 97%, about 99%, or any ranges between the specified values. In some embodiments, the substantially pure compound having Formula I (e.g., Formula I-B or I-C) has an enantiomeric purity of about 50% ee or more, e.g., about 60% ee, about 65% ee, about 70% ee, about 75% ee, about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more and up to 100% ee. In some embodiments, the substantially pure compound having Formula I (e.g., Formula I-B or I-C) has a diastereomeric purity of about 50% de or more, e.g., about 60% de, about 65% de, about 70% de, about 75% de, 80% de or more, e.g., about 85% de, about 90% de, about 91% de, about 92% de, about 93% de, about 94% de, about 95% de, about 96% de, about 97% de, about 98% de, about 99% de, about 99.5% de or more, and up to 100%. In some embodiments, the salt is substantially free (e.g., less than 5%, less than 2%, less than 1%, or non-detectable) of a stereoisomer other than the stereoisomer shown in Formula I (e.g., Formula I-B or I-C). Methods for determining enantiomeric or diastereomeric purities are known in the art, for example, by HPLC.

In some embodiments, the substantially pure compound having Formula I (e.g., Formula I-B or I-C) is characterized by a content of M substantially similar to theoretical content based on Formula I. For example, in some embodiments, wherein M is Na or K, and the substantially pure compound has a sodium or potassium content of about 60% to about 130% (e.g., about 80% to about 125%) of the respective theoretical sodium or potassium content based on Formula I. Methods for determining Na or K content are known in the art, for example, using Ion Chromatography.

Compound I-1

Certain embodiments of the present invention are directed to specific compounds of Formula I, for example, Compounds I-1 to I-10 as shown below.

Compound I-1

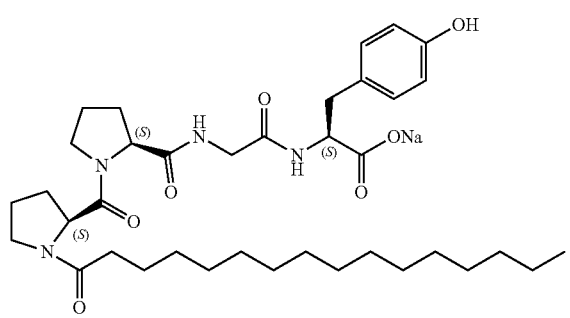

Compound I-2

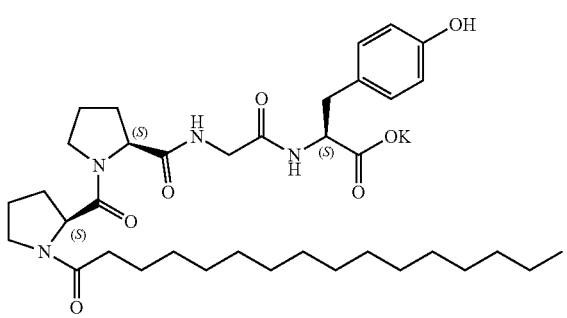

Compound I-3

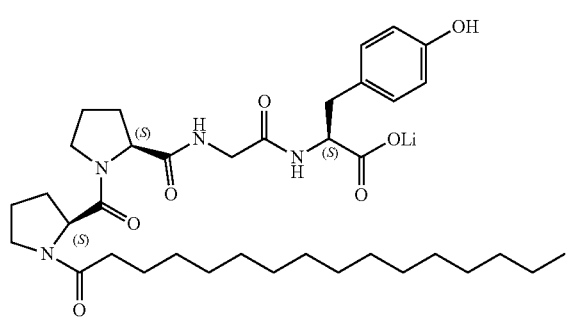

Compound I-4

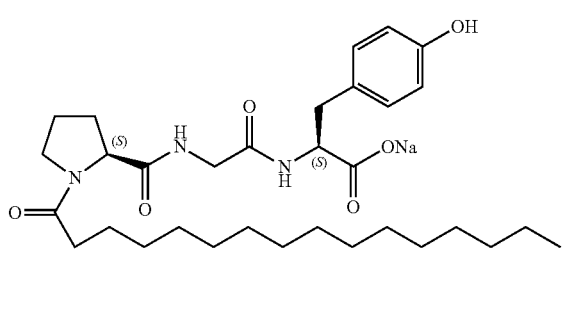

Compound I-5

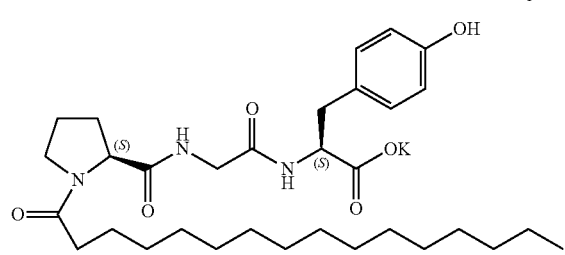

Compound I-6

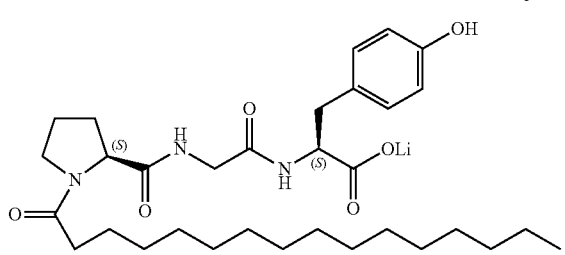

-continued

Compound I-7

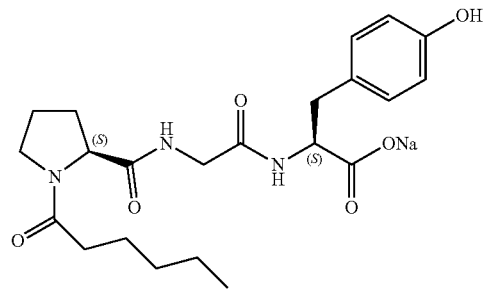

Compound I-8

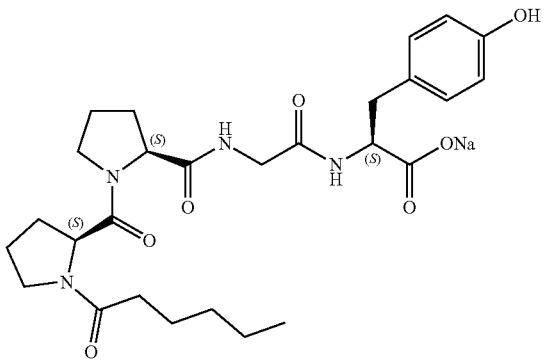

Compound I-9

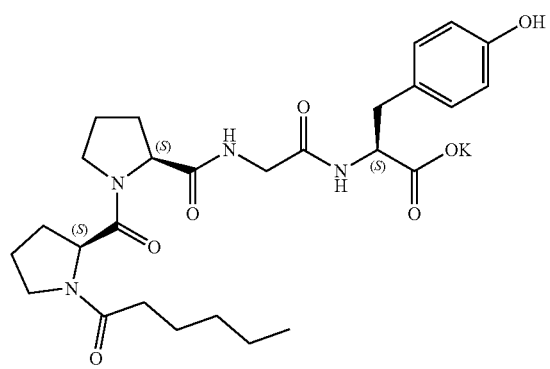

Compound I-10

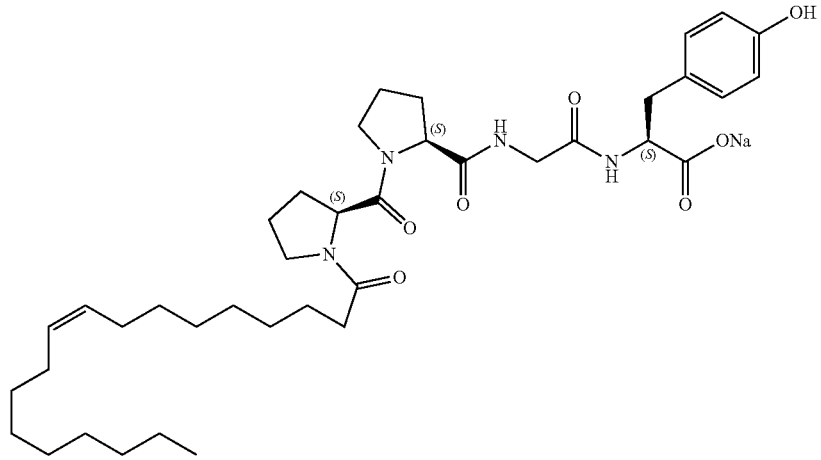

In some specific embodiments, the present invention is directed to Compound I-1. In some embodiments, the present invention provides a substantially pure Compound I-1. In some embodiments, the substantially pure Compound I-1 has a purity by weight and/or by HPLC area of at least 60% (e.g., at least 65%, at least 70%, at least 75%, at least 80%, at least 85%, at least 90%, at least 95%, or at least 97%). In some embodiments, the substantially pure Compound I-1 has a purity by weight and/or by HPLC area of about 60%, about 65%, about 70%, about 75%, about 80%, about 85%, about 90%, about 95%, about 97%, about 99%, or any ranges between the specified values. The enantiomeric purity of the substantially pure Compound I-1 is typically high, for example, with an enantiomeric excess (ee) of about 50%, about 60%, about 70%, about 80%, about 90%, about 95%, about 98%, about 99%, about 99.5% or more, and up to 100%. The diastereomeric purity of the substantially pure compound I-1 typically is also high, for example, with a diastereomeric excess (de) of about 50%, about 60%, about 70%, about 80%, about 90%, about 95%, about 98%, about 99%, about 99.5% or more, and up to 100%. In any of the embodiments herein, the substantially pure Compound I-1 is substantially free (e.g., less than 5%, less than 2%, less than 1%, or non-detectable) of a stereoisomer other than the stereoisomer shown as Compound I-1. In any of the embodiments herein, the substantially pure Compound I-1 can also be characterized as having a purity by weight of at least 90% (e.g., at least 95%, at least 98%), a purity by HPLC area of at least 90% (e.g., at least 95%, at least 98%), or both.

Figure 1A:
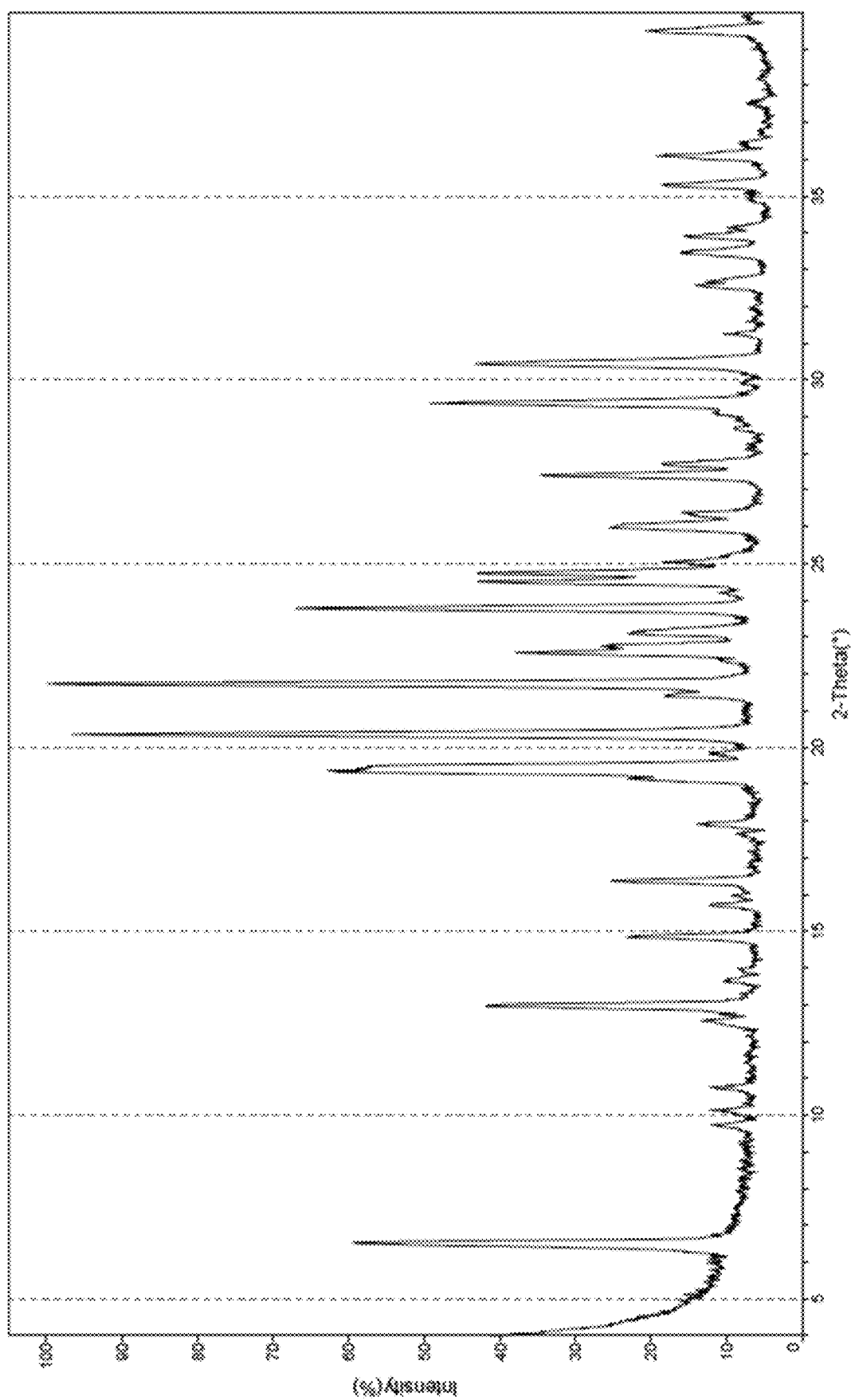
Figure 1B:
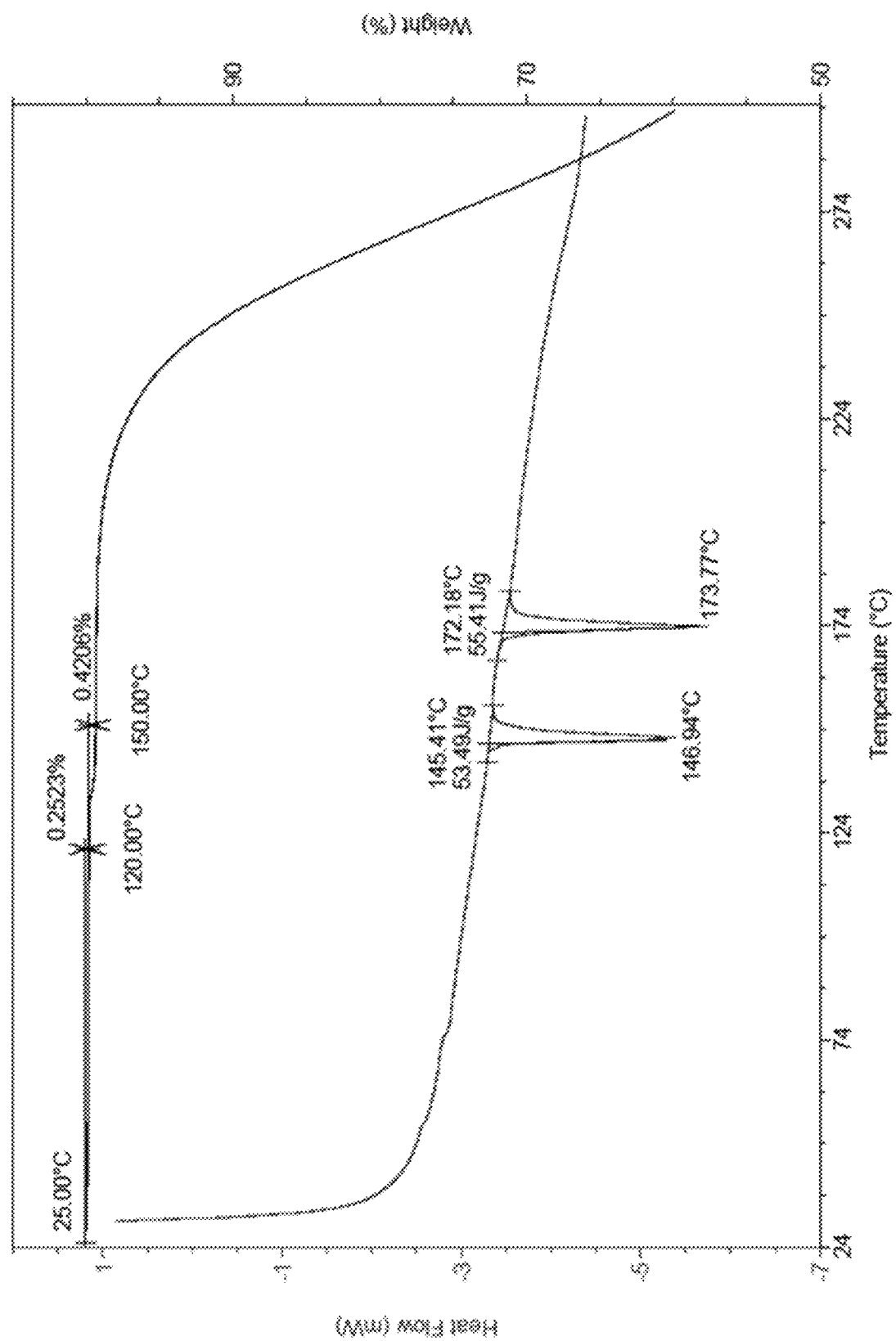

The substantially pure Compound I-1 can be prepared from a substantially pure Compound I-1-Acid. Compound I-1-Acid can be prepared in high purity according to the process disclosed herein. Typically, Compound I-1-Acid prepared according to the processes herein has a total impurity of less than 30% (e.g., less than 20%, less than 1%, less than 0.5%, less than 0.2%) as measured by HPLC. In some embodiments, compound I-1-Acid does not contain a single impurity in an amount greater than 5% (e.g., not greater than 4%, not greater than 1%, not greater than 0.5%, not greater than 0.05%) as measured by HPLC. As shown in the Examples section, Compound I-1-Acid can also be prepared as an amorphous form or a crystalline form, e.g., Form 1. In some embodiments, the substantially pure Compound I-1 is prepared from amorphous Compound I-1-Acid. In some embodiments, the substantially pure Compound I-1 is prepared from Form 1 of Compound I-1-Acid. In some embodiments, the substantially pure compound I-1 is prepared from amorphous Compound I-1-Acid, Form 1 of Compound I-1-Acid, or a combination thereof. As used herein, Form 1 refers to a crystalline form of Compound I-1-Acid which can be characterized by an XRPD pattern substantially the same as FIG. 1A or an XRPD spectrum having the major peaks of FIG. 1A. In some embodiments, Form 1 can be further characterized by a DSC profile substantially the same as shown in FIG. 1B, a TGA profile substantially the same as shown in FIG. 1B, or a combination thereof. Major peaks of an XRPD spectrum as used herein refer to peaks having diffraction angles between 4-40 degrees (2 theta) and a relative intensity of 10% or above. In some embodiments, major peaks of an XRPD spectrum can refer to peaks with a relative intensity of 20% or above, 30% or above, 40% or above, 50% or above, 60% or above, 70% or above, 80% or above, or 90% or above.

The substantially pure Compound I-1 herein typically has a sodium content close to the theoretical sodium content calculated based on the formula of Compound I-1. In some embodiments, the substantially pure Compound I-1 is characterized by a molar ratio of sodium to the carboxylate portion of Compound I-1 of about 1:1. In some embodiments, the substantially pure Compound I-1 has a sodium content of about 80% to about 125% of the theoretical sodium content. In some embodiments, the substantially pure Compound I-1 has a sodium content by weight of about 2% to about 5%.

The substantially pure Compound I-1 herein can be free or substantially free of Compound I-1-Acid, and/or can be free or substantially free of other salts of Compound I-1-Acid. In some embodiments, the substantially pure Compound I-1 is substantially free of compound I-1-Acid, for example, with an amount of less than 5% by weight (e.g., less than 3%, less than 1%, less than 0.2%, less than 0.1% or less than 0.05%). In some embodiments, the substantially pure Compound I-1 is free of Compound I-1-Acid, other than an amount that may exist through equilibrium. In some embodiments, the substantially pure Compound I-1 has no detectable amount of Compound I-1-Acid. In some embodiments, the substantially pure Compound I-1 is substantially free of other salts of Compound I-1-Acid, for example, with an amount less than 20% by weight (e.g., less than 10%, less than 1%, less than 0.2%, less than 0.1% or less than 0.05%). In some embodiments, the substantially pure Compound I-1 includes no detectable amount of other salts of Compound I-1-Acid.

Compound I-1 can exist in different solid states, which are useful in formulation and/or manufacturing processes. In some embodiments, the present invention also provides different solid states of Compound I-1. In some embodiments, an amorphous Compound I-1 is provided. In some embodiments, a composition (e.g., a pharmaceutical composition) comprising the amorphous Compound I-1 is provided. In some embodiments, the composition is substantially free (e.g., less than 10%, or not detectable by XRPD) of a crystalline form of Compound I-1. The amorphous Compound I-1 can be hygroscopic. However, as detailed in the Examples section, the amorphous Compound I-1 can be storage stable, for example, at 25° C./60% RH or 40° C./75% RH for 2 weeks or more (e.g., 2 weeks, 1 month, 6 months, or more). In any of the embodiments described herein, Compound I-1 can be amorphous Compound I-1. In any of the embodiments described herein, amorphous Compound I-1 can be characterized by an XRPD spectrum substantially the same as FIG. 3.

Figure 4A:
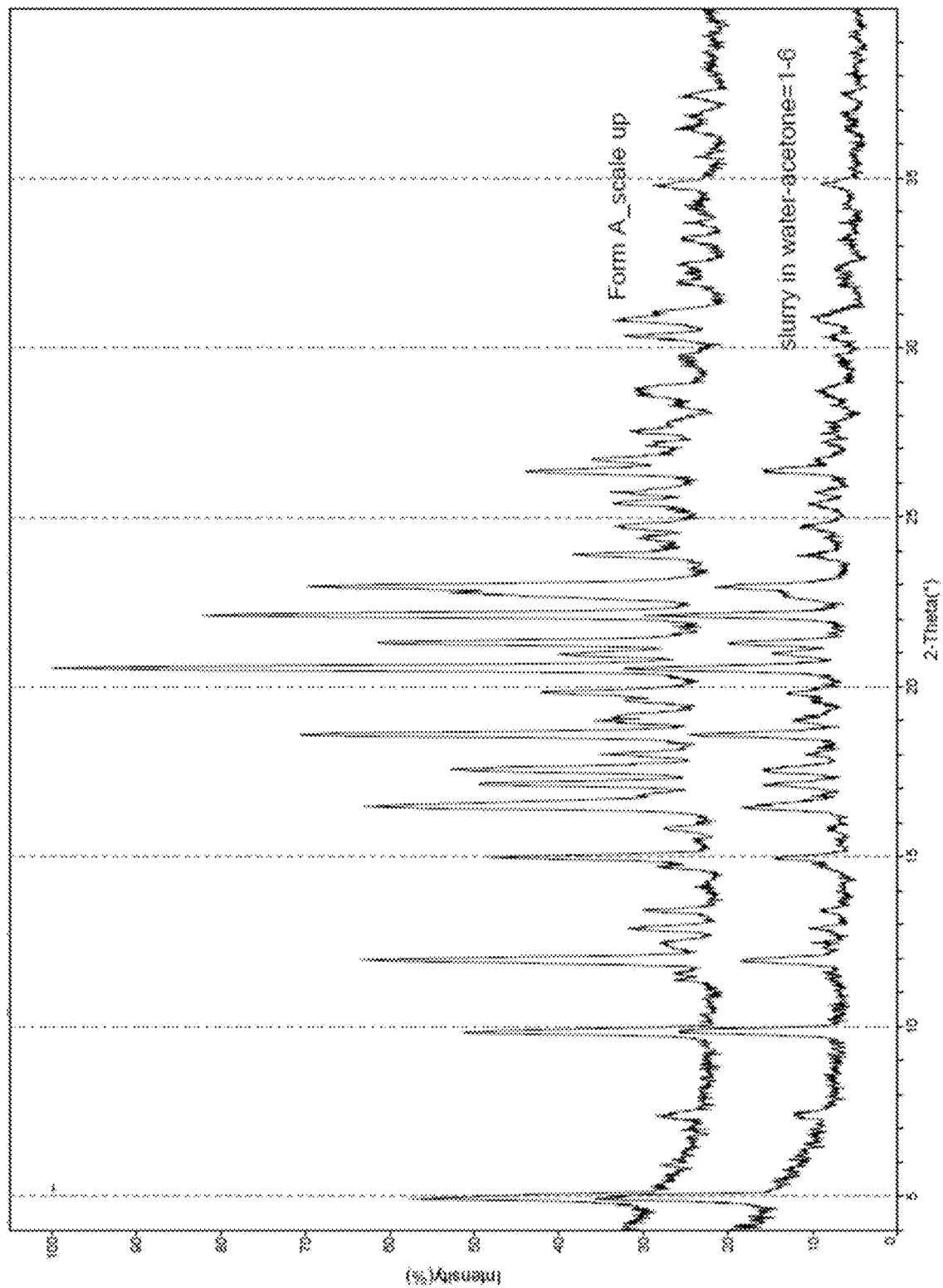
Figure 4B:
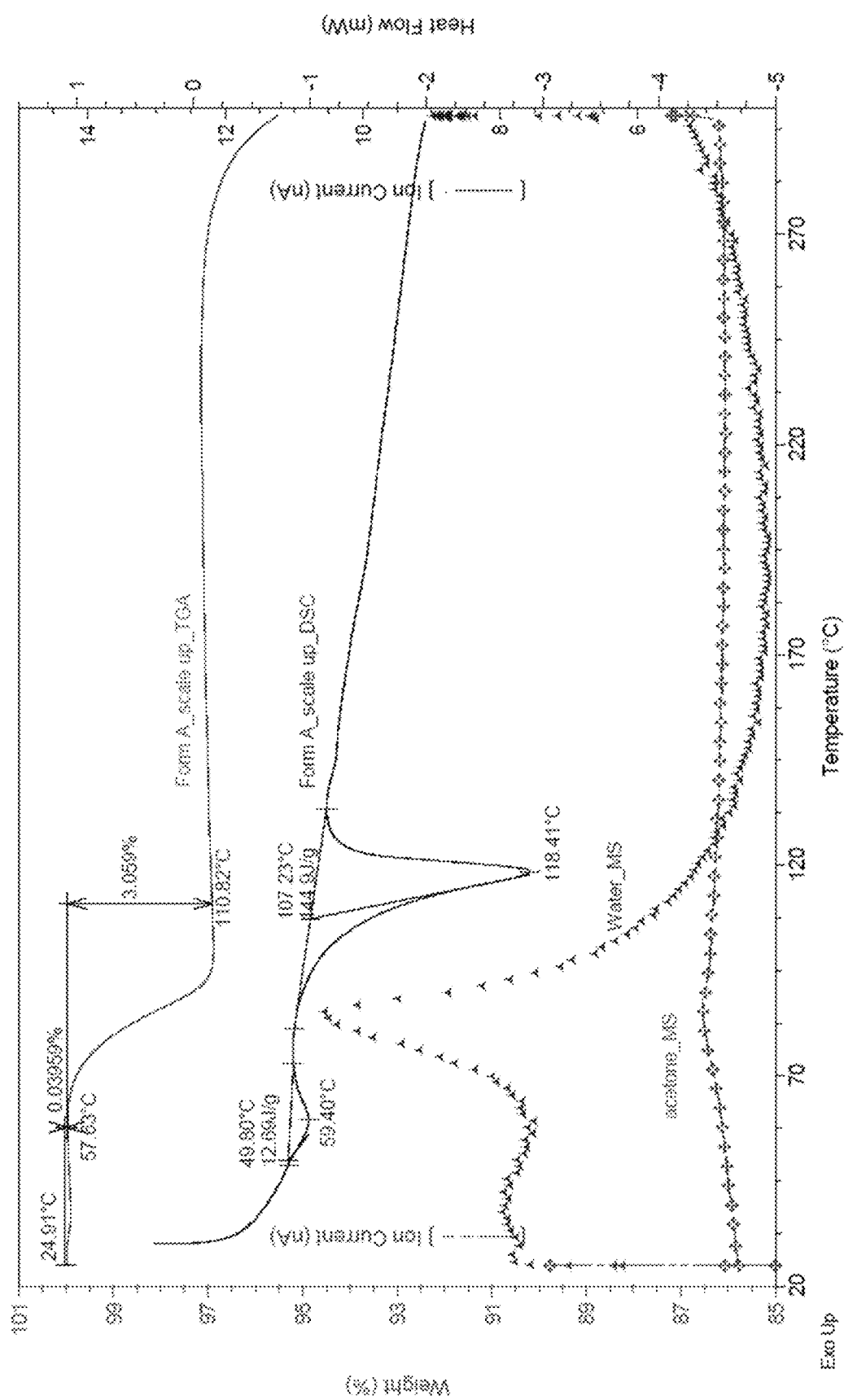
Figure 5:
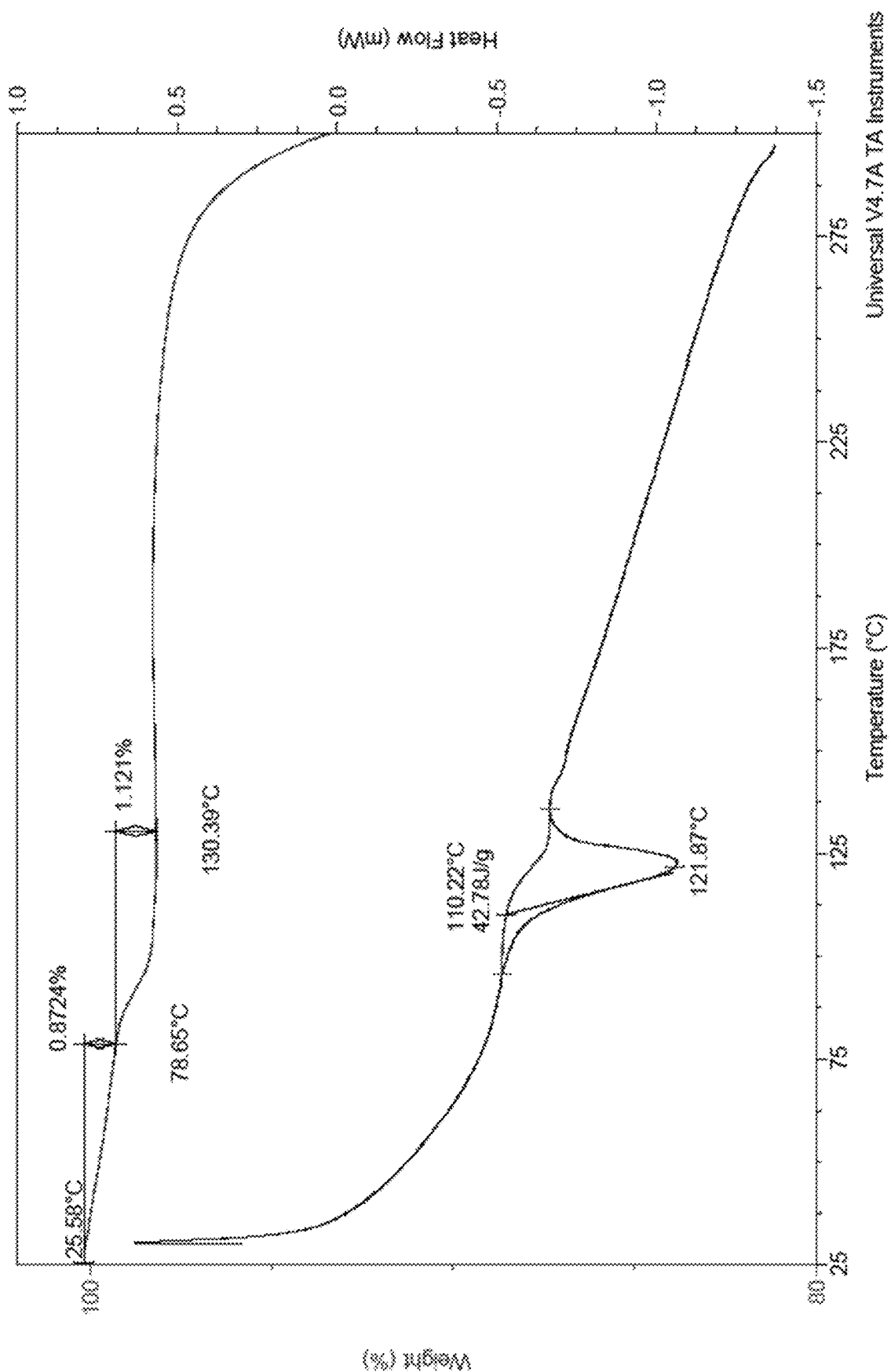
Figure 6A:
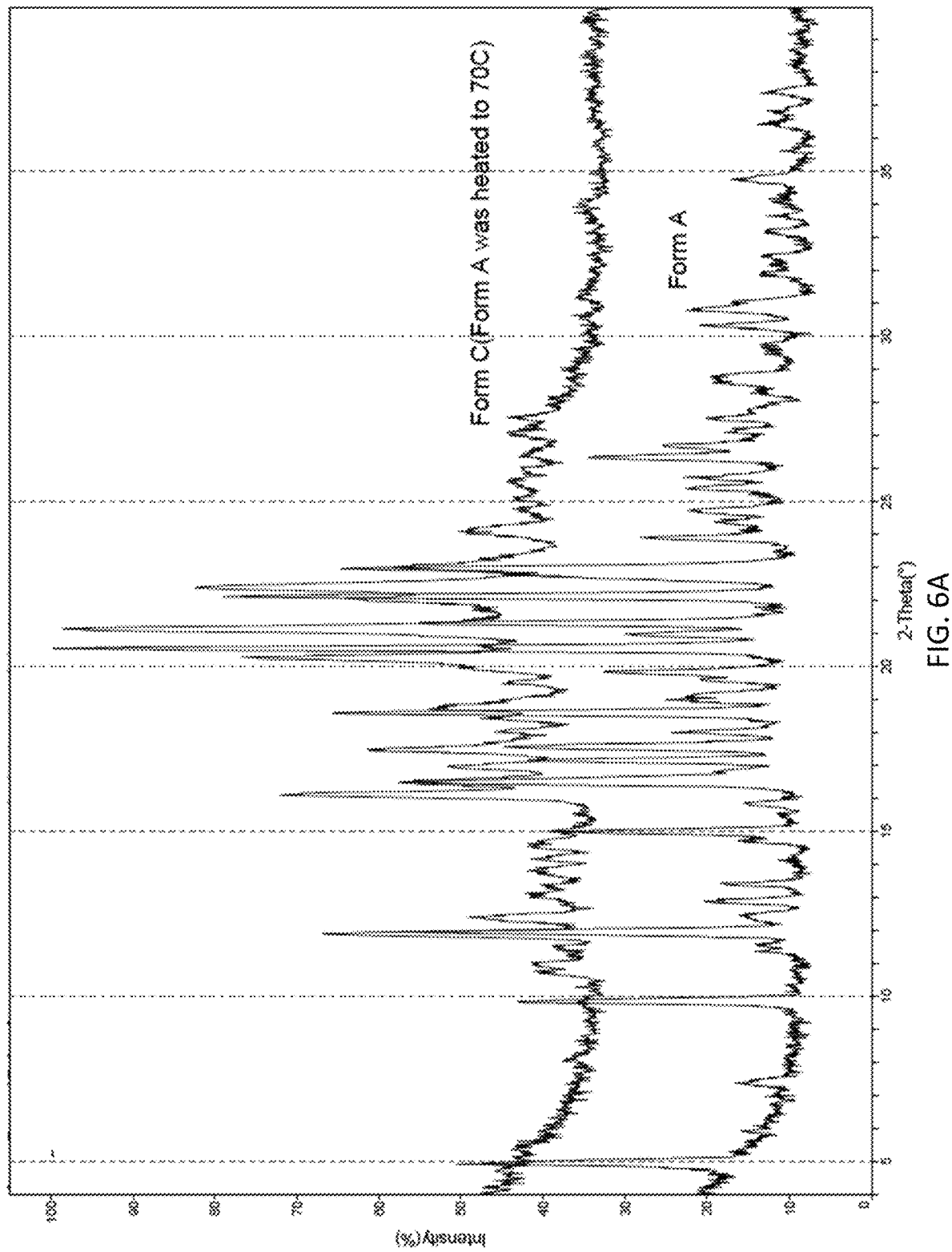
Figure 6B:
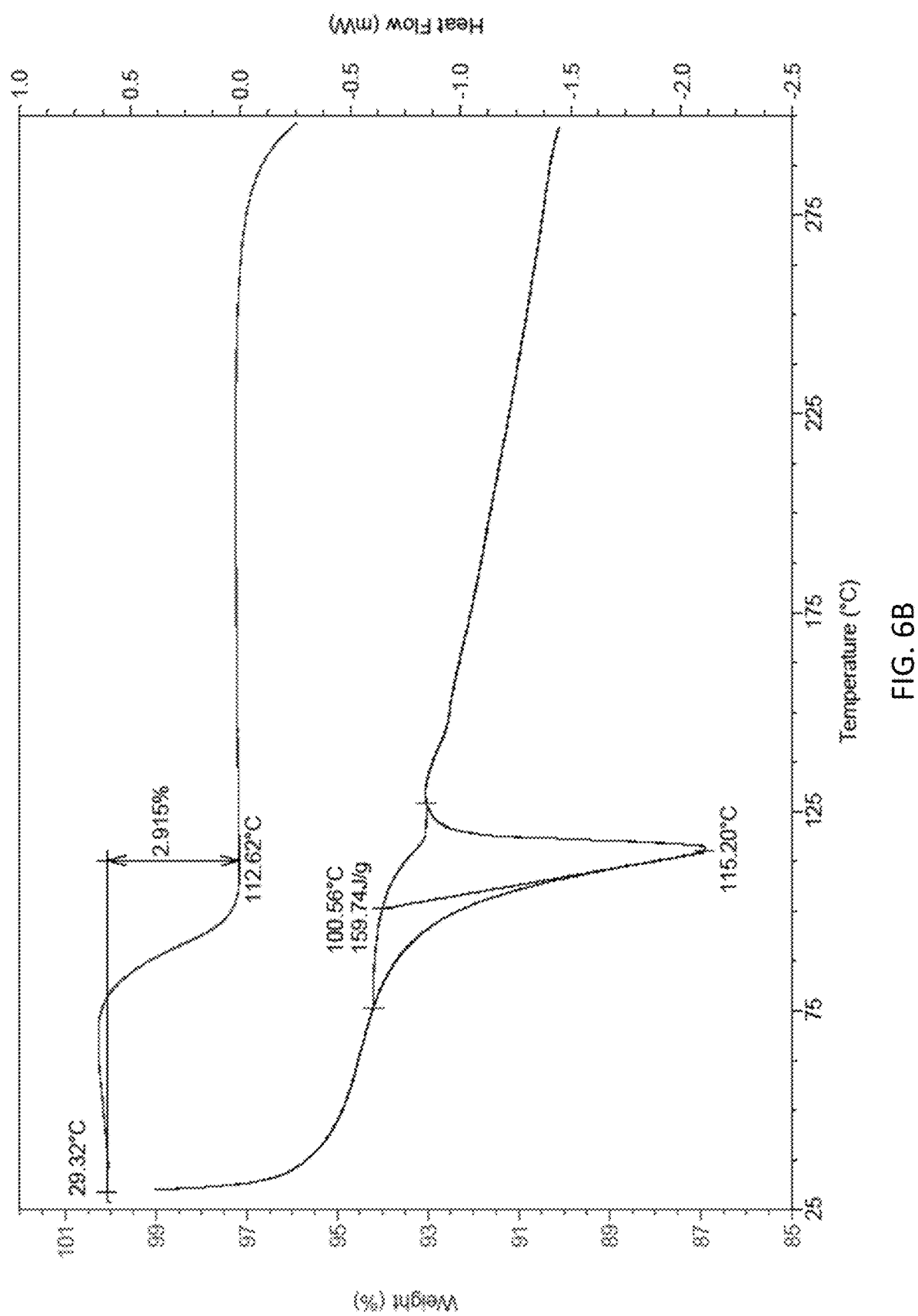
Figure 7:
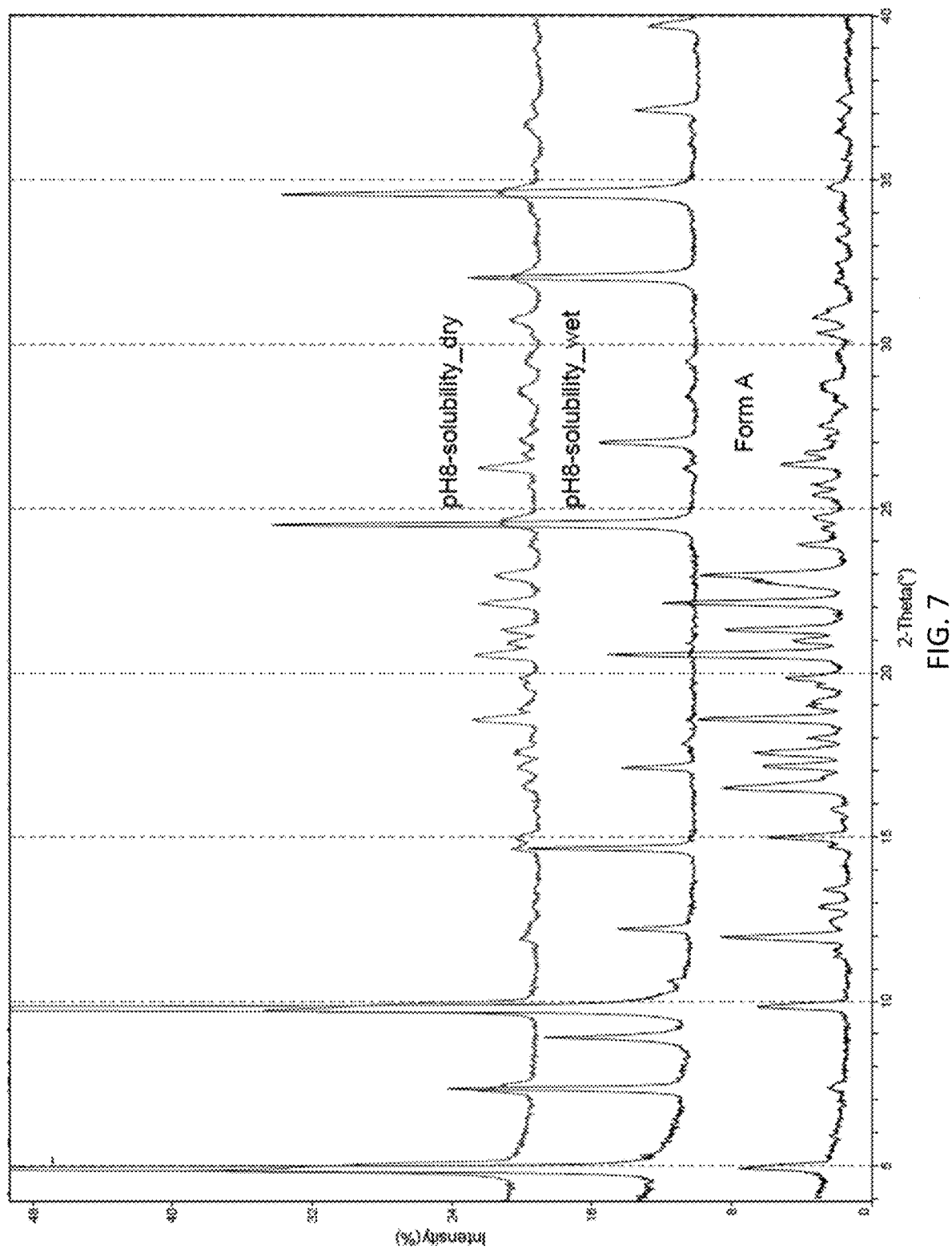
Figure 8A:
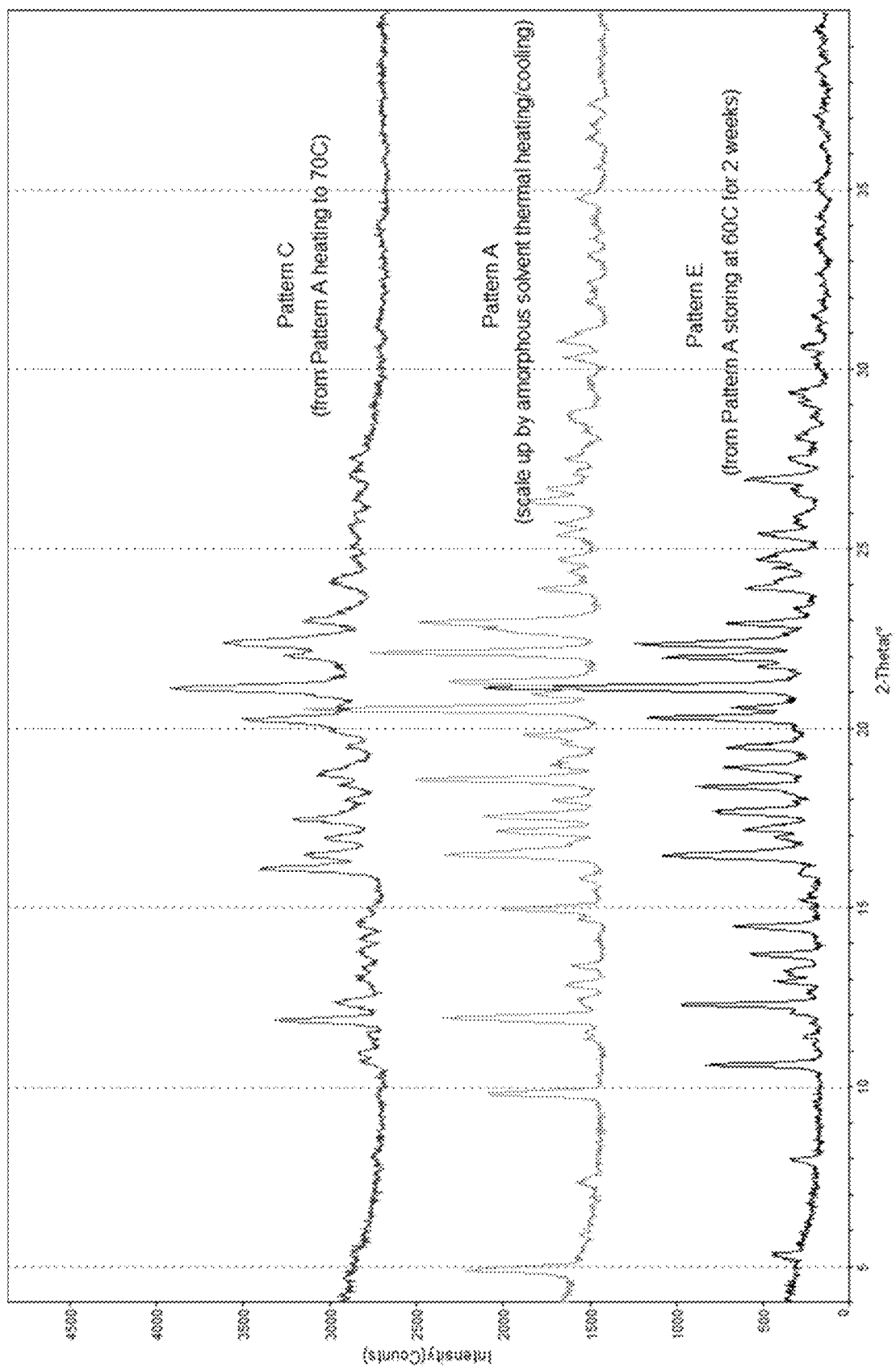
Figure 8B:
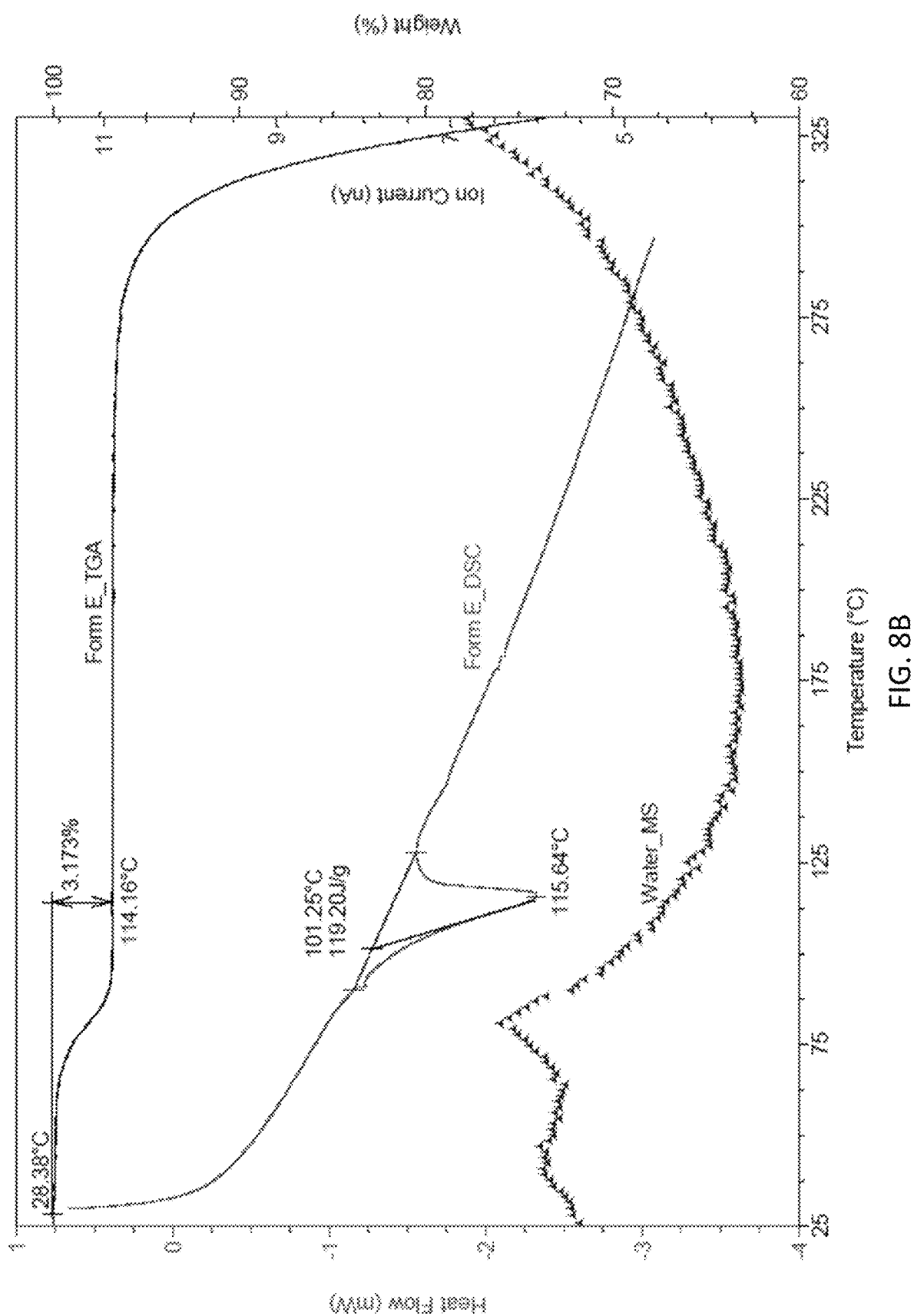
Figure 9A:
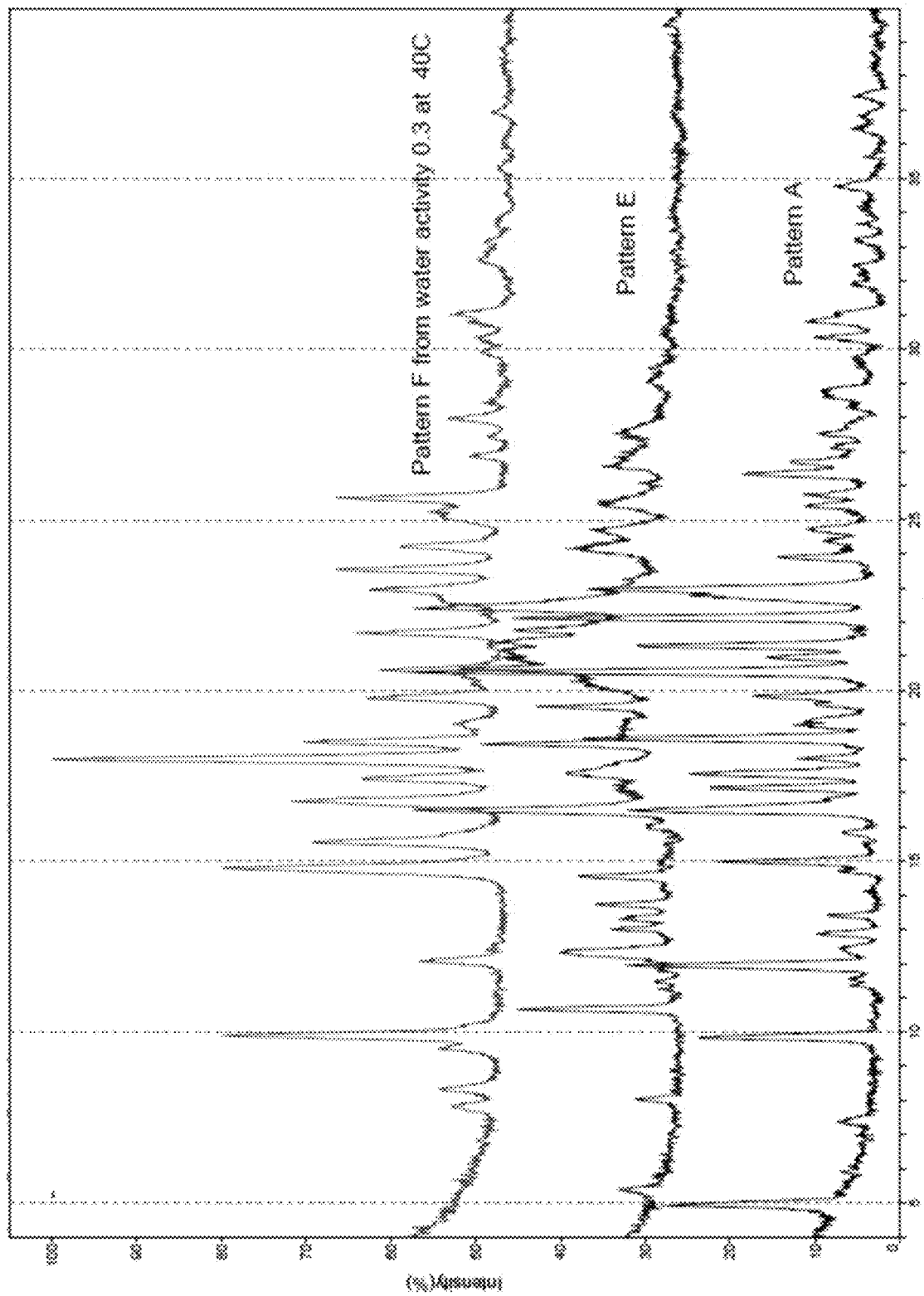
Figure 9B:
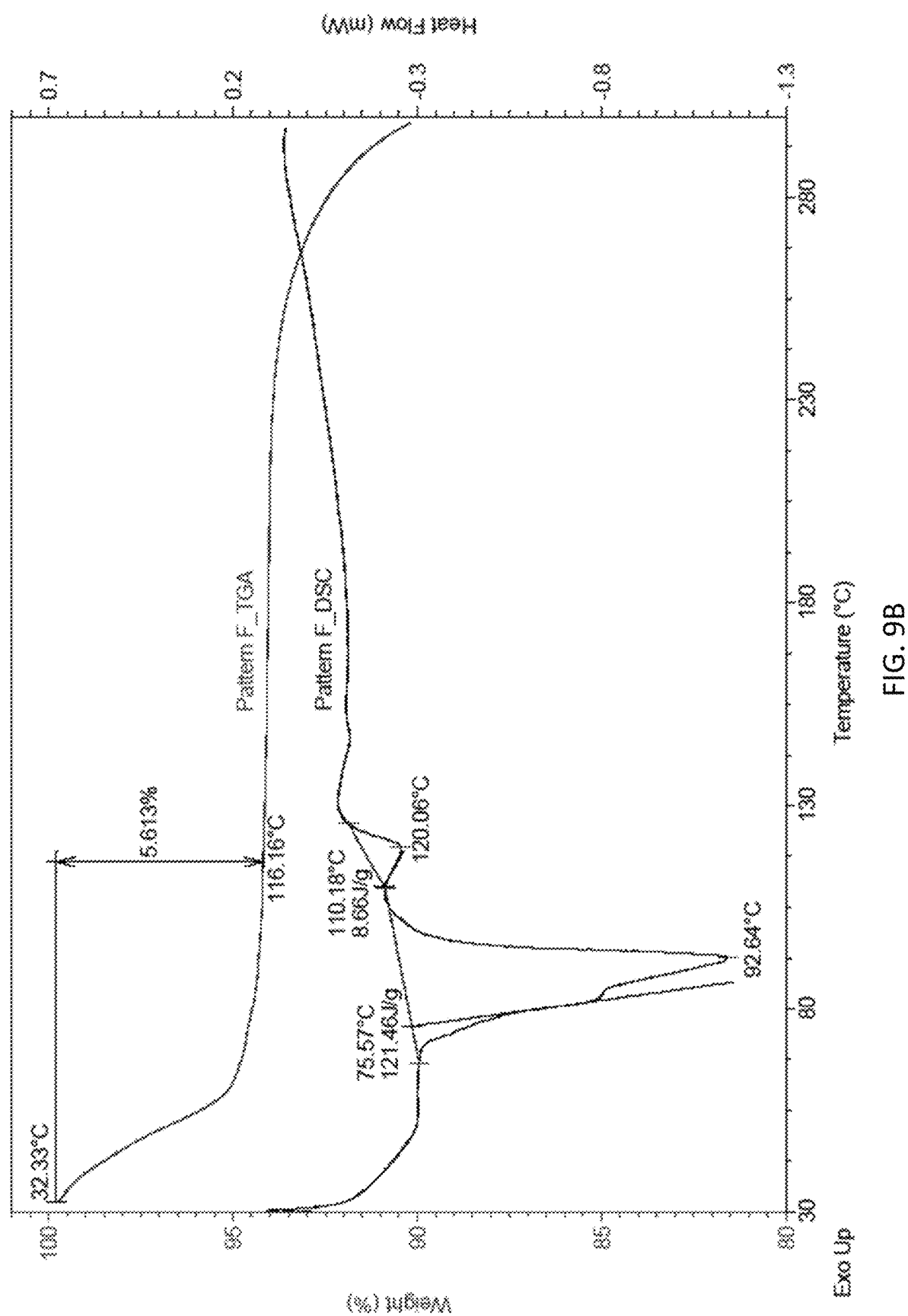

Compound I-1 can also exist in a crystalline form. In some embodiments, the crystalline form is Form A, Form B, Form C, Form D, Form E, or Form F of Compound I-1. As used herein, Form A refers to a crystalline form of Compound I-1 which can be characterized by an XRPD pattern substantially the same as FIG. 4A, or an XRPD spectrum having the major peaks of FIG. 4A. In some embodiments, Form A can be further characterized by a DSC profile substantially the same as shown in FIG. 4B, a TGA profile substantially the same as shown in FIG. 4B, or a combination thereof. As used herein, Form B refers to a crystalline form of Compound I-1 which can be characterized by a DSC profile substantially the same as shown in FIG. 5, a TGA profile substantially the same as shown in FIG. 5, or a combination thereof. As used herein, Form C refers to a crystalline form of Compound I-1 which can be characterized by an XRPD pattern substantially the same as FIG. 6A, or an XRPD spectrum having the major peaks of FIG. 6A, In some embodiments, Form C can be further characterized by a DSC profile substantially the same as shown in FIG. 6B, a TGA profile substantially the same as shown in FIG. 6B, or a combination thereof. As used herein, Form D refers to a crystalline form of Compound I-1 which can be characterized by an XRPD pattern substantially the same as FIG. 7, or an XRPD spectrum having the major peaks of FIG. 7 labeled as Form D. As used herein, Form E refers to a crystalline form of Compound I-1 which can be characterized by an XRPD pattern substantially the same as FIG. 8A (labeled as Pattern E), or an XRPD spectrum having the major peaks of FIG. 8A (labeled as Pattern E). In some embodiments, Form E can be further characterized by a DSC profile substantially the same as shown in FIG. 8B, a TGA profile substantially the same as shown in FIG. 8B, or a combination thereof. As used herein, Form F refers to a crystalline form of Compound I-1 which can be characterized by an XRPD pattern substantially the same as FIG. 9A (Pattern F), or an XRPD spectrum having the major peaks of FIG. 9A (Pattern F). In some embodiments, Form F can be further characterized by a DSC profile substantially the same as shown in FIG. 9B, a TGA profile substantially the same as shown in FIG. 9B, or a combination thereof.

The composition herein can include one or more of the various forms of Compound I-1. In some embodiments, the composition (e.g., pharmaceutical composition) comprises an amorphous form, Form A, Form B, Form C, Form D, Form E, or Form F of Compound I-1, or any combinations thereof. In some embodiments, the composition (e.g., pharmaceutical composition) can comprise only one or two forms chosen from the amorphous form, Form A, Form B, Form C, Form D, Form E, and Form F of Compound I-1, and is substantially free (e.g., not detectable by XRPD) of the other forms of Compound I-1. In some embodiments, the composition (e.g., pharmaceutical composition) can comprise amorphous Compound I-1 and is also substantially free (e.g., not detectable by XRPD) of Form A, Form B, Form C, Form D, Form E, or Form F of Compound I-1, or any combinations thereof. In some embodiments, the composition is substantially free of Compound I-1-Acid. However, in some embodiments, the composition can also comprise Compound I-1-Acid, e.g., amorphous form or Form 1 of Compound I-1-Acid. In any of the embodiments described herein, the substantially pure Compound I-1 can be in the form of amorphous, Form A, Form B, Form C, Form D, Form E, Form F, or a combination thereof.

In some embodiments, Compound I-1 can also be included in an aqueous solution. As shown in the Examples section, the free acid Compound I-1-Acid has an aqueous solubility of less than 2 µg/ml. By converting the acid into a sodium salt, aqueous solubility is greatly enhanced. Thus, one of the advantages of using a sodium salt as described herein is that solutions with high concentrations of active ingredients (e.g., Compound I-1) can be prepared. These high-concentration solutions can be used as is or can be further diluted. In some embodiments, the aqueous solution can be characterized by a high concentration of Compound I-1, for example, at least 50 mg/ml (e.g., at least 100 mg/ml, at least 150 mg/ml, at least 200 mg/ml). In some embodiments, the aqueous solution has a concentration of about 50 mg/ml, about 100 mg/ml, about 150 mg/ml, about 200 mg/ml, about 250 mg/ml, about 270 mg/ml, or any range between the specified values. In some embodiments, the aqueous solution can also have a concentration of less than 50 mg/ml, for example, about 0.1 mg/ml, about 1 mg/ml, about 10 mg/ml, about 20 mg/ml, about 30 mg/ml, about 40 mg/ml, about 50 mg/ml, or any range between the specified values. In some embodiments, the aqueous solution having a concentration of less than 50 mg/ml can be prepared from diluting an aqueous solution having a concentration higher than 50 mg/ml. In some embodiments, the aqueous solution having a concentration of less than 50 mg/ml can also be prepared by dissolving a solid form of Compound I-1, e.g., amorphous Compound I-1, in an aqueous media. As used herein, unless otherwise obvious from context, the concentration of Compound I-1 is expressed as milligrams of Compound I-1 per milliliter of the media (e.g., water for an aqueous solution).

Certain embodiments of the present invention are also directed to an aqueous solution of Compound I-1 with one or more stabilizing agents. As detailed in the Examples section, Compound I-1 has a high kinetic solubility in water. However, at high concentrations, precipitates start forming upon storage. It was found that addition of certain ingredients can stabilize aqueous solution with high concentrations of Compound I-1. For example, in some embodiments, the aqueous solution of Compound I-1 comprises one or more of sodium phosphate, sodium chloride, polysorbate, sucrose, meglumine, Cremophor RH40, Tween 80, HPβCD, and HPMC E3. In some embodiments, the aqueous solution of Compound I-1 comprises meglumine and Cremophor RH40. In some embodiments, the weight ratio of meglumine to Cremophor RH40 is about 1:5 to about 5:1.

Meglumine at various concentrations can stabilize an aqueous solution of Compound I-1, e.g., having a high concentration of Compound I-1. In some embodiments, the aqueous solution of Compound I-1 comprises meglumine in a concentration (weight to volume) of about 2% to about 5% (e.g., about 2%, about 3%, about 4%, about 5%, or any range between the specified values). In some embodiments, the aqueous solution of Compound I-1 can also comprise meglumine in a concentration (weight to volume) of below 2%. In some embodiments, the aqueous solution of Compound I-1 can also comprise meglumine in a concentration (weight to volume) of greater than 5%, such as 10%. In any of these embodiments, the aqueous solution can have a concentration of Compound I-1 of at least 50 mg/ml (e.g., at least 100 mg/ml, at least 150 mg/ml, at least 200 mg/ml). In some embodiments, the aqueous solution has a concentration of Compound I-1 of about 50 mg/ml, about 100 mg/ml, about 150 mg/ml, about 200 mg/ml, about 250 mg/ml, about 270 mg/ml, or any range between the specified values.

It was found that meglumine in a concentration of about 3% and above is effective in stabilizing aqueous solution with high concentrations of Compound I-1. Thus, in some embodiments, the present invention also provides an aqueous solution comprising Compound I-1 in a concentration of at least 200 mg/ml, and meglumine in the concentration (weight to volume) of about 3% or above. In some embodiments, the aqueous solution is characterized as being substantially free of precipitates upon storage at 25° C., e.g., for 1 week or 2 weeks.

In some embodiments, an aqueous solution with a lower concentration of Compound I-1 is desired. As discussed above, such aqueous solution can be readily prepared by diluting any one of the aqueous solution with a high concentration of Compound I-1 (e.g., with a concentration of 200 mg/ml) or can be prepared by directly dissolving Compound I-1 (e.g., amorphous Compound I-1 and/or in any other solid form), with or without the stabilizing agent (e.g., meglumine) in water.

Compound I-2

In some specific embodiments, the present invention is directed to Compound I-2. In some embodiments, the present invention provides a substantially pure compound I-2. In some embodiments, the substantially pure compound I-2 has a purity by weight and/or by HPLC of at least 70% (e.g., at least 75%, at least 80%, at least 85%, at least 90%, at least 95%, or at least 97%). In some embodiments, the substantially pure compound I-2 has a purity by weight and/or by HPLC of about 70%, about 75%, about 80%, about 85%, about 90%, about 95%, about 97%, about 99%, or any ranges between the specified values. The enantiomeric purity of the compound I-2 is about 50% ee or more, e.g., about 60% ee, about 65% ee, about 70% ee, about 75% ee, about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more, and up to 100% ee. The diastereomeric purity of compound I-2 is about 50% de or more, e.g., about 60% de, about 65% de, about 70% de, about 75% de, about 80% de, about 85% de, about 90% de, about 91% de, about 92% de, about 93% de, about 94% de, about 95% de, about 96% de, about 97% de, about 98% de, about 99% de, about 99.5% de or more, and up to 100% de. In any of the embodiments herein, the substantially pure Compound I-2 is substantially free (e.g., less than 5%, less than 2%, less than 1%, or non-detectable) of a stereoisomer other than the stereoisomer shown as Compound I-2. In any of the embodiments herein, the substantially pure Compound I-2 can also be characterized as having a purity by weight of at least 90% (e.g., at least 95%, at least 98%), a purity by HPLC area of at least 90% (e.g., at least 95%, at least 98%), or both.

The substantially pure compound I-2 can also be prepared from a substantially pure compound I-1-Acid, similar to those described for preparing Compound I-1. In some embodiments, the substantially pure Compound I-2 is prepared from an amorphous compound I-1-Acid. In some embodiments, the substantially pure Compound I-2 is prepared from Form 1 of compound I-1-Acid. In some embodiments, the substantially pure Compound I-2 is prepared from an amorphous Compound I-1-Acid, Form 1 of Compound I-1-Acid, or a combination thereof.

The substantially pure Compound I-2 herein typically has a potassium content close to the theoretical potassium content calculated based on formula of Compound I-2. In some embodiments, the substantially pure compound I-2 is characterized by a molar ratio of potassium to the carboxylate portion of Compound I-2 of about 1:1. In some embodiments, the substantially pure compound I-2 has a potassium content of about 80% to about 125% of the theoretical potassium content.

The substantially pure Compound I-2 herein can also be free or substantially free of Compound I-1-Acid, and/or can be free or substantially free of other salts of Compound I-1-Acid. In some embodiments, the substantially pure Compound I-2 is substantially free of Compound I-1-Acid, for example, with an amount of less than 20% by weight (e.g., less than 13%, less than 1%, less than 0.2%, less than 0.1% or less than 0.05%). In some embodiments, the substantially pure Compound I-2 is free of Compound I-1-Acid, other than an amount that may exist through equilibrium. In some embodiments, the substantially pure Compound I-2 has no detectable amount of Compound I-1-Acid. In some embodiments, the substantially pure Compound I-2 is substantially free of other salts of Compound I-1-Acid, for example, with an amount less than 20% by weight (e.g., less than 13%, less than 1%, less than 0.2%, less than 0.1% or less than 0.05%). In some embodiments, the substantially pure Compound I-2 includes no detectable amount of other salts of Compound I-1-Acid.

Figure 10A:
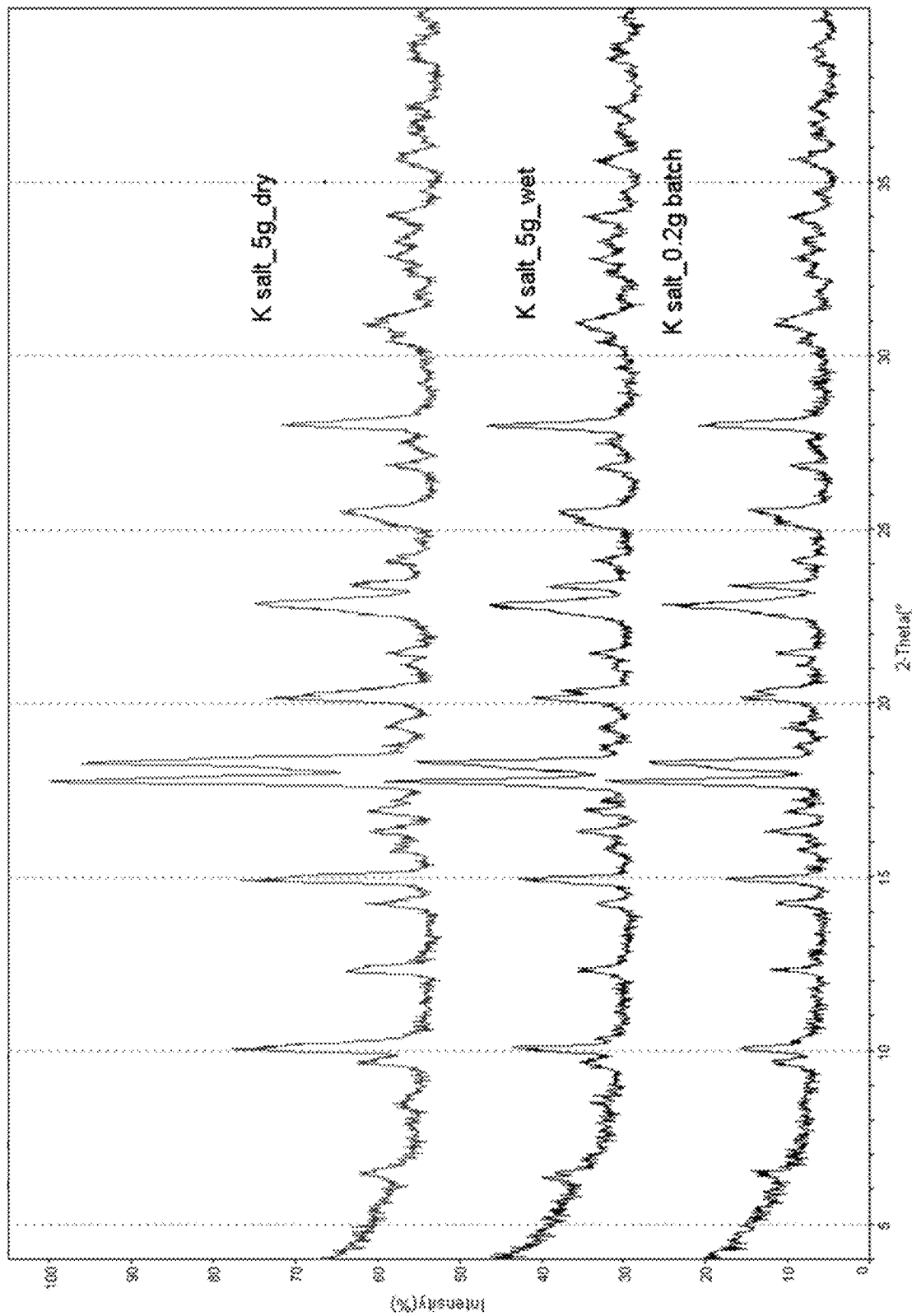
Figure 10B:
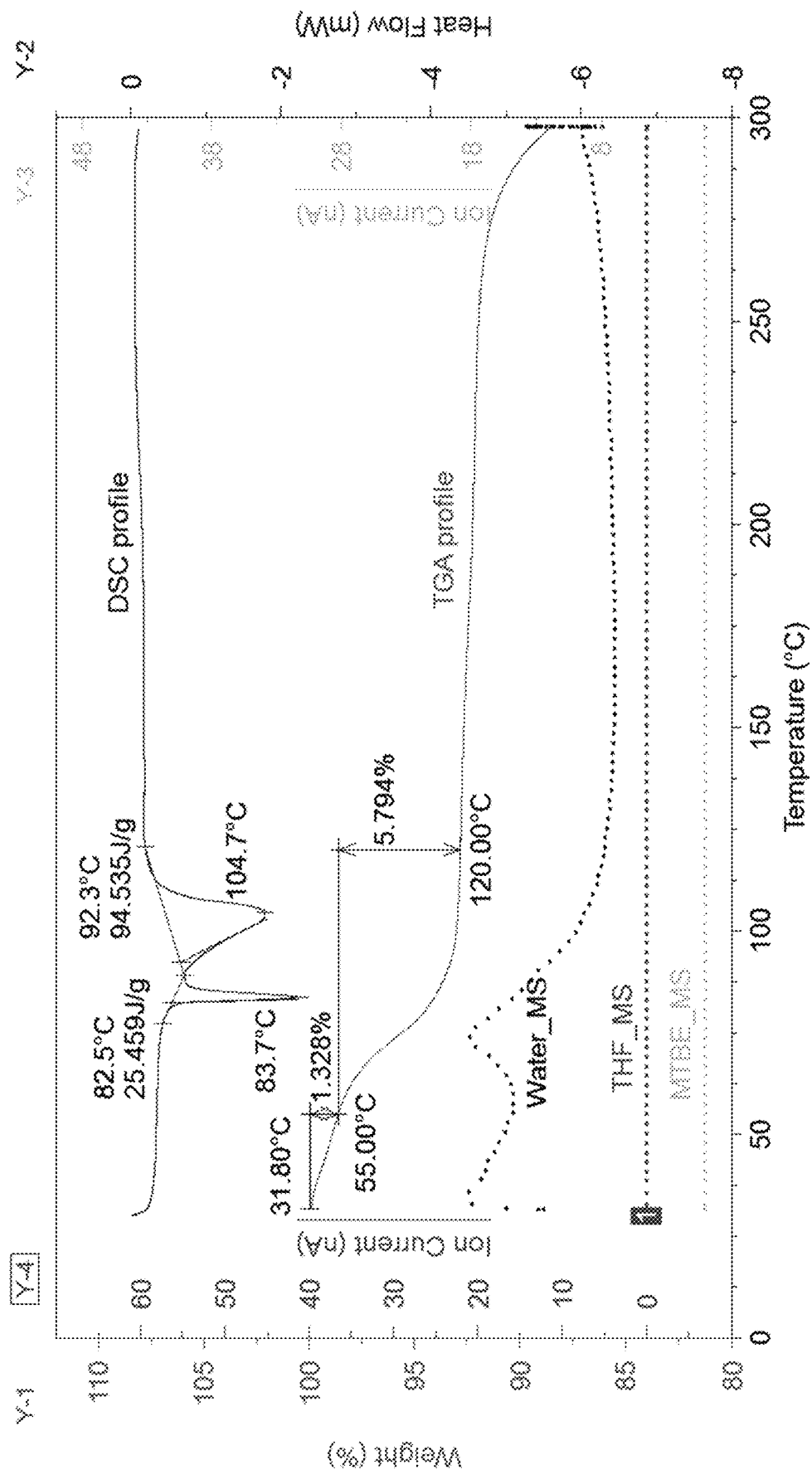
Figure 11:
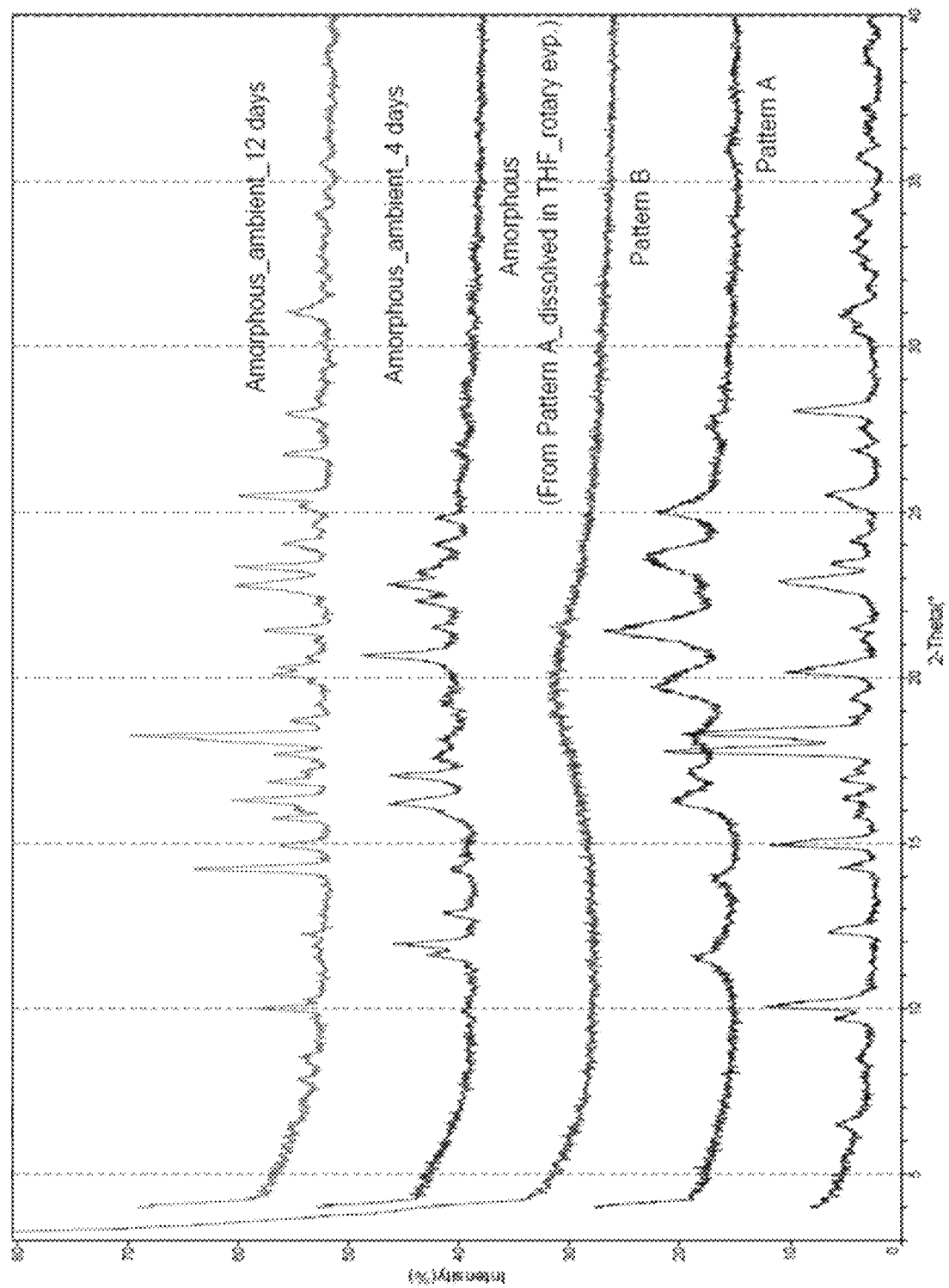
FIG. 11 shows an exemplary XRPD spectrum of amorphous Compound I-2 prepared after dissolution and evaporation using organic solvents (e.g., THF) and XRPD spectra of amorphous Compound I-2 after being stored at room temperature for 4 days and 12 days. For comparison purposes, FIG. 11 also shows XRPD spectra of Form A2 (Pattern A) and B2 (Pattern B) of Compound I-2.

Compound I-2 can exist in different solid states including amorphous form, which are useful in formulation and/or manufacturing processes. In some embodiments, the present invention provides Form A2 of Compound I-2. In some embodiments, the present invention also provides a composition (e.g., a pharmaceutical composition) comprising Form A2 of Compound I-2. As used herein, Form A2 refers to a crystalline form of Compound I-2, which can be characterized by an XRPD pattern substantially the same as FIG. 10A, or an XRPD spectrum having the major peaks of FIG. 10A. In some embodiments, Form A2 can be further characterized by a DSC profile substantially the same as shown in FIG. 10B, a TGA profile substantially the same as shown in FIG. 10B, or a combination thereof. In any of the embodiments described herein, Compound I-2 in the substantially pure Compound I-2 can be Form A2 and/or amorphous form.

In some embodiments, the present invention also provides an aqueous solution comprising Compound I-2. The aqueous solubility of the potassium salt Compound I-2 is also greatly enhanced compared to the corresponding free acid. In some embodiments, the aqueous solution is characterized by a high concentration of compound I-2, for example, at least 50 mg/ml (e.g., at least 100 mg/ml, at least 150 mg/ml, at least 200 mg/ml). In some embodiments, the aqueous solution has a concentration of Compound I-2 of about 50 mg/ml, about 100 mg/ml, about 150 mg/ml, about 200 mg/ml, about 250 mg/ml, about 270 mg/ml, or any range between the specified values. In some embodiments, the aqueous solution can also have a concentration of Compound I-2 of less than 50 mg/ml, for example, about 0.1 mg/ml, about 1 mg/ml, about 10 mg/ml, about 20 mg/ml, about 30 mg/ml, about 40 mg/ml, about 50 mg/ml, or any range between the specified values. In some embodiments, the aqueous solution having a concentration of less than 50 mg/ml is prepared from diluting an aqueous solution having a concentration higher than 50 mg/ml. In some embodiments, the aqueous solution having a concentration of less than 50 mg/ml can also be prepared by dissolving a solid form of Compound I-2, e.g., Form A2, in an aqueous media. As used herein, unless otherwise obvious from context, the concentration of Compound I-2 is expressed as milligrams of Compound I-2 per milliliter of the media (e.g., water for an aqueous solution).

The aqueous solution of Compound I-2 can also comprise one or more stabilizing agents. In some embodiments, the aqueous solution of Compound I-2 comprises one or more of sodium phosphate, sodium chloride, polysorbate, sucrose, meglumine, Cremophor RH40, Tween 80, HPβCD, and HPMC E3. In some embodiments, the aqueous solution of Compound I-2 comprises meglumine and Cremophor RH40. In some embodiments, the weight ratio of meglumine to Cremophor RH40 is about 1:5 to about 5:1.

Some embodiments are also directed to compound I-3, which can be substantially pure. The substantially pure compound I-3 can also be prepared from a substantially pure compound I-1-Acid, similar to those described for preparing compound I-1. In some embodiments, the substantially pure Compound I-3 is prepared from an amorphous compound I-1-Acid. In some embodiments, the substantially pure Compound I-3 is prepared from Form 1 of compound I-1-Acid. In some embodiments, the substantially pure Compound I-3 is prepared from an amorphous Compound I-1-Acid, Form 1 of Compound I-1-Acid, or a combination thereof.

The substantially pure Compound I-3 herein typically has a lithium content close to the theoretical lithium content calculated based on formula of Compound I-3. In some embodiments, the substantially pure compound I-3 is characterized by a molar ratio of lithium to the carboxylate portion of Compound I-3 of about 1:1. In some embodiments, the substantially pure compound I-3 has a lithium content of about 80% to about 125% of the theoretical lithium content.

Methods of Preparing Salts

In some aspects, the present invention provides a method for preparing the compound represented by Formula 1. In some embodiments, the method can comprise, as illustrated by Scheme 1 or Scheme 2 below: reacting a compound of Formula I-Acid with suitable base in a suitable solvent to provide the compound of Formula I, wherein $R^1$, A, and M are defined herein.

Scheme 1

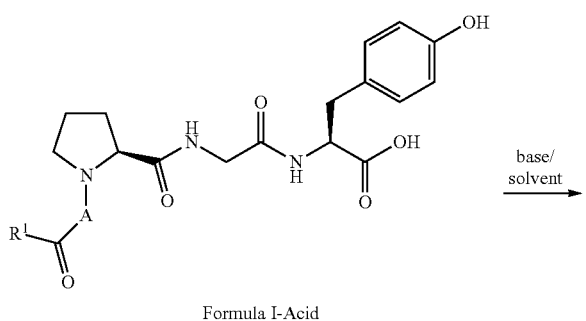

Formula I-Acid

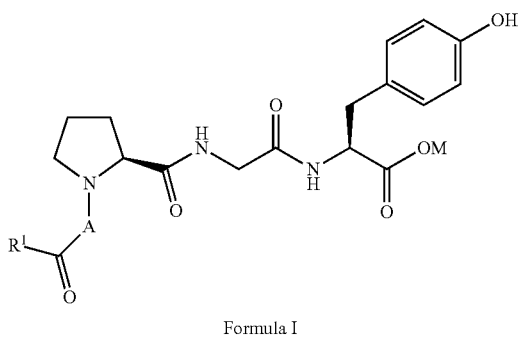

Formula I

Scheme 2

1. Fmoc-Tyr(Bzl)-OH
2. Fmoc-Gly-OH
3. Fmoc-Pro-OH
4. Fmoc-Pro-OH
5. R¹COOH $\xrightarrow{\text{Resin} \atop \text{Solvent}}$

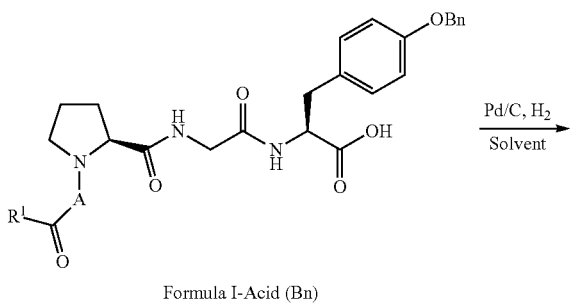

Formula I-Acid (Bn)

$\xrightarrow{\text{Pd/C, H}_2 \atop \text{Solvent}}$

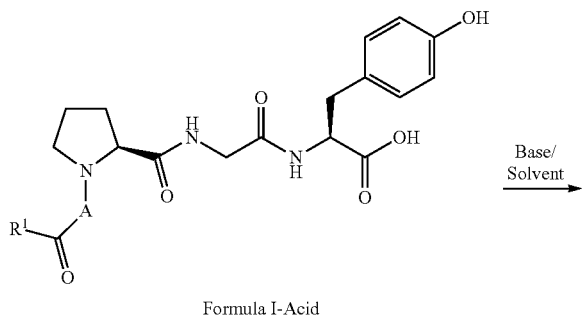

Formula I-Acid $\xrightarrow{\text{Base/} \atop \text{Solvent}}$

Formula I

Based on the salt to be prepared, various bases can be used. For example, non-limiting useful examples of inorganic bases include lithium hydroxide, sodium hydroxide, potassium hydroxide, lithium carbonate, sodium carbonate, potassium carbonate, etc.

Various solvents are suitable for the transformation. Non-limiting useful examples of solvents include an ether (e.g., tetrahydrofuran (THF), dioxane, ethyl ether and 1,2-dimethoxyethane), an alcohol (e.g., methanol, ethanol, propanol, and butanol), dimethylformamide (DMF), dimethylsulfoxide (DMSO), dichloromethane (DCM), dichloroethane, water, acetone. The solvent can be used alone or in combination.

A non-limiting example of a synthetic method for manufacturing salts from respective lipidated peptides and peptide-mimetics is as follows. (a) Mixing Compound I-Acid and one or more normalized equivalent (e.g., up to 10 equivalents) of a base (e.g. NaOH, KOH, NaHCO₃, Na₂CO₃, etc) in a solvent such as water, ethanol, isopropyl alcohol ("IPA"), ethyl acetate ("EtOAc") or other solvents; stirring the mixture until it becomes a solution; and then removing the solvent at room temperature to obtain the desired salts. (b) The salts obtained from (a) can be further purified through recrystallization. In one example, the salts can be dissolved further in water or other solvents, and recrystallized at low temperature to afford purified salts. Alternatively, recrystallization can also be carried out through evaporation of solvent at room temperature or allowing it to stand at room temperature for a few days. (c) The crystalline salts obtained can be converted into amorphous form using organic solvent. Non-limiting manufacturing examples are also shown in the Examples section.

In some embodiments, the desired salt can also be prepared through a salt-exchange reaction. In some embodiments, the desired salt can also be directly prepared through the hydrolysis of ester form of Compound I-1-Acid (e.g. Compound C in Scheme 3) without isolating Compound I-1-Acid. General methods for performing salt exchange are known in the art.

In some embodiments, the present invention provides a method of preparing a compound having Formula I-C,

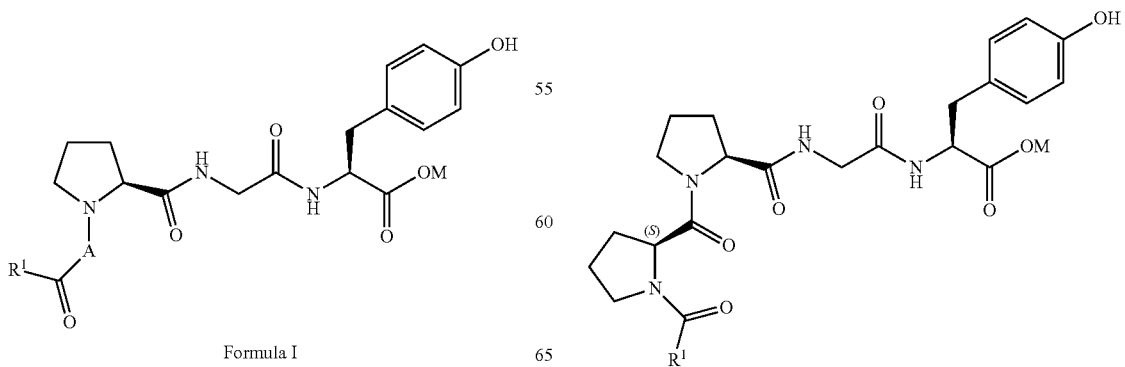

Formula I-C comprising the steps of (a) providing a mixture comprising the compound I-C-Acid in water;

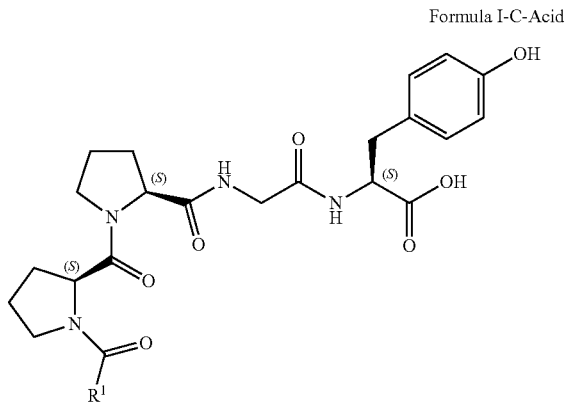

Formula I-C-Acid (b) adding $M_2CO_3$, $MHCO_3$ or MOH to the mixture of step (a);

(c) heating and stirring the mixture of step (b);

(d) cooling the mixture of step (c); and (e) filtering the mixture of step (d), wherein M is Li, Na, or K; and $R^1$ is a straight chain or branched chain $C_{1-36}$ alkyl, a straight chain or branched chain $C_{2-36}$ alkenyl, or a straight chain or branched chain $C_{2-36}$ alkynyl. In some specific embodiments, M is Na.

In some embodiments, the present invention provides a method of preparing a compound having Formula I-C, Formula I-C comprising the steps of (a) providing a mixture comprising the compound I-C-Acid in protic organic solvents with or without water;

Formula I-C-Acid (b) adding $M_2CO_3$, $MHCO_3$ or MOH to the mixture of step (a);

(c) stirring the mixture of step (b);

(d) removing solvents from the mixture of step (c) under reduced pressure; and (e) removing water from the mixture of step (d) by lyophilization, wherein M is Li, Na, or K; and $R^1$ is a straight chain or branched chain $C_{1-36}$ alkyl, a straight chain or branched chain $C_{2-36}$ alkenyl, or a straight chain or branched chain $C_{2-36}$ alkynyl. In some specific embodiments, M is Na.

Methods of Preparing Amorphous Form of Compounds

In some embodiments, the present invention provides a method of preparing amorphous form of a compound having Formula I-C, Formula I-C comprising the steps of (a) providing a crystalline form of the Formula I-C in organic solvents;

(b) heating and stirring the mixture of step (a); and (c) removing organic solvents from the mixture of step (b) to provide a compound having amorphous form of Formula I-C, wherein M is Li, Na, or K; and $R^1$ is a straight chain or branched chain $C_{1-36}$ alkyl, a straight chain or branched chain $C_{2-36}$ alkenyl, or a straight chain or branched chain $C_{2-36}$ alkynyl. In some specific embodiments, M is Na.

Pharmaceutical Compositions Comprising the Salt

In some embodiments, the present invention provides a pharmaceutical composition comprising a compound of Formula I (e.g., a compound of Formula I-B or I-C, or any one of compounds I-1 to I-10). In some embodiments, the compound of Formula I is a substantially pure compound as described herein.

For example, in some embodiments, the pharmaceutical composition comprises compound I-1, I-2, I-3, I-4, I-5 and/or I-6,

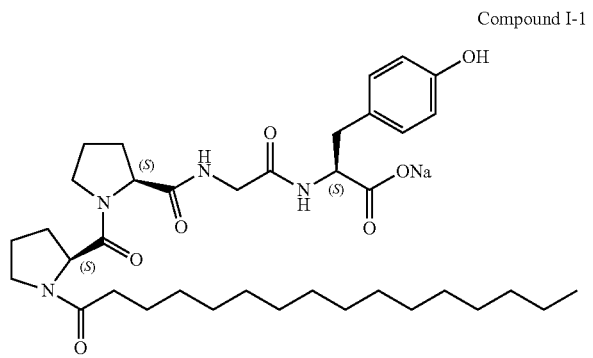
Compound I-1

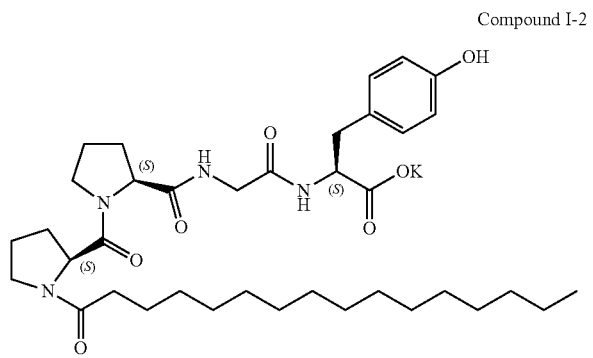
Compound I-2

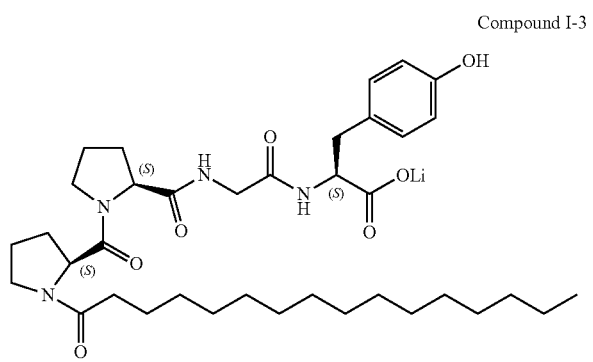
Compound I-3

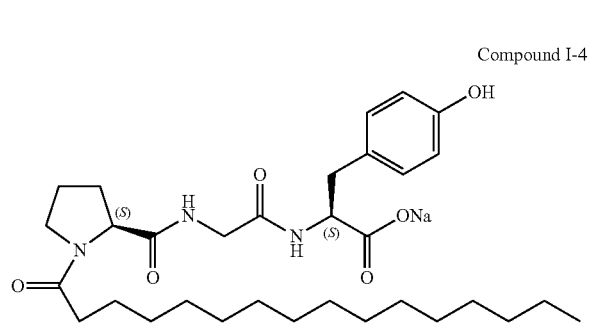
Compound I-4

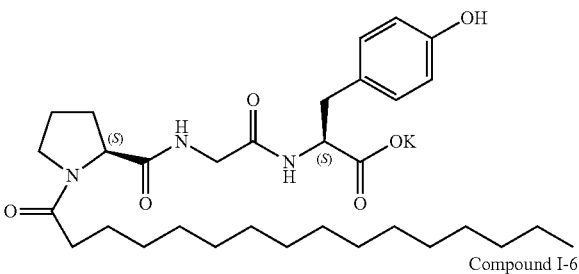
Compound I-5

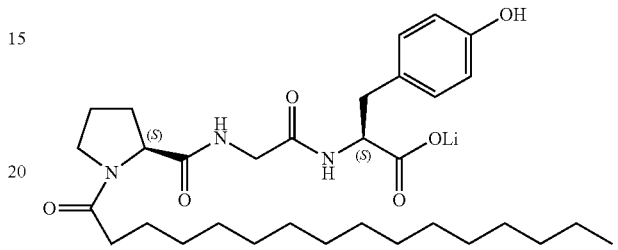
Compound I-6

In some specific embodiments, the pharmaceutical composition comprises compound I-1. In some embodiments, the compound I-1 can be a substantially pure compound I-1 as described herein.

Typically, the compound of Formula I can be included in a pharmaceutical composition in a therapeutically effective amount. In some embodiments, the pharmaceutical composition can comprise the compound of Formula I in an amount effective for treating a disease or disorder mediated by formation of a Pellino-1 induced inflammatory signal transduction complex such as MyD88 and/or RIP1, for example, the disease or disorder can be one or more of multiple sclerosis, psoriasis, sepsis, geographic atrophy, wet age-related macular disease, dry age-related macular disease, diabetic retinopathy, infectious lung diseases, bacterial pneumonia, viral pneumonia, diffuse large B-cell lymphoma, viral infection, autoimmune disease, obesity, blood cancer including lymphoma, and tumors in internal organs. In some embodiments, the pharmaceutical composition can comprise the compound of Formula I in an amount effective for treating an inflammatory bowel disease (e.g., ulcerative colitis, Behcet's disease, and/or Crohn's disease). In some embodiments, the pharmaceutical composition can comprise the compound of Formula I in an amount effective for treating alopecia. In some embodiments, the active ingredient in the pharmaceutical composition consists essentially of the compound of Formula I. In some embodiments, the pharmaceutical composition can also include one or more additional active ingredients, for example, in an amount effective for treating one or more of the diseases or disorders described herein.

The pharmaceutical composition can be formulated for different routes of administration, including but are not limited to oral, nasal, pulmonary, rectal, buccal, vaginal, ocular, topical, parenteral or transdermal administration. In some embodiments, the pharmaceutical composition can be formulated for oral administration. In some embodiments, the pharmaceutical composition can be formulated for injection, such as intravenous or intravitreal injection.

The pharmaceutical composition can exist in various forms. In some embodiments, the pharmaceutical composition can be a solid or liquid. In some embodiments, the pharmaceutical composition can be a solution, suspension, semi-liquid, semi-solid, gel, emulsion, ointment, capsule, tablet, or cream. In some embodiments, the pharmaceutical composition is in the form of a capsule or tablet. In some embodiments, the pharmaceutical composition can be in the form of a solution, such as an oral solution or an injectable solution. General methods for preparing formulations such as capsules, tablets, and solutions are known in the art and can be adapted for the pharmaceutical compositions herein. The Examples section also describes preparation of exemplary pharmaceutical compositions according the present disclosure.

The pharmaceutical composition described herein can optionally include one or more pharmaceutically acceptable excipient or carrier, which can be selected based on its route of administration. For example, in some embodiments, the pharmaceutical composition can comprise one or more (e.g., two or more, e.g., 2, 3, 4, 5, 6, 7, 8, or more) of pharmaceutically acceptable excipients or carriers chosen from antioxidants, stabilizers, preservatives, pH adjusting and/or buffering agents, tonicity adjusting agents, thickening agents, suspending agents, binding agents, viscosity-increasing agents, and the like. In some embodiments, the pharmaceutical composition can comprise processing agents, drug delivery modifiers and/or enhancers, such as, calcium phosphate, magnesium stearate, talc, monosaccharides, disaccharides, starch, gelatin, cellulose, methyl cellulose, sodium carboxymethyl cellulose, dextrose, hydroxypropyl-beta-cyclodextrin (HPβCD), polyvinylpyrrolidinone, low melting waxes, ion exchange resins, and the like, and any combinations thereof. Any suitable amount of such excipients and carriers can be used. In some embodiments, the excipients and carriers are used in an amount at or below the upper limit of the respective excipient or carrier that the US Food and Drug Administration, or other corresponding competent agencies, has determined to be safe for human use. Suitable examples of pharmaceutically acceptable excipients and carriers are described herein. Additional suitable examples can be found in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), the contents of which are incorporated herein by reference in their entirety.

Dosage Forms Comprising Compound I-1

Certain embodiments of the present invention are directed to a pharmaceutical composition comprising a therapeutically effective amount of Compound I-1 and optionally a pharmaceutically acceptable excipient or carrier. In some embodiments, the pharmaceutical composition comprising Compound I-1 can be formulated for oral, nasal, pulmonary, rectal, buccal, vaginal, ocular, topical, parenteral or transdermal administration. For example, in some embodiments, the pharmaceutical composition comprises Compound I-1 in an oral formulation, such as a capsule, tablet, or aqueous solution.

Compound I-1 in the pharmaceutical composition can be in different solid states. For example, in any of the embodiments described herein, Compound I-1 can be in an amorphous form. In some embodiments, the pharmaceutical composition can also comprise one or more of the crystalline forms of Compound I-1. For example, in some embodiments, the pharmaceutical composition can comprise Form A, Form B, Form C, Form D, Form E, and/or Form F of Compound I-1. In some embodiments, the pharmaceutical composition comprises Form A of the compound I-1. In some embodiments, the pharmaceutical composition comprises Form C of the compound I-1. In some embodiments, the pharmaceutical composition comprises Form E of the compound I-1. In some embodiments, the pharmaceutical composition can comprise amorphous Compound I-1 and one or more of the crystalline forms Form A, Form B, Form C, Form D, Form E, and/or Form F of Compound I-1.

Figure 12:
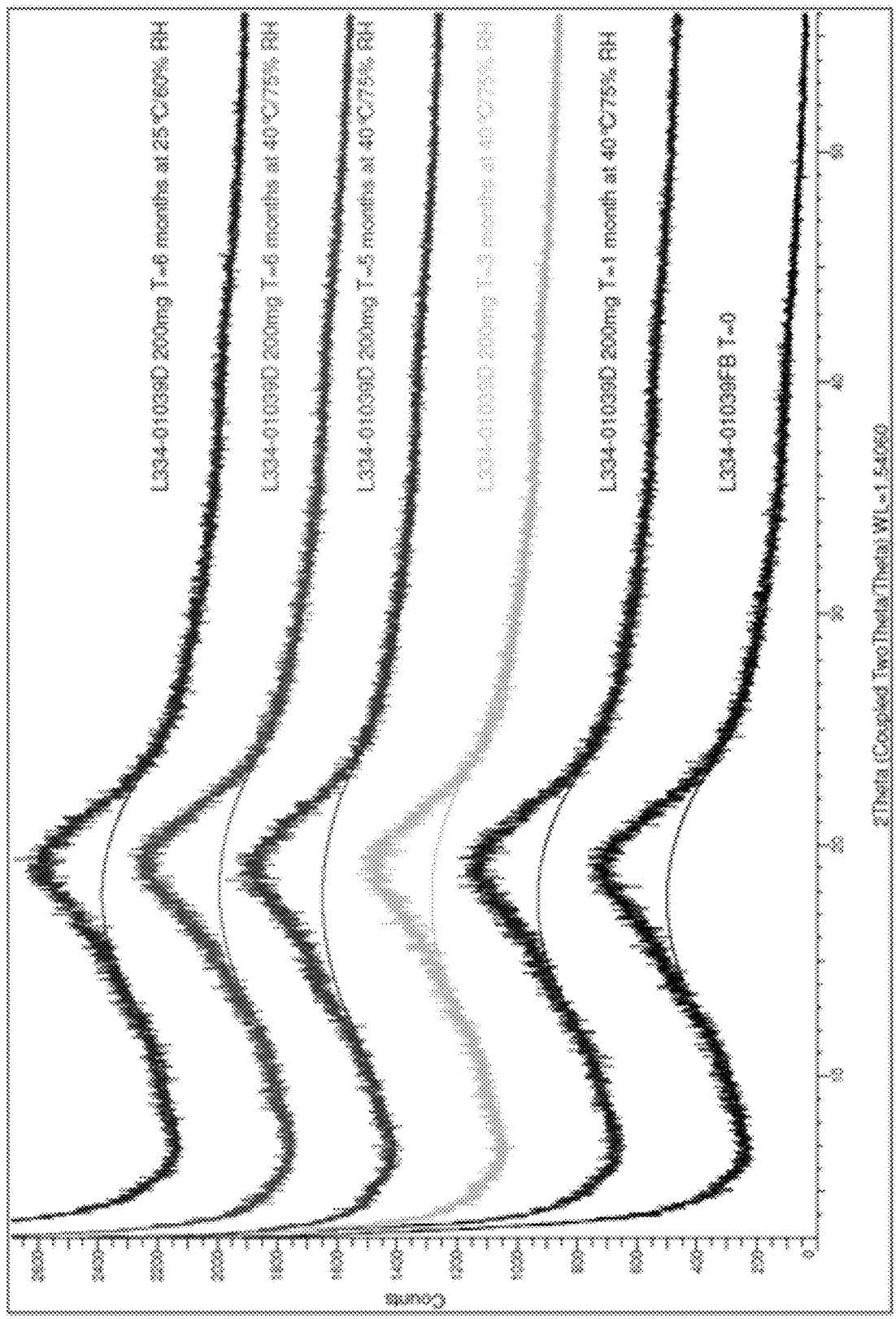
FIG. 12 shows X-ray diffractograms of powder from capsules containing amorphous Compound I-1. The diffractographs show that no crystalline conversion was observed after 6 month when the capsules were stored under conditions of 25° C./60% RH or 40° C./75% RH (relative humidity).
Figure 13:
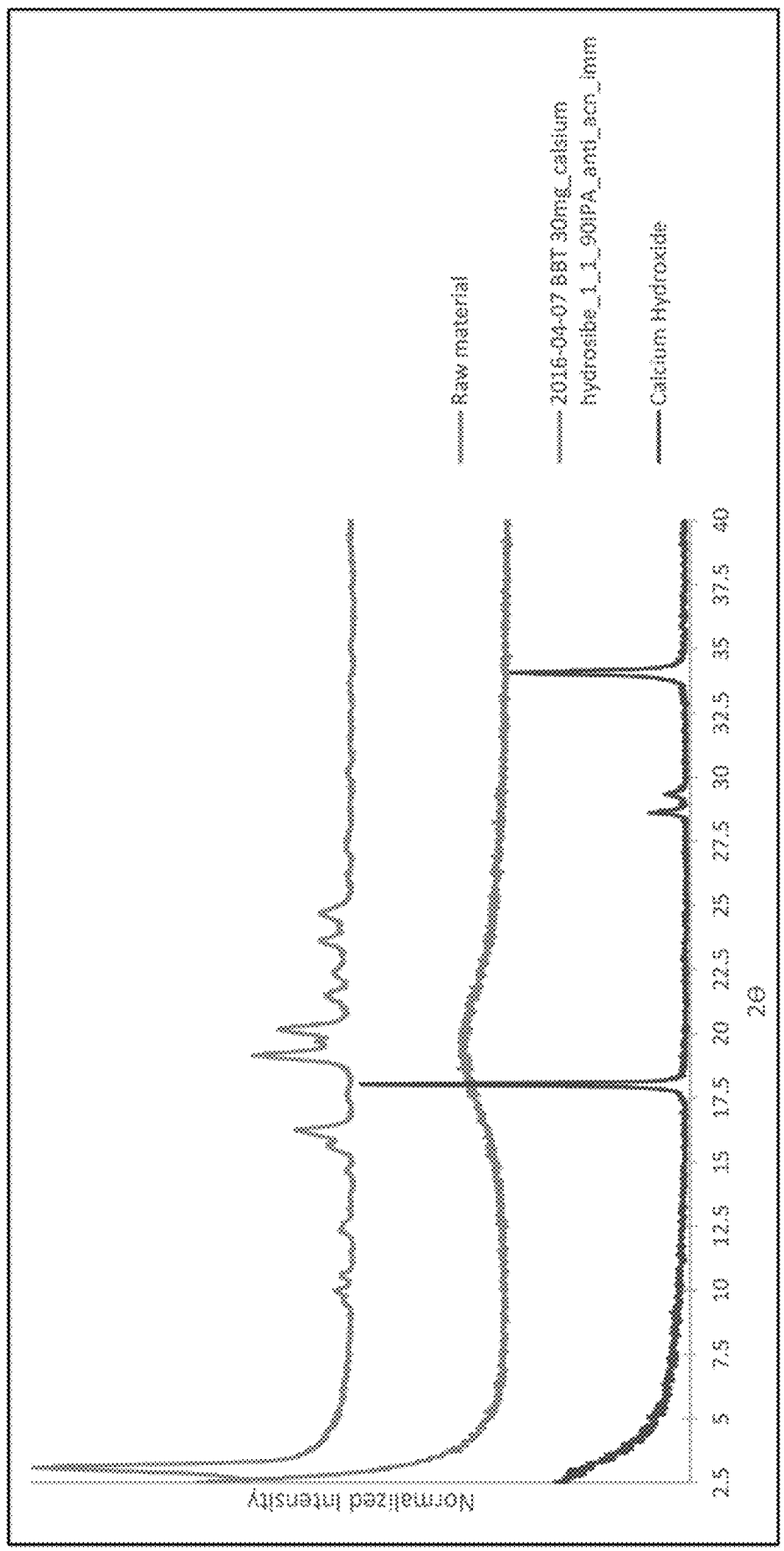
FIG. 13 shows XRPD spectrum of amorphous Compound I-1-Acid calcium salt prepared by taking Compound I-1-

In some embodiments, the pharmaceutical composition comprising amorphous Compound I-1 is storage stable. For example, in some embodiments, upon storage at 40° C. at a relative humidity of 75% or at 25° C. at a relative humidity of 60% for 1 month or more (e.g., 1 month, 6 months, or more), the pharmaceutical composition comprising amorphous Compound I-1 is substantially free (e.g., less than 10%, or not detectable by XRPD) of the compound I-1 in a crystalline form. In some embodiments, upon storage at 40° C. at a relative humidity of 75% for 1 month or more (e.g., 1 month, 6 months, or more), the pharmaceutical composition can be characterized by an X-ray powder diffraction (XRPD) pattern substantially the same as shown in FIG. 12 at the respective time point.

Accordingly, in some embodiments, the pharmaceutical composition comprising amorphous Compound I-1 can be substantially free (e.g., less than 10%, or not detectable by XRPD) of a crystalline form of Compound I-1. In some embodiments, the pharmaceutical composition comprising amorphous Compound I-1 is substantially free of Form A of Compound I-1. In some embodiments, the pharmaceutical composition comprising amorphous Compound I-1 is substantially free of Form C of Compound I-1. In some embodiments, the pharmaceutical composition comprising amorphous Compound I-1 is substantially free of Form D of Compound I-1. In some embodiments, the pharmaceutical composition comprising amorphous Compound I-1 is substantially free of Form E of Compound I-1. In some embodiments, the pharmaceutical composition comprising amorphous Compound I-1 is substantially free of Form F of Compound I-1. In some embodiments, the pharmaceutical composition comprising amorphous Compound I-1 is substantially free of one or more of Form A, Form B, Form C, Form D, Form E, and Form F of Compound I-1.

In some embodiments, the pharmaceutical composition comprising Compound I-1 is formulated as a solid dosage form. In any of the embodiments described herein, the pharmaceutical composition can be enteric coated. In some embodiments, the solid dosage form is an oral solid dosage form. In some embodiments, the solid dosage form is a capsule or tablet. In some embodiments, the capsule or tablet is enteric coated.

Various enteric coatings are suitable. Using capsules and tablets as an example, in some embodiments, the capsule or tablet can comprise enteric coated particles comprising Compound I-1. It should be noted that the enteric coated particles by themselves are also a feature of the present invention. In some embodiments, the outer surface of the capsule or tablet can be enteric coated. As such, particles of Compound I-1 do not need to be separately enteric coated. However, in some embodiments, the capsule or tablet can comprise enteric coated particles comprising Compound I-1 with an enteric coated outer surface. General methods for enteric coating are known in the art and can be adapted for the solid dosage form herein. Suitable materials for enteric coating are also known in the art. For example, in some embodiments, the enteric coating includes one or more methacrylic acid-methylmethacrylate copolymers. In some embodiments, the enteric coating includes one or more of methacrylic acid-methylmethacrylate (1:1 or 1:2 ratio)

copolymers, which are commercially available under the tradename Eudragit® L 100 or Eudragit® S 100, respectively.

The pharmaceutical composition comprising Compound I-1 (e.g., amorphous Compound I-1) can also be characterized by an in vitro dissolution profile. As discussed herein, Compound I-1 shows unexpectedly high kinetic solubility. Without wishing to be bound by any theories, this high kinetic solubility also imparts desired in vitro dissolution profile of certain dosage forms, which are useful in various applications, e.g., in the methods of treatment as described herein.

In some embodiments, the in vitro dissolution profile includes one or more of the following: (1) upon placement of the composition in an in vitro dissolution test comprising USP Dissolution Method at 100 rpm in 500 ml 0.1 N HCl at 37° C. using Type II Paddle, substantially no compound I-1 or the free acid form is released from the composition at about 2 hours to about 4 hours (e.g., at about 2 hours) in the test; and (2) upon placement of the composition in an in vitro dissolution test comprising USP Dissolution Method at 100 rpm in approximately 1000 ml media at pH 7.4 at 37° C. using Type II Paddle, about 20% or more (e.g., about 20-65%, about 40-65%) of the compound I-1 is released from the composition at about 1 hour in the test, about 65-100% (e.g., about 80-100%) of the compound I-1 is released from the composition at about 2 hours to about 4 hours in the test. In some embodiments, the in vitro dissolution profile includes one or more of the following: (1) upon placement of the composition in an in vitro dissolution test comprising USP Dissolution Method at 100 rpm in 500 ml 0.1 N HCl at 37° C. using Type II Paddle, substantially no compound I-1 or the free acid form is released from the composition at about 2 hours to about 4 hours (e.g., at about 2 hours) in the test; and (2) upon placement of the composition in an in vitro dissolution test comprising USP Dissolution Method at 100 rpm in approximately 1000 ml media at pH 7.4 at 37° C. using Type II Paddle, at least 80% (e.g., essentially all) of the compound I-1 is released from the composition at about 1 hour to about 4 hours in the test. In some embodiments, the in vitro dissolution profile includes one or more of the following: (1) upon placement of the composition in an in vitro dissolution test comprising USP Dissolution Method at 100 rpm in 500 ml 0.1 N HCl at 37° C. using Type II Paddle, substantially no compound I-1 or the free acid form is released from the composition at about 2 hours to about 4 hours (e.g., at about 2 hours) in the test; and (2) upon placement of the composition in an in vitro dissolution test comprising USP Dissolution Method at 100 rpm in approximately 1000 ml media at pH 7.4 at 37° C. using Type II Paddle, substantially all of the compound I-1 is released from the composition at about 1 hour to about 4 hours in the test.

In some embodiments, the in vitro dissolution test is substantially in accordance with Dissolution Study Procedure A below.

Dissolution Study Procedure A:
1) Set up the dissolution bath.
2) Ensure the temperature is at 37.0±0.5° C.
3) Offset placing one unit in each vessel to allow sufficient precision in sampling times.
4) Approximately 1 minute before each sampling time point prime the filter by withdrawing at least 2 ml of the medium and discarding the sample back into the vessel. Replace filter after each sampling time point.
5) At each sampling time point listed in the specifications, aliquot 1 ml and transfer into a vial. The amount of Compound I-1 released can be measured by HPLC.
6) Dissolution system is as follows.

| | |
|---|---|
| Medium: | 500 ml of HCl 0.1N for the acid stage |
| | At 2 hours add 250 ml of Stock Buffer solution, adjust to pH 6.0 with 5N HCl |
| | After 1 hour in pH 6.0, add 250 ml of Stock Buffer solution, adjust to pH 7.4 with 5N HCl |
| Bath Temperature: | 37.0 ± 0.5° C. |
| Apparatus: | II (Paddles) |
| Speed: | 100 rpm |

| | Time | Medium |
|---|---|---|
| Sampling times: | 2 hours | Acid stage |
| | 2.5 hours (0.5 hour in Buffer 1) | Buffer 1 Stage |
| | 3 hours (1 hour in Buffer 1) | |
| | 3.5 hours (0.5 hour in Buffer 2) | Buffer 2 Stage |
| | 4 hours (1 hour in Buffer 2) | |
| Sampling volume: | 1 ml | |
| Filter: | 0.45 μm GHP (change filter after each time point) | |

In some embodiments, Compound I-1 can also be included in a pharmaceutical composition comprising an aqueous solution. Aqueous solution of Compound I-1 suitable for the pharmaceutical composition includes any of those described herein. For example, the aqueous solution can include Compound I-1 in a concentration of at least 200 mg/ml. In some embodiments, a diluted aqueous solution of Compound I-1 in a concentration of about 0.1 mg/ml to about 200 mg/ml can also be used for the pharmaceutical composition.

In some embodiments, the active ingredient in the pharmaceutical composition can consist essentially of Compound I-1. For example, the pharmaceutical composition herein can include Compound I-1 along with its free acid form as the only active ingredient. Although Compound I-1 is a sodium salt, those skilled in the art would understand that certain free acid form may be present in the pharmaceutical composition, e.g., through equilibrium. In some embodiments, the pharmaceutical composition includes Compound I-1 along with its free acid form as the only active ingredient. Typically, the pharmaceutical composition is substantially free of compound I-1-Acid, for example, with an amount less than 5% by weight (e.g., less than 3%, less than 1%, less than 0.2%, less than 0.1%, less than 0.05%, or non-detectable). In some embodiments, the pharmaceutical composition is also substantially free of other salts of Compound I-1-Acid, for example, with an amount less than 5% by weight (e.g., less than 3%, less than 1%, less than 0.2%, less than 0.1%, less than 0.05%, or non-detectable). However, in some embodiments, the pharmaceutical composition herein can also include other active ingredients, for example, other compounds described herein or other active ingredients useful for treating the diseases or disorders described herein, such as inflammatory bowel diseases.

The pharmaceutical composition herein can include Compound I-1 in various amounts, for example, in an amount effective for treating the diseases or disorders described herein, such as inflammatory bowel diseases. Other suitable amounts are described herein.

Dosage Forms Comprising Other Compounds

Other compounds described herein, for example, any one or more of Compounds I-2 to I-10, can be formulated similarly to those described herein for Compound I-1. For example, such compounds can also be formulated in a solid dosage form (e.g., enteric coated tablet or capsule), or in a solution form (e.g., an aqueous solution).

For example, Compound I-2 can be included in any of the pharmaceutical compositions where Compound I-1 is indicated as suitable. As discussed herein, Compound I-2 similarly shows unexpectedly high kinetic solubility. In some embodiments, Compound I-2 can substitute Compound I-1 as the active ingredient in any of the pharmaceutical compositions where Compound I-1 is indicated as suitable (e.g, any of the solid or solution formulations described herein). In some embodiments, Form A2 of Compound I-2 is included in the pharmaceutical composition. In some embodiments, amorphous Compound I-2 is included in the pharmaceutical composition. In some embodiments, Compound I-2 in the pharmaceutical composition is in Form A2 and is substantially free from other solid state forms.

In some embodiments, the active ingredient in the pharmaceutical composition can consist essentially of Compound I-2. For example, the pharmaceutical composition herein can include Compound I-2 along with its free acid form as the only active ingredient. Although Compound I-2 is a potassium salt, those skilled in the art would understand that certain free acid form can be present in the pharmaceutical composition, e.g., through equilibrium. In some embodiments, the pharmaceutical composition includes Compound I-2 along with its free acid form as the only active ingredient. Typically, the pharmaceutical composition is substantially free of compound I-1-Acid, for example, with an amount less than 5% by weight (e.g., less than 3%, less than 1%, less than 0.2%, less than 0.1%, less than 0.05%, or non-detectable). In some embodiments, the pharmaceutical composition is also substantially free of other salts of Compound I-1-Acid, for example, with an amount less than 5% by weight (e.g., less than 3%, less than 1%, less than 0.2%, less than 0.1%, less than 0.05%, or non-detectable). However, in some embodiments, the pharmaceutical composition herein can also include other active ingredients, for example, other compounds described herein or other active ingredients useful for treating the diseases or disorders described herein, such as inflammatory bowel diseases.

The pharmaceutical composition herein can include Compound I-2 in various amounts, for example, in an amount effective for treating the diseases or disorders described herein, such as inflammatory bowel diseases. Other suitable amounts are described herein.

Certain Specific Formulations

In some embodiments, the present invention also provides certain specific formulations.

In some embodiments, the formulation includes a compound of Formula I in an enteric coated capsule. A typical example of such formulation is shown below:

Formulation 1: API in Coated Capsule (e.g., HPMC Capsule)

| Ingredient | % w/w |
| --- | --- |
| Active Ingredient: e.g., amorphous Compound I-1 | 70~100 (e.g., 99%) |
| Lubricant: e.g., Magnesium stearate | 0~30 (e.g., 1%) |
| HPMC Capsule Coating | |
| Enteric coating: e.g., Eudragit L/S100/Triethyl citrate/Talc/Ethanol | |

In some embodiments, the formulation includes enteric coated particles comprising a compound of Formula I, which can then be optionally encapsulated in a coated or uncoated capsule. A typical example of such formulation is shown below:

Formulation 2: Coated API in Capsule (e.g., HPMC Capsule)

| Ingredient | Typical % w/w | Preferred % w/w |
| --- | --- | --- |
| Active Ingredient: e.g., amorphous Compound I-1 | 50~90 | 60~80 (e.g., 60%) |
| Enteric coating: e.g., Eudragit L/S100/Triethyl citrate/Talc | 10~50 | 20~40 (e.g., 40) |
| Lubricant: e.g., Magnesium stearate | 0~10 | 0-1 (e.g., 0) |
| Others | 0~10 | 0-4 (e.g., 0) |

In some embodiments, the formulation includes granulated particles comprising a compound of Formula I, which can then be optionally encapsulated in a coated or uncoated capsule. A typical example of such formulation is shown below:

Formulation 3: Granulated Particles in Capsules (e.g., HPMC Capsule)

| Granulation (e.g., Fluid Bed) | |
| --- | --- |
| Ingredient | % w/w |
| Internal Phase | |
| Active Ingredient: e.g., amorphous Compound I-1 | 50~90 (e.g., 75) |
| Enteric coating: e.g., Eudragit S 100 | 10~30 (e.g., 20) |
| Stabilizer: e.g., HPMC (Pharmacoat 606) | 0~10 (e.g., 4) |
| Granulating liquid: Ethanol or other alcohols | |
| External Phase | |
| Lubricant: e.g., Magnesium stearate | 1~10 (e.g., 1) |

In some embodiments, the formulation includes a compound of Formula I in a tablet, such as a direct compression tablet, which can then be optionally enteric coated. A typical example of such formulation is shown below:

Formulation 4: Enteric Coated Tablets (e.g., Direct Compression/Enteric Dry Coating)

| Ingredient | % w/w |
| --- | --- |
| Active Ingredient: e.g., amorphous Compound I-1 | 20~60 (e.g., 40) |
| Enteric coating: e.g., Eudragit S 100 | 10~40 (e.g., 20) |
| Compression aid and/or disintegrant: e.g. microcrystalline cellulose, such as silicified microcrystalline cellulose | 20~49 (e.g., 39) |
| Lubricant: e.g., Magnesium stearate | 1~10 (e.g., 1) |

Methods of Treatment

The compound of Formula I (e.g., Formula I-B or I-C, or any one of Compounds I-1 to I-10) described herein is useful for treating various diseases or disorders discussed herein. As demonstrated earlier in U.S. application Ser. No. 15/205,853, published as US2017/0008924, the corresponding acid, Formula I-Acid, was shown to be efficacious in suppressing the expression and activity of inflammatory cytokines (e.g., IL-6) and chemokines and are able to remain at a sufficiently high concentration in a target tissue/cell while being less exposed to blood. Further, such compounds were shown to disrupt the formation of inflammatory signal transduction complex such as myeloid differentiation primary response gene 88 (MyD88) and/or receptor-interacting protein 1 (RIP1) that act in the downstream of signal pathway involving toll-like receptor 2/4 and IL-1β and can inhibit the activity of NF-κB by stabilizing of IκB. It was further demonstrated that the corresponding acid was effective in treating an inflammatory bowel disease; inhibiting formation of an inflammatory signal transduction complex MyD88, inhibiting formation of an inflammatory signal transduction complex mediated by Pellino-1, inhibiting formation of an inflammatory signal transduction complex Rip1; suppressing expression of at least one protein selected from the group consisting of G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1, and/or suppressing activity of NF-κB. In addition, it was shown that effective concentration of the acid compounds can be retained in a targeted tissue (e.g., small intestinal tissues, large intestinal tissues, appendix tissues) for a sufficient time. In various examples, U.S. application Ser. No. 15/205,853 also shows that Compound I-1-Acid was effective in treating various diseases such as inflammatory bowel diseases, multiple sclerosis, and septicemia. Those skilled in the art would expect that the salts of Compound I-1-Acid, such as Compound I-1, be similarly efficacious. In one example, formulations containing Compound I-1, when tested in a DSS induced colitis animal model similar to those described in U.S. application Ser. No. 15/205,853, were found to be efficacious with statistically significant improvement in total colitis scores.

Thus, in some embodiments, the present invention also provides a method of treating a disease or disorder mediated by formation of a Pellino-1 induced inflammatory signal transduction complex such as MyD88 and/or RIP1 in a subject in need thereof. In some embodiments, the method comprises administering to the subject a therapeutically effective amount of any of the compound of Formula I (e.g., Formula I-B or I-C, or any one of Compounds I-1 to I-10) described herein, such as the substantially pure compound of Formula I, or any of the pharmaceutical compositions described herein, such as an enteric coated composition comprising amorphous Compound I-1. In some embodiments, the compound of Formula I or the pharmaceutical composition described herein is administered to the subject via oral, nasal, pulmonary, rectal, buccal, vaginal, ocular, topical, parenteral or transdermal route. In some embodiments, the compound of Formula I (e.g., Formula I-B or I-C, or any one of Compounds I-1 to I-10) or the pharmaceutical composition described herein is administered to the subject in an amount sufficient to (1) inhibit formation of an inflammatory signal transduction complex MyD88; (2) inhibit formation of an inflammatory signal transduction complex mediated by Pellino-1; (3) inhibit formation of an inflammatory signal transduction complex Rip1; (4) suppress expression of at least one protein selected from the group consisting of G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1; and/or (5) suppress activity of NF-κB in the subject. In some embodiments, the disease or disorder is one or more of multiple sclerosis, psoriasis, sepsis, geographic atrophy, wet age-related macular disease, dry age-related macular disease, diabetic retinopathy, infectious lung diseases, bacterial pneumonia, viral pneumonia, diffuse large B-cell lymphoma, viral infection, autoimmune disease, obesity, blood cancer including lymphoma, and tumors in internal organs.

In some embodiments, the present invention also provides a method of treating an inflammatory bowel disease in a subject in need thereof. In some embodiments, the method comprises administering to the subject a therapeutically effective amount of any of the compound of Formula I (e.g., Formula I-B or I-C, or any one of Compounds I-1 to I-10) described herein, such as the substantially pure compound of Formula I, or any of the pharmaceutical compositions described herein, such as an enteric coated composition comprising amorphous Compound I-1. In some embodiments, the compound of Formula I or the pharmaceutical composition described herein is administered to the subject via the oral route or the rectal route. In some embodiments, the compound of Formula I (e.g., Formula I-B or I-C, or any one of Compounds I-1 to I-10) or the pharmaceutical composition described herein is administered to the subject in an amount sufficient to (1) inhibit formation of an inflammatory signal transduction complex MyD88; (2) inhibit formation of an inflammatory signal transduction complex mediated by Pellino-1; (3) inhibit formation of an inflammatory signal transduction complex Rip1; (4) suppress expression of at least one protein selected from the group consisting of G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1; and/or (5) suppress activity of NF-κB in the subject. In some embodiments, the inflammatory bowel disease is ulcerative colitis, Behcet's disease, and/or Crohn's disease.

In some embodiments, the prevent invention provides a method for treating geographic atrophy, wet age-related macular disease, dry age-related macular disease, and/or diabetic retinopathy in a subject in need thereof. In some embodiments, the method comprises administering to the subject a therapeutically effective amount of any of the compound of Formula I (e.g., Formula I-B or I-C, or any one of Compounds I-1 to I-10) described herein, such as the substantially pure compound of Formula I, or any of the pharmaceutical compositions described herein comprising amorphous Compound I-1. In some embodiments, the compound of Formula I or the pharmaceutical composition described herein is administered to the subject via oral, nasal, pulmonary, rectal, buccal, vaginal, ocular, topical, parenteral or transdermal route. In some embodiments, the compound of Formula I (e.g., Formula I-B or I-C, or any one of Compounds I-1 to I-10) or the pharmaceutical composition described herein is administered to the subject in an amount sufficient to (1) inhibit expression, in retinal pigment epithelium cells, of at least one protein selected from the group consisting of Nox-4, VEGF, VEGFR1, VEGFR2, Ang2, EPO and EPOR; (2) increase expression, in retinal pigment epithelium cells, of Ang 1, Tie2, or both.

In some embodiments, the prevent invention provides a method for treating alopecia in a subject in need thereof. In some embodiments, the method comprises administering to the subject a therapeutically effective amount of any of the compound of Formula I (e.g., Formula I-B or I-C, or any one of Compounds I-1 to I-10) described herein, such as the substantially pure compound of Formula I, or any of the pharmaceutical compositions described herein comprising amorphous Compound I-1. In some embodiments, the compound of Formula I or the pharmaceutical composition described herein is administered to the subject via oral, nasal, pulmonary, rectal, buccal, vaginal, ocular, topical, parenteral, or transdermal route. In some embodiments, the compound of Formula I (e.g., Formula I-B or I-C, or any one of Compounds I-1 to I-10) or the pharmaceutical composition described herein is administered to the subject in an amount sufficient to inhibit expression of IL-6 in scalp and hair follicles.

In some embodiments, the compound of Formula I or the pharmaceutical composition described herein can also be used to inhibit decomposition of IκB in inflammation signaling pathway mediated by MyD88 (myddosome complex) and/or RIP 1, thereby preventing NF-κB from being transported into nucleus of a cell, resulting in suppression of expression of cytokines and chemokines (e.g., G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1) and preventing inflammation reaction that could otherwise be caused by the expression thereof. Thus, in some embodiments, the present invention also provides a method of (1) inhibiting formation of an inflammatory signal transduction complex MyD88; (2) inhibiting formation of an inflammatory signal transduction complex mediated by Pellino-1; (3) inhibiting formation of an inflammatory signal transduction complex Rip1; (4) suppressing expression of at least one protein selected from the group consisting of G-CSF, IL-2, SCF, VEGF, CX3CL1, IGFBP5, IGFBP6, IL-1α, IL-1β, IL-6, IL-9, MCP-1, MIP-3α, IL12p40/70, MIG, TNF-α, and VCAM-1; and/or (5) suppressing activity of NF-κB in a cell. In some embodiments, the method comprises contacting the cell with an effective amount of any of the compound of Formula I (e.g., Formula I-B or I-C, or any one of Compounds I-1 to I-10) described herein, such as the substantially pure compound of Formula I, or any of the pharmaceutical compositions described herein, such as an enteric coated composition comprising amorphous Compound I-1.

The compound of Formula I or the pharmaceutical composition described herein can be used as the only intervention for the methods herein. However, in some embodiments, the compound of Formula I or the pharmaceutical composition described herein can also be used in conjunction with another therapy or medication for the respective method. For example, the compound of Formula I or the pharmaceutical composition described herein can be used in combination with another drug, either simultaneous, sequentially, or otherwise co-administered.

Definitions

Unless defined otherwise, all technical and scientific terms used herein have the meaning commonly understood by a person skilled in the art to which this disclosure belongs. The following references provide one of skill with a general definition of many of the terms used in this invention: The Cambridge Dictionary of Science and Technology (Walker ed., 1988); The Glossary of Genetics, 5th Ed., R. Rieger et. al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "or" is understood to be inclusive. Unless specifically stated or obvious from context, as used herein, the terms "a", "an", and "the" are understood to be singular or plural. For example, "a compound" includes mixtures of such compounds; "a carrier" includes mixtures of two or more carriers.

Unless specifically stated or obvious from context, as used herein, the term "about" is understood as within a range of normal tolerance in the art, for example within 2 standard deviations of the mean. In one embodiment, "about" can be understood as within 20% of the stated value. As used herein, "about" a specific value also includes the specific value, for example, about 10% includes 10%. Unless otherwise clear from context, all numerical values provided herein are modified by the term about.

The terms "active agent," "drug," and "pharmaceutical agent" are used interchangeably herein to refer to a chemical material or compound which, when administered to a subject by any means described herein (e.g., human or animal) induces a desired pharmacologic effect (e.g., such as a reduction of inflammation).

"Additive" as used herein refers to any additional components that can be added to the compositions and formulas described herein. For example, additives can include excipients (e.g., one or more excipients), antioxidants (e.g., one or more antioxidants), stabilizers (e.g., one or more stabilizers), preservatives (e.g., one or more preservatives), pH adjusting and/or buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents), viscosity-increasing agents (e.g., one or more viscosity-increasing agents), and the like, provided that the additional components are pharmaceutically acceptable for the particular condition to be treated. The additives can also include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-beta-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference. The additives described herein can be used in any suitable amounts.

As used herein, the term "administering" or "administration" is not limited to any particular route. For example, "administering" can include oral administration, administration as a suppository, topical administration, intravenous, parenteral, intraperitoneal, intramuscular, intralesional, intrathecal, intranasal, intravitreal or subcutaneous administration, or implantation of a slow-release device, e.g., a mini-osmotic pump, to a subject. In some embodiments, administration includes parenteral and transmucosal delivery, e.g., oral, nasal, pulmonary, rectal, buccal, vaginal, ocular, topical, or transdermal route.

As used herein, "antioxidants" include man-made or natural substances that can prevent or delay some types of cell damage and/or oxidation. Antioxidants are found in many foods, including fruits and vegetables. They are also available as dietary supplements. Exemplary antioxidants can include: β-carotene, Lutein, Lycopene, Selenium, Vitamin A, Vitamin C, and Vitamin E. Other antioxidants known to one of skill in the art can also be used. The antioxidants described herein can be used in any suitable amount.

By "co-administer" it is meant that a compound or composition described herein is administered at the same time, just prior to, or just after the administration of additional therapies or active agents or additives described herein. The compound or the composition of the disclosure can be administered alone or can be co-administered to the patient. Co-administration is meant to include simultaneous or sequential administration of the compound individually or in combination (more than one compound or agent). The preparations can also be combined, when desired, with other active substances.

As used herein, "concurrent administration" includes overlapping in duration at least in part. For example, when two agents (e.g., any of the agents or class of agents described herein that has bioactivity) are administered concurrently, their administration occurs within a certain desired time. The agents' administration can begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, an "effective amount" or "therapeutically effective amount" is that amount sufficient to affect a desired biological effect, such as beneficial results, including clinical results. As such, an "effective amount" depends upon the context in which it is being applied. An effective amount can vary according to factors known in the art, such as disease state, age, sex, and weight of the subject being treated. Several divided doses can be administered daily or the dose can be proportionally reduced as indicated by the exigencies of the therapeutic situation. In addition, the compositions/formulations of this disclosure can be administered as frequently as necessary to achieve a therapeutic amount.

The term, "gel" as used herein refers to a material which is not a readily flowable liquid and not a solid. Gels can be formed from naturally occurring or synthetic materials. The gels can be non-ordered to slightly ordered showing some birefringence, liquid crystal character. Gels can be administered topically.

The term "inflammatory bowel disease" as used herein has its usual medical meaning, and refers to a group of inflammatory conditions of the colon and/or small intestine. Exemplary inflammatory bowel diseases can include, but are not limited to, Crohn's disease, ulcerative colitis, Johne's disease, Behçet's syndrome, collagenous colitis, diversion colitis, indeterminate colitis, infective colitis, ischaemic colitis, lymphocytic colitis, and closely related diseases and disorders of the gastrointestinal tract.

The term "inhibit" or "suppress" as used herein, refer to the ability of a compound or composition to reduce, slow, halt or prevent activity of a particular biological process. For example, inhibiting an activity of a biological process can mean reducing the activity by at least about 10%, at least about 25%, at least about 30%, at least about 40%, at least about 50%, at least about 60%, at least about 70%, at least about 75%, at least about 80%, or at least about 100%.

"Jelly" according to the current disclosure is a class of gels, which are semisolid systems that consist of suspensions made up either small inorganic particles or large organic molecules interpenetrated by a liquid, in which the structural coherent matrix contains a high portion of liquid, usually water.

"Liquid" in the context of a dosage form as used herein refers to a dosage form consisting of a composition in its liquid state. In one embodiment, a "liquid" is pourable; and can flow and conform to its container at room temperature. Liquids display Newtonian or pseudoplastic flow behavior. In embodiments, a "semi-liquid" as used herein can have properties of both a liquid and another formulation (i.e., a suspension, an emulsion, a solution, a cream, a gel, a jelly, and the like).

"Myeloid differentiation primary response gene 88" or "MYD88" is a protein that, in humans, is encoded by the MYD88 gene. MyD88 plays a central role in the innate and adaptive immune response. This protein functions as an essential signal transducer in the interleukin-1 and Toll-like receptor signaling pathways. These pathways regulate that activation of numerous proinflammatory genes. The encoded protein consists of an N-terminal death domain and a C-terminal Toll-interleukin1 receptor domain.

As used herein, the term "ointment" refers to a highly viscous liquid or semi-liquid formulation that can be used for therapeutic treatment of a disease, syndrome, or condition (i.e., inflammatory bowel disease).

As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. For example, pharmaceutically acceptable carriers include sterile aqueous solutions or dispersions and sterile powders for the extemporaneous preparation of sterile topical solutions or dispersion. The use of such media and agents for pharmaceutically active substances is well known in the art. Use of any conventional media or agent, for example, in an ophthalmic composition, is contemplated, unless such media or agent is incompatible with the compound, composition, or formulation described herein.

"Pharmaceutical carriers" or "carriers" as used herein include pharmaceutically acceptable carriers, excipients, or stabilizers which are nontoxic to the cell or mammal being exposed thereto at the dosages and concentrations employed. In some embodiments, the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, polyethylene glycol (PEG), and Pluronics™. In some embodiments, a "pharmaceutically acceptable" ingredient (either an active ingredient or an excipient or carrier) means the ingredient is approved or approvable by a regulatory agency of the Federal or a state government in the United States or a corresponding agency in a non-U.S. country, or is listed in the U.S. Pharmacopoeia or other generally recognized pharmacopoeia, for use in animals, and more particularly, in humans.

The terms, "pH agent" or "buffering agent" as used herein refer to compounds or buffers useful as pH regulators. These include, but are not limited to, glycerol buffers, citrate buffers, borate buffers, acetate buffers, gluconate buffers, phosphate buffers, or citric acid-phosphate buffers can also be included. The pH agent or buffering agent can be used in any suitable amount.

The term, "preservative" as described herein refers to a substance or chemical that prevents undesirable chemical changes of the compound or compositions or formulas described herein. Suitable preservatives can include, for example, benzalkonium chloride, thimerosal, chlorobutanol, methyl paraben, propyl paraben, phenylethyl alcohol, edetate disodium sorbic acid, Onamer M Polyquat, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, sodium proprionate, and sodium perborate, and other agents known to those skilled in the art, or a combination thereof. The preservative can be used in any suitable amount.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 can comprise 1 to 10, 1 to 20, 1 to 30, and 1 to 40 in one direction, or 50 to 40, 50 to 30, 50 to 20, and 50 to 10 in the other direction.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Receptor interacting protein" or "RIP1" as used herein describes a protein kinase which is a crucial regulator of cell survival and death. RIP1 and RIP2 also bear a C-terminal domain belonging to the death domain superfamily, allowing recruitment to large protein complexes initiating different signaling pathways.

The "semisolid gel" according to the current disclosure is a semisolid. The semisolid formulation's apparent viscosity can increase with concentration.

As used herein, "sequential administration" includes administration of two agents (e.g., the compounds or compositions described herein) occurring separately on the same day or do not occur on a same day (e.g., occurs on consecutive days).

"Solution" according to the current disclosure can be a clear, homogeneous liquid dosage form that contains one or more chemical substances dissolved in a solvent or mixture of mutually miscible solvents. In one embodiment, a solution is a liquid preparation that contains one or more dissolved chemical substances in a suitable solvent or mixture of mutually miscible solvents. Because molecules of a drug substance in solution are uniformly dispersed, the use of solutions as dosage forms generally provides assurance of uniform dosage for administration and good accuracy of the dosage amount when the solution is diluted or otherwise mixed.

The term "solvent," as used herein, can be either aqueous or non-aqueous. Aqueous solvent can consist solely of water, or can consist of water plus one or more miscible solvents, and can contain dissolved solutes such as sugars, buffers, salts or other excipients. In some embodiments, non-aqueous solvents can include short-chain organic alcohols, such as, methanol, ethanol, propanol, short-chain ketones, such as acetone, and poly alcohols, such as glycerol. The solvent can be present in any suitable amount.

By "subject" or "patient" is meant either a human or animal, such as a mammal. "Subject" can include any animal, including horses, dogs, cats, pigs, goats, rabbits, hamsters, monkeys, guinea pigs, rats, mice, lizards, snakes, sheep, cattle, fish, and birds. A human subject can be referred to as a patient.

"Suspension" as used herein is a liquid dosage form that contains solid particles dispersed in a liquid vehicle.

As used herein, the term "syndrome" refers to a group of symptoms that consistently occur together or a condition characterized by a set of associated symptoms. A syndrome (e.g., inflammatory bowel syndrome) can be a set of medical signs and symptoms that are correlated with each other and often, are correlated with a specific disease. A disease on the other hand, can be a health condition that has a clearly defined reason behind it. A syndrome (from the Greek word meaning 'run together') however, can produce a number of symptoms without an identifiable cause. They can suggest the possibility of an underlying disease or even the chances of developing a disease.

The terms "treat," "treating" or "treatment," and other grammatical equivalents as used herein, include alleviating, abating, ameliorating, or preventing a disease, condition (e.g., inflammatory bowel disease) or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

As used herein, "viscosity" refers to a fluid's resistance to flow. Viscosity agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or a combination thereof.

EXAMPLES

The examples below are presented solely for illustration purposes and should not be construed in any way as limiting the scope of the present invention.

Example 1. General Methods

Certain starting materials and reagents are available through commercial sources and can be used as is. For example, Cremophor RH 40, Tween 80, meglumine are available through Sigma (Headquarter, Milwaukee).

The various starting materials, intermediates, and compounds of embodiments herein can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses.

X-ray analysis of the various solid forms herein can be performed using an X-ray Powder Diffractometer from Bruker, D8 advance. An exemplary method is shown below: Tube: Cu: K-Alpha ($\lambda$=1.54179 Å); Generator: Voltage: 40 kV; Current: 40 mA; Scan Scope: 4 to 40 deg; Sample rotation speed: 15 rpm; Scanning rate: 10 deg./min. The results are reported in 2θ±0.2°.

Differential Scanning Calorimetry (DSC) analysis can be run using TA Instruments' Q2000 model. In an exemplary method, the sample is heated from 30° C. to 300° C. at 10° C./min.

Thermal Gravimetric Analysis (TGA) analysis can be run using TA Instruments' Q5000IR model. In an exemplary method, the sample is heated from room temperature to 300° C. at 10° C./min.

HPLC analysis can be done using Agilent's system with Agilent's Zorbax SB-C8 (250*4.6 mm, 5 μm). An exemplary mobile phase includes acetonitrile (0.2% TFA) and water (0.2% TFA) with the gradient according to the following table and a flow rate of about 1 mL/minute:

| Time (min) | A: 0.2% TFA in water (v/v) | B: 0.2% TFA in ACN (v/v) |
| --- | --- | --- |
| 0.00 | 90 | 10 |
| 5.00 | 30 | 70 |
| 20.00 | 5 | 95 |
| 20.10 | 90 | 10 |
| 25 | 90 | 10 |

Different wavelengths can be used for detection, for example, at 220 nm. Those skilled in the art can adjust the HPLC methods when appropriate.

Example 2A. Preparation of Compound I-1

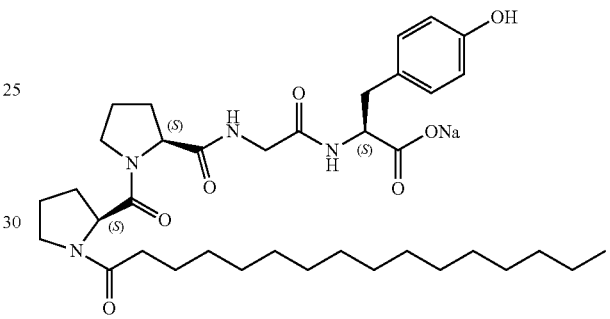

Compound I-1 was synthesized according to scheme 3 below:

(Scheme 3)

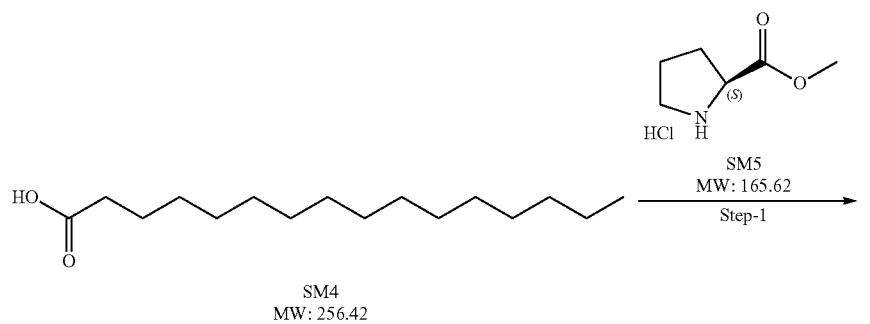

SM4
MW: 256.42

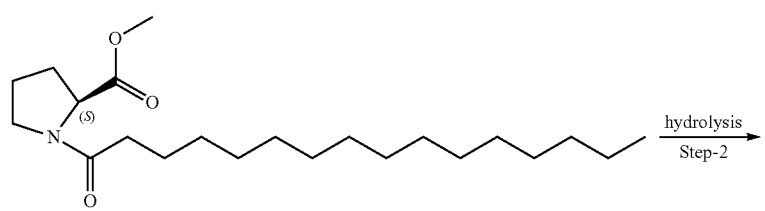

Compound-D
MW: 367.57

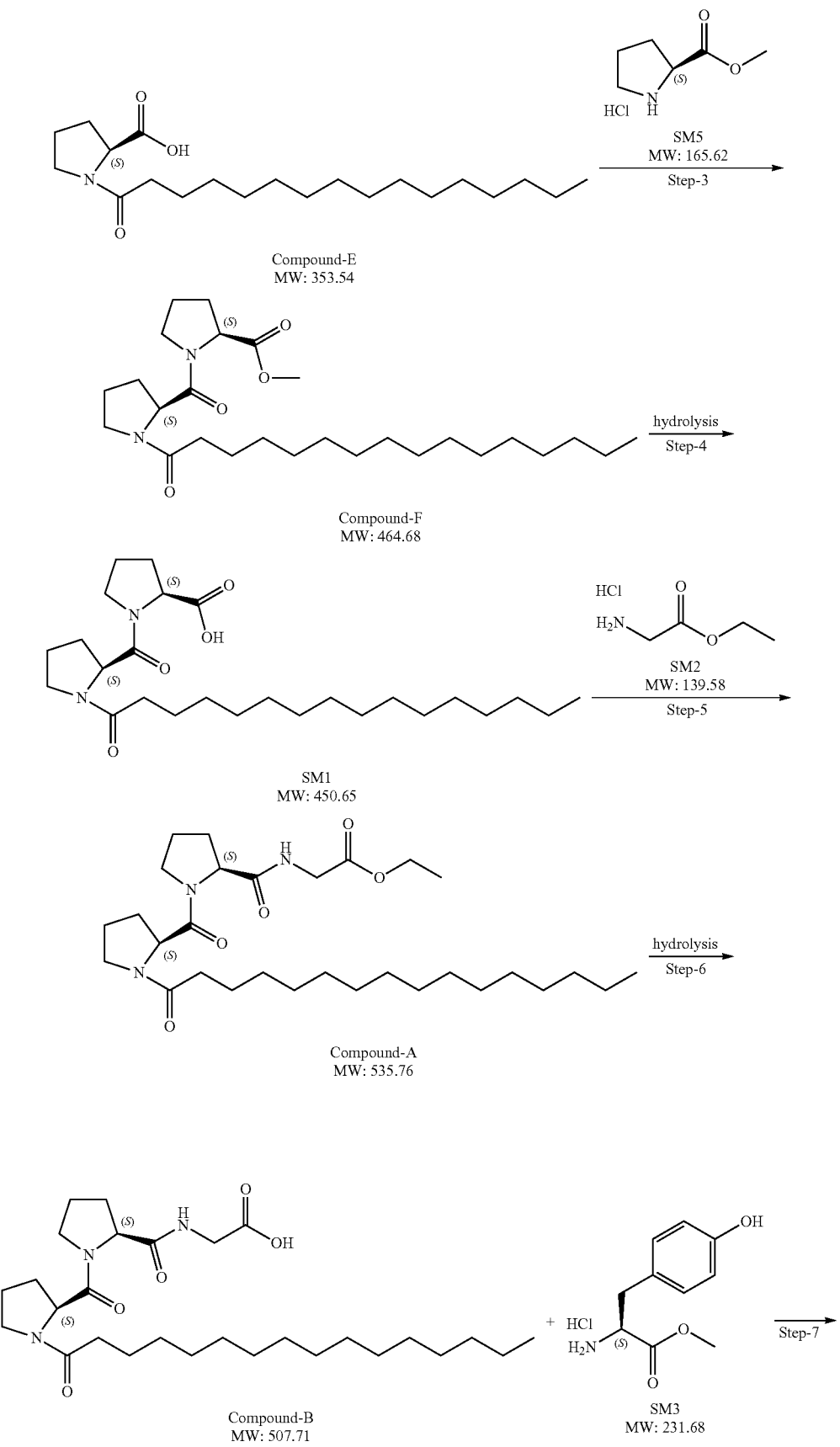

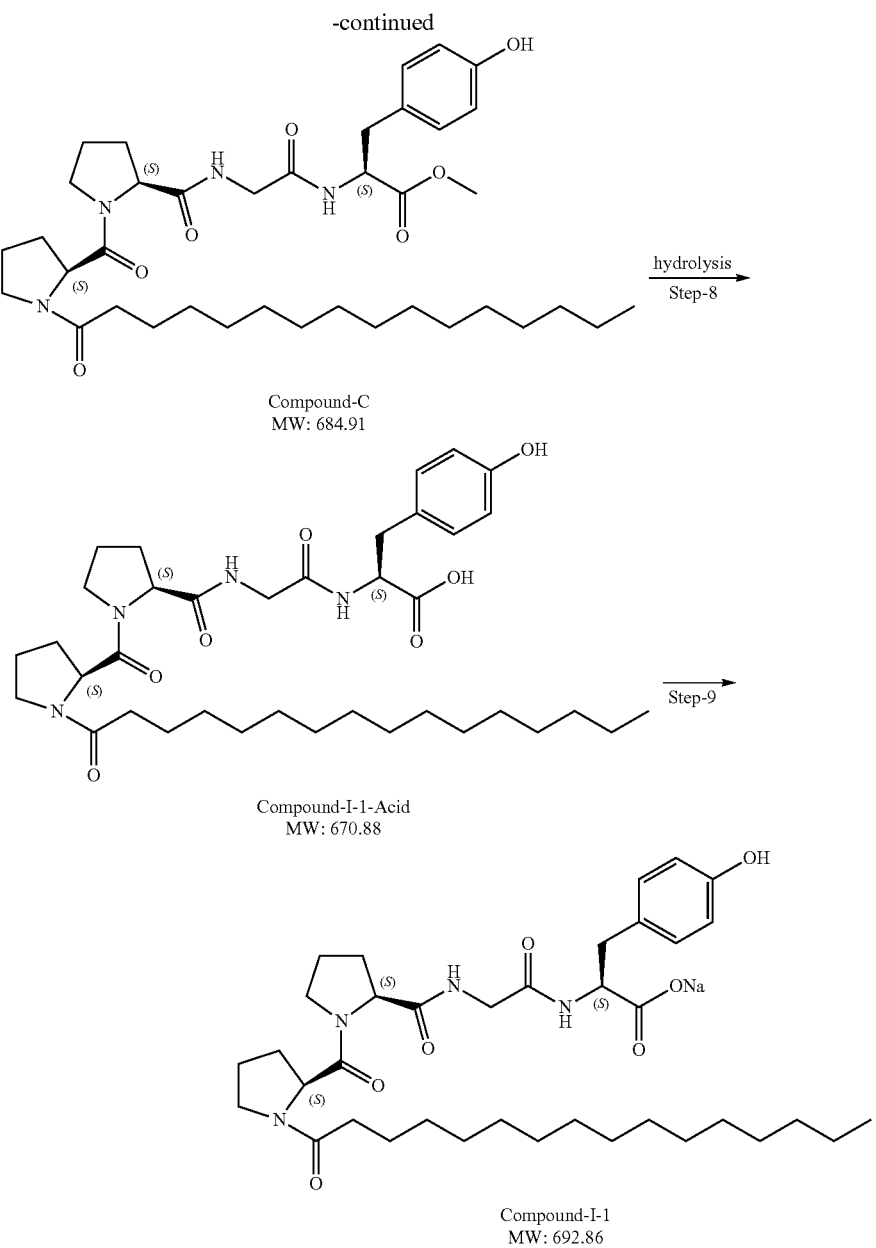

Compound I-1-Acid was prepared starting from SM4 and SM5 according to the procedure described in U.S. patent application Ser. No. 15/205,853, published as US2017/0008924, the content of which is herein incorporated by reference in its entirety.

Recrystallization of Intermediates

Several intermediates that led to Compound I-1-Acid in Scheme 3 were purified by re-crystallization. Specifically, Compound E was recrystallized in Ethyl Acetate (EtOAc) and n-heptane mixture. After hydrolysis of Compound-D with NaOH, an acid work-up was performed. EtOAc was then used to extract the acid Compound-E. After which, the EtOAc solution was washed with water and then brine to produce a crude product in EtOAc solution. n-Heptane was then added to the crude product solution, the amount of solvents was adjusted such that the ratio of EtOAc/n-Heptane is about 1:4 to 1:2 and the concentration of Compound E is about 1 g Compound-E/4-6 ml solvents. The EtOAc/Heptane mixture was then heated at 65-75° C. for about 0.5-2 hours before it was cooled to about 20-25° C. The solid formed was collected and dried to obtain crystalline Compound-E, with a purity of 97.8% by HPLC area.

Compound B was also recrystallized using EtOAc and n-Heptane. Here, the crude product in EtOAc solution (about 1 g Compound-B/4-6 ml solution) was heated at about 50-55° C. for about 0.5-2 hours. n-Heptane was then added to the EtOAc solution at about 50-55° C. The final ratio of EtOAc to n-Heptane was adjusted to about 1:4 to 1:2. The EtOAc/Heptane mixture was then maintained at 50-55° C. for about 0.5-1 hour, before it was cooled down to about 15-20° C. The solid formed was collected and dried to obtain crystalline Compound-B, with a purity of 97.7% by HPLC area.

Recrystallization of and Polymorphs of Compound I-1-Acid

Compound I-1-Acid was also recrystallized. Following hydrolysis of Compound C with NaOH, an acid work-up was performed. Crude Compound I-1-Acid was obtained as a solid, which was washed with water, acetone, and methyl tert-Butyl ether (MTBE), and dried. The dried Compound I-1-Acid was then recrystallized in acetic acid (about 1 g Compound I-1-Acid in about 6-10 mL acetic acid) by heating the mixture to 55-65° C. and maintained at the temperature for about 30-40 minutes. After the mixture was cooled to about 15-25° C., the crystals resulted was filtered, washed with MTBE, and dried to provide Compound I-1-Acid, with a purity of 97.8% by HPLC area.

A polymorph screening study on Compound I-1-Acid was also carried out, which identified Form 1. XRPD analysis of Form 1 is shown in FIG. 1A. FIG. 1B shows the TGA and DSC analysis of Compound I-1-Acid in Form 1. As shown in FIG. 1B, there were two endothermic peaks with onset at 145.4° C. and 172.2° C. About 0.25% weight loss from 25° C. to 120° C. and about 0.42% weight loss from 120° C. to 150° C. Form 1 was found to be non-hygroscopic (0.09% weight gain from 0-80% RH) by Dynamic Vapor Sorption System (DVS). After the DVS test, the XRPD pattern did not change.

Figure 2:
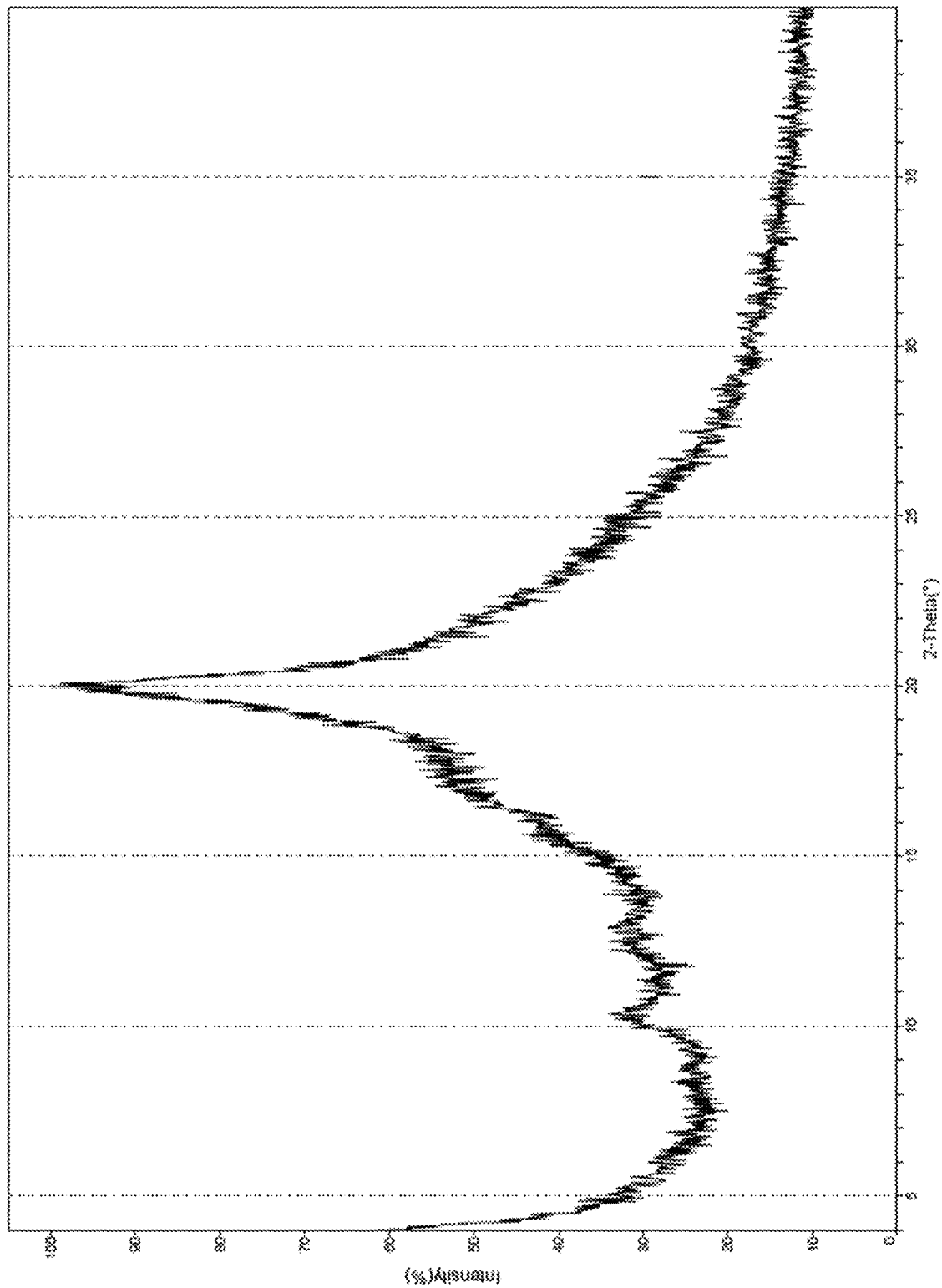

Compound I-1-Acid can also be prepared in an amorphous form. In particular, about 2 g Compound I-1-Acid was dissolved with 160 mL of THF:$H_2O$=1:1 at 40° C., and filtered through 0.45 μm nylon syringe filter into clean flask. Then the supernatant was freeze-dried to provide a white solid. The solid was shown to be in amorphous form by XRPD analysis (FIG. 2).

Amorphous Compound I-1-Acid can be readily converted into the crystalline Form 1. For example, when about 20 mg of amorphous of Compound I-1-Acid was suspended in methanol or ethanol and kept shaking at 40° C. for 3 days, the solid obtained (after filter and dry) has an XRPD pattern in accordance with Form 1.

Preparation of Compound I-1

Compound I-1-Acid was converted into Compound I-1 through treatment with a sodium base such as $Na_2CO_3$, $NaHCO_3$ or NaOH. In particular, Compound I-1-Acid (250 g, 1 eq.) and water (200 mL) were added into round bottom flask. $NaHCO_3$ (94 g, 3 eq.) in water was then added. The mixture was heated to 45-50° C., and then stirred for several hours. After cooling to 0-5° C., the solid resulted was filtered. The solid was then triturated with acetone. After filtering the mixture and drying, crystalline mono-sodium salt Compound I-1 was obtained, which can be further purified through recrystallization utilizing water or organic solvents.

Compound I-1 and water in a flask was heated to 50° C., until it was dissolved. This solution was then cooled to 0-5° C., stirred for several hours. After filtering the mixture and drying, further purified crystalline mono-sodium salt Compound I-1 was obtained, which can be further processed into amorphous form by organic solvent treatment.

Specifically, Compound I-1 (230.00 g) was dissolved in THF (1 L). The mixture was then concentrated at 40-50° C. under reduced pressure; this process was repeated for 3 times. This procedure was then repeated using MTBE (1 L) instead of THF for 3 times. After which, the solid obtained was dried at 40-50° C. for 2 hours under reduced pressure to provide amorphous Compound I-1 (203.00 g).

Example 2B. Alternative Preparation of Compound I-1

Alternatively, Compound I-1 can be prepared through a combination of solid phase peptide synthesis and solution phase synthesis.

Step 1. Preparation of Compound I-1-Acid (Bn)

1. Fmoc-Tyr(Bzl)-Gly-Pro-OH
2. Fmoc-pro-OH
3. $C_{15}H_{31}COOH$ $\xrightarrow{\text{2-CTC resin}}_{\substack{\text{DIC, HOBt} \\ \text{DMF, 15° C.}}}$

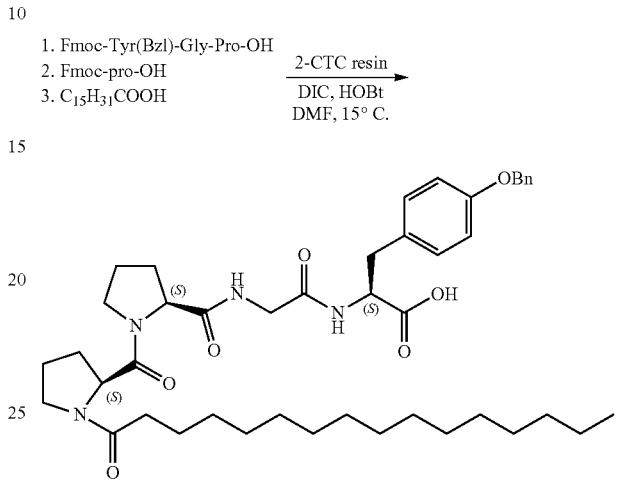

1. Fmoc-Tyr(Bzl)-Gly-Pro-OH (5 mmol) on resin, Fmoc-Pro-OH (2.53 g, 7.50 mmol) and HOBt (1.35 g, 10.0 mmol) were added to a 100 mL solid-phase reactor. To the mixture was added DMF (50 mL) and DIC (1.26 g, 10.0 mmol). The $N_2$ blowing was maintained for 2 h at 15° C. and the solvent was pumped away. The resin was washed with DMF (20 mL×5).

2. 20% piperidine in DMF (25 mL, v/v) was added to the reactor. $N_2$ blowing continued for 30 min and the solvent was removed. The resin was washed with DMF (50 mL×5).

3. Palmitic acid (1.92 g, 7.49 mmol) and HOBt (1.35 g, 9.99 mmol) were added to the reactor. To the mixture was added DMF (50 mL) and DIC (1.26 g, 9.99 mmol). The $N_2$ blowing was maintained for 2 h. The solvent was pumped away and the resin was washed with DMF (50 mL×3), EtOH (25 mL×2).

4. Another batch was prepared in the same way using same amount of starting material and reagent. The two batches were combined and the resin was transferred into a 100 mL flask and 20% $CF_3COOH$ in DCM (50 mL, v/v) was added to the flask. After stirring for 30 min, the mixture was filtered. This procedure was repeated one more time and the resin was washed with DCM (20 mL×2). The combined filtrate was concentrated under reduced pressure to afford the crude product (5.50 g). Part of the crude product (5.00 g) was used for next step directly. The other part of the crude product (500 mg) was purified by prep-HPLC (0.1% TFA as additive) to afford Compound I-1-Acid (Bn) (40 mg) as a white solid. $^1H$ NMR (400 MHz, $CD_3OD$) δ 0.92 (3H, t, J=6.8 Hz), 1.20-1.40 (24H, m), 1.52-1.66 (2H, m), 1.78-2.44 (10H, m), 2.89-3.21 (2H, m), 3.40-4.07 (6H, m), 4.32-4.71 (3H, m), 5.06 (2H, s), 6.94-6.98 (2H, m), 7.10-7.21 (2H, m), 7.27-7.49 (5H, m), 7.99-8.11 (1H, m). LC-MS Calculated 760.5, Found 761.4 $[M+H]^+$.

47

Step 2. Preparation of Compound I-1-Acid.

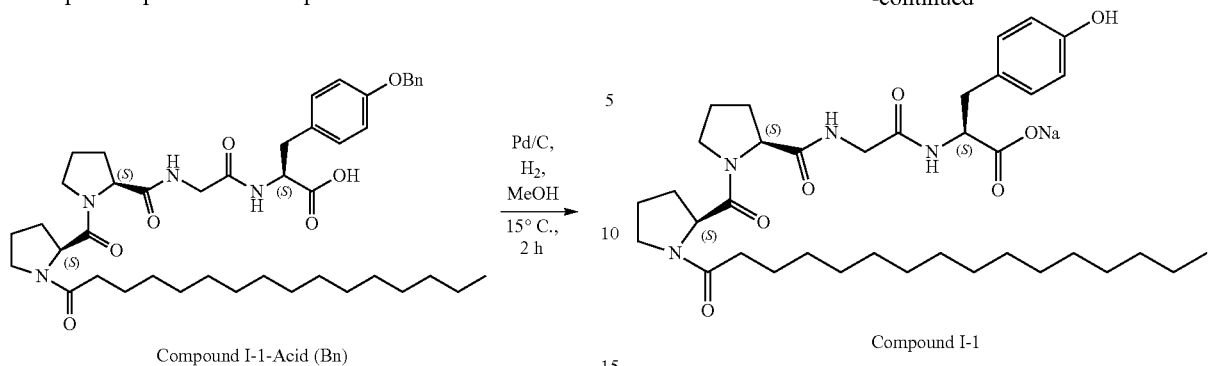

Compound I-1-Acid (Bn)

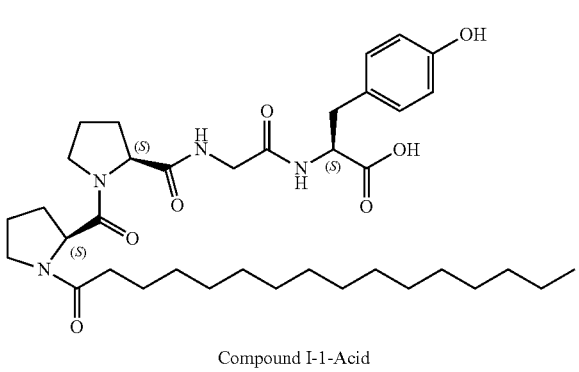

Compound I-1-Acid

To a solution of Compound I-1-Acid (Bn) (2.50 g, 3.29 mmol) in MeOH (20 mL) was added Pd/C (250 mg, 10% wet, 10% mol) under N₂. The suspension was purged with H₂ several times and stirred under H₂ (15 psi) at 15° C. for 2 h. The mixture was filtrated, concentrated under reduced pressure, to be purified by prep-HPLC to afford Compound I-1-Acid (400 mg) as a light red solid. $^1$H NMR (400 MHz, CD$_3$OD) δ 0.92 (3H, t, J=6.8 Hz), 1.20-1.40 (24H, m), 1.51-1.69 (2H, m), 1.79-2.47 (10H, m), 2.82-3.51 (2H, m), 3.38-4.11 (6H, m), 4.33-4.73 (3H, m), 6.63-6.76 (2H, m), 6.98-7.10 (2H, m), 7.83-8.16 (1H, m), 8.30-8.72 (1H, m).

Step 3. Preparation of Compound I-1

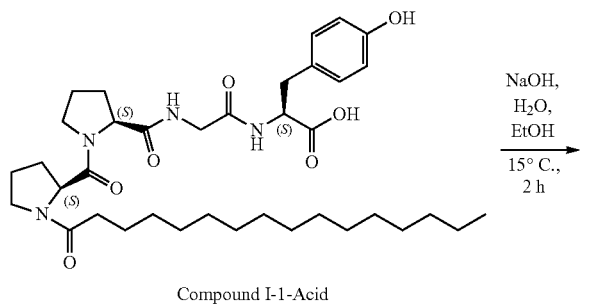

Compound I-1-Acid

48

-continued

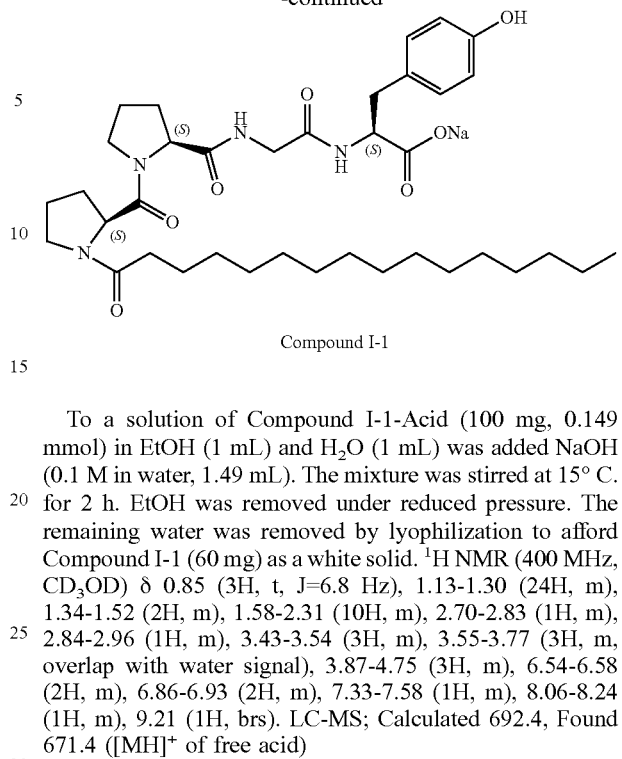

Compound I-1

To a solution of Compound I-1-Acid (100 mg, 0.149 mmol) in EtOH (1 mL) and H₂O (1 mL) was added NaOH (0.1 M in water, 1.49 mL). The mixture was stirred at 15° C. for 2 h. EtOH was removed under reduced pressure. The remaining water was removed by lyophilization to afford Compound I-1 (60 mg) as a white solid. $^1$H NMR (400 MHz, CD$_3$OD) δ 0.85 (3H, t, J=6.8 Hz), 1.13-1.30 (24H, m), 1.34-1.52 (2H, m), 1.58-2.31 (10H, m), 2.70-2.83 (1H, m), 2.84-2.96 (1H, m), 3.43-3.54 (3H, m), 3.55-3.77 (3H, m, overlap with water signal), 3.87-4.75 (3H, m), 6.54-6.58 (2H, m), 6.86-6.93 (2H, m), 7.33-7.58 (1H, m), 8.06-8.24 (1H, m), 9.21 (1H, brs). LC-MS; Calculated 692.4, Found 671.4 ([MH]⁺ of free acid)

Example 2C. Preparation of Compound I-2

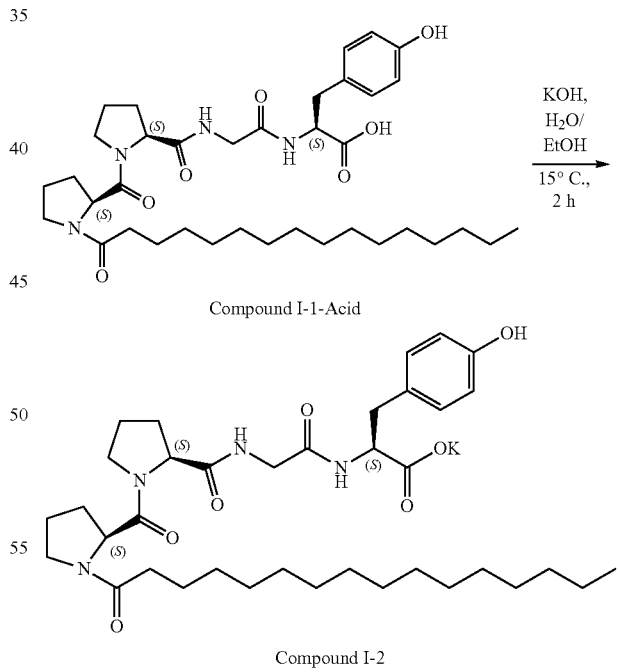

Compound I-2

Compound I-2 has been synthesized by following the virtually same procedure used for Compound I-1 shown in Example 2B. $^1$H NMR (400 MHz, CD$_3$OD) δ 0.86 (3H, t, J=6.8 Hz), 1.13-1.54 (26H, m), 1.58-2.31 (10H, m), 2.70-3.00 (2H, m), 3.21-3.62 (6H, m), 3.80-4.75 (3H, m), 6.53-6.59 (2H, m), 6.85-6.91 (2H, m), 7.26-7.47 (1H, m), 8.05-

8.25 (1H, m), 9.36 (1H, brs). LC-MS; Calculated 708.4, Found 671.4 ([MH]+ of free acid).

Example 2D. Preparation of Compound I-3

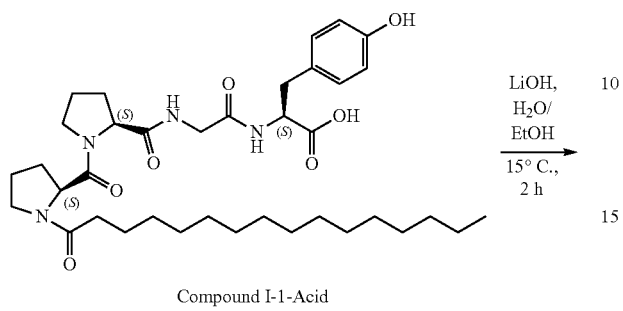

Compound I-1-Acid

Compound I-3

Compound I-3 has been synthesized by following the virtually same procedure used for Compound I-1 shown in Example 2B. $^1$H NMR (400 MHz, CD$_3$OD) δ 0.86 (3H, t, J=6.8 Hz), 1.09-1.51 (26H, m), 1.58-2.31 (10H, m), 2.70-3.04 (2H, m), 3.19-3.58 (6H, m), 3.87-4.75 (3H, m), 6.55-6.60 (2H, m), 6.86-6.94 (2H, m), 7.29-7.58 (1H, m), 7.90-8.25 (1H, m), 9.26 (1H, brs). LC-MS; Calculated 676.4, Found 671.4 ([MH]+ of free acid).

Example 2E. Preparation of Compound I-4

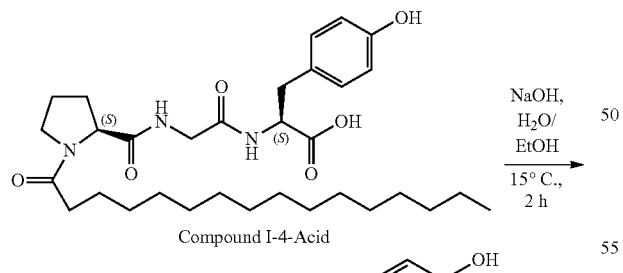

Compound I-4-Acid

Compound I-4

Compound I-4 has been synthesized by following the virtually same procedure used for Compound I-1 shown in Example 2B. $^1$H NMR (400 MHz, DMSO-d$_6$) δ 0.79-0.90 (3H, t, J=6.8 Hz), 1.15-1.33 (24H, m), 1.36-1.53 (2H, m), 1.74-2.05 (4H, m), 2.08-3.30 (2H, m), 2.73-2.85 (1H, m), 2.87-2.95 (1H, m), 3.41-3.71 (4H, m, overlap with water signal), 3.84-3.95 (1H, m), 4.20-4.37 (1H, m), 6.50-6.67 (2H, m), 6.81-7.02 (2H, m), 7.22-7.37 (1H, m), 8.13-8.38 (1H, m), 9.00-9.20 (1H, brs). LC-MS Calculated 579.4, Found 574.3 ([MH]+ of free acid).

Example 2F. Preparation of Compound I-5

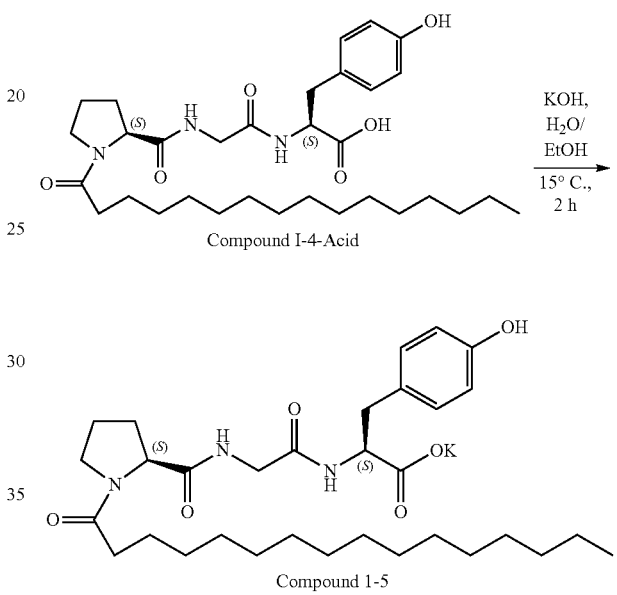

Compound I-4-Acid

Compound I-5

Compound I-5 has been synthesized by following the virtually same procedure used for Compound I-1 shown in Example 2B. $^1$H NMR (400 MHz, DMSO-d$_6$) δ 0.79-0.90 (3H, t, J=6.8 Hz), 1.15-1.33 (24H, m), 1.36-1.53 (2H, m), 1.74-2.05 (4H, m), 2.08-3.30 (2H, m), 2.73-2.85 (1H, m), 2.87-2.95 (1H, m), 3.41-3.71 (4H, m), 3.84-3.95 (1H, m), 4.20-4.37 (1H, m), 6.50-6.67 (2H, m), 6.81-7.02 (2H, m), 7.22-7.37 (1H, m), 8.13-8.38 (1H, m), 9.00-9.20 (1H, brs). LC-MS; Calculated 579.4, Found 574.3 ([MH]+ of free acid).

Example 2G. Preparation of Compound I-6

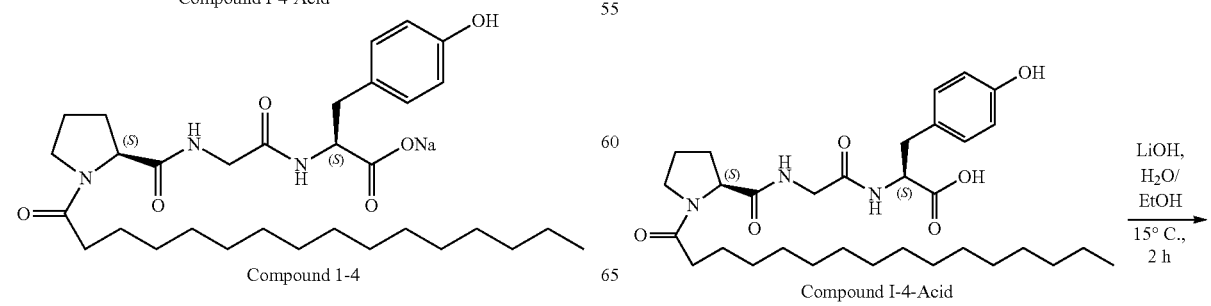

Compound I-4-Acid

-continued

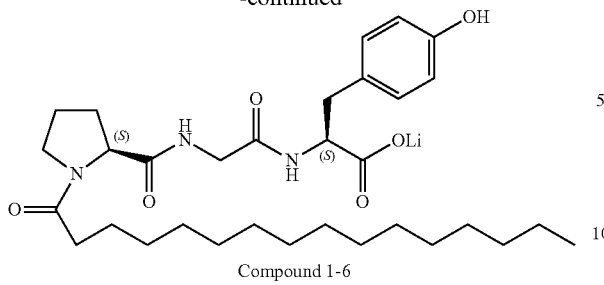

Compound I-6

Compound I-6 has been synthesized by following the virtually same procedure used for Compound I-1 shown in Example 2B. $^1$H NMR (400 MHz, DMSO-$d_6$) δ 0.79-0.90 (3H, t, J=6.8 Hz), 1.15-1.33 (24H, m), 1.36-1.53 (2H, m), 1.74-2.05 (4H, m), 2.08-3.30 (2H, m), 2.73-2.85 (1H, m), 2.87-2.95 (1H, m), 3.41-3.71 (4H, m, overlap with water signal), 3.84-3.95 (1H, m), 4.20-4.37 (1H, m), 6.50-6.67 (2H, m), 6.81-7.02 (2H, m), 7.22-7.37 (1H, m), 8.13-8.38 (1H, m), 9.00-9.20 (1H, brs). LC-MS Calculated 579.4, Found: 574.3 ([MH]$^+$ of free acid).

Example 2H. Preparation of Compound I-7

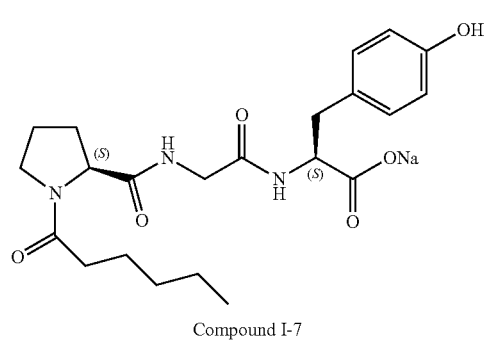

Compound I-7

Compound I-7 has been synthesized by following the virtually same procedure used for Compound I-1 shown in Example 2B. $^1$H NMR (400 MHz, DMSO-$d_6$) δ 0.80-0.98 (3H, m), 1.22-1.38 (4H, m), 1.46-1.54 (2H, m), 1.67-1.86 (1H, m), 1.92-2.30 (5H, m), 2.77-2.82 (1H, m), 2.86-2.94 (1H, m), 3.35-3.67 (4H, m), 3.85-3.94 (1H, m), 4.23-4.39 (1H, m), 6.41-6.49 (2H, m), 6.79-6.88 (2H, m), 6.93-7.23 (1H, brs), 8.18-8.45 (1H, m). LC-MS Calculated 455.2, Found 434.2 ([MH]$^+$ of free acid).

Example 2I. Preparation of Compound I-8

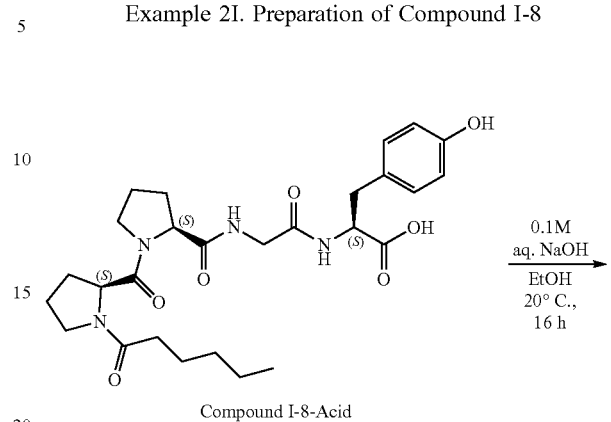

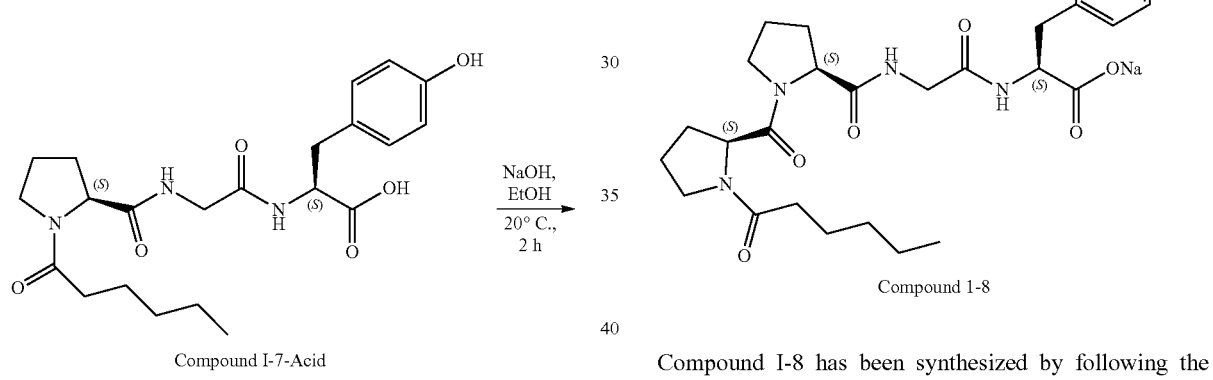

Compound I-8

Compound I-8 has been synthesized by following the virtually same procedure used for Compound I-1 shown in Example 2B. $^1$H NMR (400 MHz, DMSO-$d_6$) δ 0.84-0.86 (3H, m), 1.21-1.26 (4H, m), 1.43-1.47 (2H, m), 1.68-2.23 (10H, m), 2.74-2.94 (2H, m), 3.45-3.63 (6H, m), 4.01-4.70 (3H, m), 6.54-6.58 (2H, m), 6.86-6.91 (2H, m), 7.49 (1H, brs), 8.14 (1H, brs), 9.19 (1H, brs). LC-MS Calculated 530.2, Found: 531.2 ([MH]$^+$ of free acid).

Example 2J. Preparation of Compound I-9

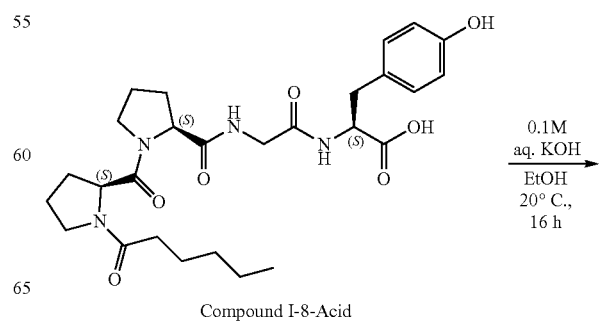

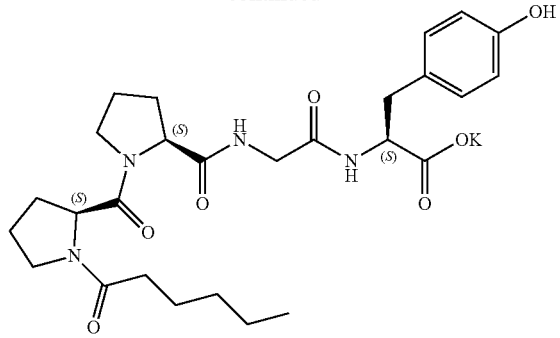
Compound I-9
Compound I-9 has been synthesized by following the virtually same procedure used for Compound I-1 shown in Example 2B. $^1$H NMR (400 MHz, DMSO-d$_6$) δ 0.81-0.86 (3H, m), 1.21-1.25 (4H, m), 1.43-1.48 (2H, m), 1.84-2.23 (10H, m), 2.75-2.93 (2H, m), 3.43-3.68 (6H, m), 4.02-4.70 (3H, m), 6.54-6.58 (2H, m), 6.87-6.92 (2H, m), 7.57 (1H, brs), 8.14 (1H, brs), 9.14 (1H, brs). LC-MS Calculated 530.2, Found: 531.3 ([MH]$^+$ of free acid).
Example 2K. Preparation of Compound I-10
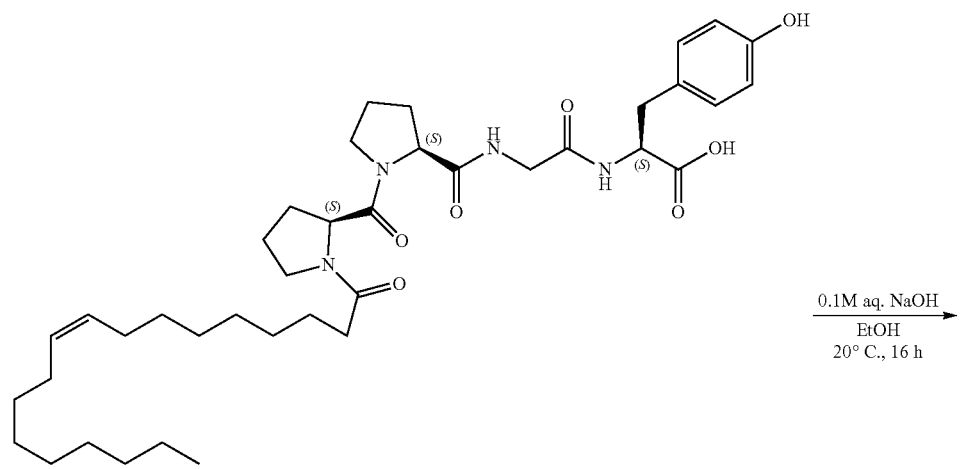
Compound I-10-Acid
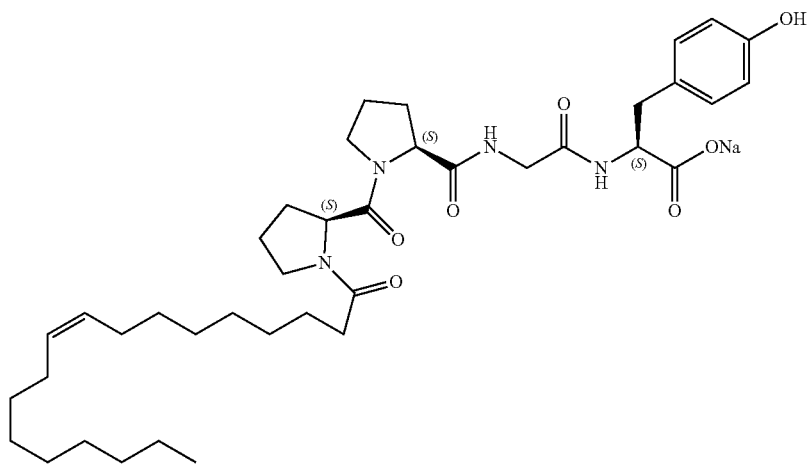
Compound I-10

Compound I-10 has been synthesized by following the virtually same procedure used for Compound I-1 shown in Example 2B. $^1$H NMR (400 MHz, DMSO-$d_6$) δ 0.85 (3H, t, J=6.8 Hz), 1.24-1.28 (20H, m), 1.42-1.46 (2H, m), 1.83-2.22 (12H, m), 2.78-2.92 (4H, m), 3.45-3.83 (7H, m), 4.27-4.67 (2H, m), 5.30-5.33 (2H, m), 6.52-6.54 (2H, m), 6.85-6.87 (2H, m), 7.29 (1H, brs), 8.09 (1H, brs), 9.05 (1H, brs). LC-MS Calculated 696.4, Found 697.4 ([MH]$^+$ of free acid).

Example 3. Polymorph Screening Studies on Compound I-1

As detailed below, an amorphous form and six crystalline polymorphs, Forms A-F, were identified in this study.

Amorphous Compound I-1

About 5 g of Compound I-1-Acid was completely dissolved with 170 mL of MeOH at 40° C. in a 250 mL glass bottle, and then appropriate NaOH solution, pre-dissolved in MeOH, was added into the free acid solution according at a 1:1 molar ratio. The mixture was then stirred at room temperature. When the solution turned into a clear solution after overnight stirring, the solution was dried by rotary evaporation to provide a white solid. The solid was dried under vacuum at 30° C. for 1 hour to provide an amorphous Compound I-1. XRPD analysis confirmed that this solid is in an amorphous form, see FIG. 3.

Form A of Compound I-1

Form A can be obtained through various methods. In one example, around 1 g of Compound I-1 was dissolved in 10 mL of water:acetone (1:6, v/v) at 60° C. The clear solution was then stored in a refrigerator at 5° C. for 1 hour to form a precipitate. Five milliliters of acetone was then added and stirred at 500 rpm for 4 days at room temperature. The precipitated solid was then collected and dried overnight at 30° C. in a vacuum oven and analyzed. FIG. 4A shows the XRPD analysis of Form A. Thermal investigations using TGA-MS and DSC (FIG. 4B) indicated that Form A had an initial small broad endotherm due to adsorbed water loss and then a larger endotherm at 107° C. due to about 3.1% of combined water loss. This was also supported by a heating experiment, in which it was found that Form A could be dehydrated and converted to amorphous after heating to 120° C. These results suggest that Form A is a hydrate form.

Form B of Compound I-1

Form B can also be obtained through various methods. In one example, Compound I-1 was dissolved in IPA-acetone (1:2) at 40° C. and the solution formed was then filtered through 0.45 μm nylon syringe filter into clean vessels. The solvents were then evaporated in the fume hood overnight to form a precipitate. The precipitated solid was then collected and dried in a vacuum oven at 30° C. overnight and analyzed. Form B displayed birefringence partly under the Polarized Light Microscopy (PLM), which indicated that it was a mixture form of amorphous and crystalline form. As shown in FIG. 5, TGA and DSC analysis shows that there were two weight losses of about 0.87% due to residual solvent or water and about 1.1% correspond to an endotherm peak at 110° C.

Form C of Compound I-1

Form C was obtained from heating Form A to 70° C. FIG. 6A shows an XRD analysis of Form C. Form C displayed birefringence and irregular shape with some agglomerations under the PLM. Thermal investigations (FIG. 6B) using DSC and TGA indicated that it had single endotherm at 101° C. due to 2.9% of water loss. Besides, Form C could be converted to Form A after storing at 25° C. for several days, indicated that it might be a metastable form.

Form D of Compound I-1

Form D was firstly observed in pH-solubility study of amorphous Compound I-1 in basic USP buffers, however, it was easily converted to Form A after vacuum drying at 25° C. overnight. FIG. 7 shows an XRPD analysis comparing Form A and Form D. FIG. 7 also shows that upon drying, Form D converted back to Form A.

Form E of Compound I-1

Form E was obtained from Form A or amorphous form stored at 60° C. and 40° C./75% RH for 2 weeks. It did have the similar data on the DSC/TGA data (FIG. 8B) with Form A and Form C, but with different XRPD pattern (see FIG. 8A).

Form F of Compound I-1

Form F was obtained from competitive study of Forms A and E when water activity is 0.3 at 40° C. About 10 mg of Form A and 10 mg of Form E were each weighted into saturated solutions of acetonitrile/water (98:2) with a water activity of 0.3. The suspensions were then slurried for 2 days or 6 days at 40° C. The solids obtained were dried in vacuum oven at 30° C. for overnight and then checked by XRPD (FIG. 9A). Thermal investigations (FIG. 9B) using TGA and DSC indicated that it had an initial larger broad endotherm with about 5.6% of weight loss and then a small endotherm at 110° C. Stabilities of Amorphous Compound I-1

Stabilities of amorphous Compound I-1 were also conducted according to ICH guideline. Compound I-1 was found to be stable under 25±2° C./60±5% RH and 40±2° C./75±5% RH for 6 months or more.

Based on XRPD analysis, no form transformation for amorphous Compound I-1 was observed at all the tested conditions except that it could be transferred into Form A at high humidity condition for 1 week. This shows that amorphous Compound I-1 can be storage stable at 40° C./75% RH with good protection from moisture, 60° C. and ambient, without polymorphic changes.

Example 4. Solubility of Compound I-1-Acid

This example shows an approximate solubility test of Compound I-1-Acid conducted in the different solvents at ambient laboratory temperature. The solubility test was conducted by manual dilution combined with visual observation. As shown below, Compound I-1-Acid has poor solubility (<1 mg/mL) in most organic solvents and water (Table 1).

TABLE 1

Results of approximate solubility at room temperature

| Solvents | Solubility (mg/mL) | Solvents | Solubility (mg/mL) |
| --- | --- | --- | --- |
| Methanol | 1-5 | Heptane | <1 |
| Ethanol | <1 | Cyclohexane | <1 |
| Isopropyl alcohol | <1 | 1,4-Dioxane | <1 |
| 1-butanol | <1 | DMSO | 10-25 |
| Acetonitrile | <1 | DMF | 1-5 |
| Acetone | <1 | N-methyl pyrrolidone | 1-5 |
| Methyl ethyl ketone | <1 | Water | <1 |
| Methyl isobutyl ketone | <1 | MeOH—$H_2O$ (1:1) | <1 |
| Ethyl acetate | <1 | MeOH—$H_2O$ (3:1) | <1 |
| Isopropyl acetate | <1 | EtOH—$H_2O$ (1:1) | <1 |
| Methyl t-butyl ether | <1 | EtOH—$H_2O$ (3:1) | <1 |
| Tetrahydrofuran | <1 | ACN—$H_2O$ (1:1) | <1 |
| 2-Methyl Tetrahydrofuran | <1 | Acetone-$H_2O$ (1:2) | <1 |
| Toluene | <1 | THF—$H_2O$ (1:1) | 1-5 |

Further investigation revealed that water solubility of Compound I-1-Acid is less than 2 µg/mL.

Example 5. Solubility Studies on Compound I-1

In this Example, approximate solubility tests of Compound I-1 (amorphous) were conducted in the different solvents at ambient laboratory temperature. The solubility was also tested by manual dilution combined with visual observation. In particular, a known amount of Compound I-1 was weighed and added to a vial. A known amount of solvent was gradually added to the vial with constant stirring. The solvent addition was kept at a very slow rate to minimize any excess solvent beyond what is needed to fully dissolve the solids. In order to cross-check the solubility, a small amount of Compound I-1 was added to the vial to confirm that the solution became turbid. The results were shown in Table 2.

TABLE 2

Solubility of Compound I-1 (Amorphous)

| Solvents | Solubility (mg/mL) | Solvents | Solubility (mg/mL) |
| --- | --- | --- | --- |
| Methanol | >100 | Heptane | <1 |
| Ethanol | 50-100 | Cyclohexane | <1 |
| Isopropyl alcohol | 50-100 | 1,4-Dioxane | 33.3-50 |
| 1-butanol | 50-100 | DMSO | 50-100 |
| Acetonitrile | <1 | DMF | 20-33.3 |
| Acetone | <1 | N-methyl pyrrolidone | 50-100 |
| Methyl ethyl ketone | 3.3-5.0 | Water | >100 |
| Methyl isobutyl ketone | 1.2-1.4 | Methanol:H$_2$O (1:1) | >100 |
| Ethyl acetate | <1 | Methanol:H$_2$O (3:1) | >100 |
| Isopropyl acetate | <1 | Ethanol:H$_2$O (1:1) | 50-100 |
| Methyl t-butyl ether | <1 | Ethanol:H$_2$O (3:1) | 50-100 |
| Tetrahydrofuran | >100 | Acetonitrile:H$_2$O (1:1) | 50-100 |
| 2-Methyl Tetrahydrofuran | >100 | Acetone:H$_2$O (1:2) | 50-100 |
| Toluene | 50-100 | Tetrahydrofuran:H$_2$O (1:1) | 50-100 |

Solubility Comparisons of Amorphous, Forms A and E of Compound I-1

The solubility of amorphous, Form A or E of Compound I-1 in water was further studied. Specifically, about 250 mg Compound I-1 in amorphous, Forms A and E were each suspended in a 2 mL HPLC vial with 0.9 mL of water. Each suspension was then shaken at 25° C. under 1000 rpm. The suspensions were analyzed at 1 h and 24 h. In particular, at either the 1 h or 24 h time point, the slurries were centrifuged and analyzed by HPLC. The pH values of the mother liquors were measured, and the residues were characterized by XRPD.

This study shows that the amorphous form could reach higher solubility (>200 mg/mL) than Forms A and E (about 180 mg/mL) in water at 1 hour at 25° C., although the solubility of the amorphous form dropped thereafter to about 180 mg/mL at about 24 hours. See Table 3 below.

TABLE 3

Results of solubility of Compound I-1 in amorphous form, Forms A and E

| Compound I-1 | Time point (hours) | Solubility at 25° C. (mg/mL) | Final pH | XRPD pattern (wet) |
| --- | --- | --- | --- | --- |
| Amorphous | 1 | 239.1 | 9.05 | D |
|  | 24 | 180.1 | 9.03 | Mostly D |
| Form A | 1 | 184.5 | 8.91 | A + D |
|  | 24 | 208.6 | 8.70 | — |

TABLE 3-continued

Results of solubility of Compound I-1 in amorphous form, Forms A and E

| Compound I-1 | Time point (hours) | Solubility at 25° C. (mg/mL) | Final pH | XRPD pattern (wet) |
| --- | --- | --- | --- | --- |
| Form E | 1 | 171.3 | 9.08 | A + D |
|  | 24 | 199.4 | 8.70 | — |

The above shows that the kinetic solubility of Compound I-1 (sodium salt) can be surprisingly very high (about 200 mg/mL) at 25° C. Further research revealed that potassium salt, Compound I-2, has similar solubility as that of sodium salt, about 166-200 mg/mL kinetic solubility at 25° C.

Example 6. Solubility Enhancement of Compound I-1

Compound I-1 can be formulated with a variety of pharmaceutically acceptable excipients. In this example, the aqueous solubility of Compound I-1 in the presence of various excipients was studied.

Specifically, about 50 mg of Compound I-1 was weighed into a 1.5-mL HPLC vial, and 0.2 mL of different media was then added to each vial. The mixtures were shaken at 25° C. under 700 rpm. After 24 hours of shaking, the slurries were centrifuged twice and analyzed. The supernatant was analyzed by HPLC. The solubility results are shown in Table 4.

TABLE 4

Solubility of Compound I-1 in water with excipients

| Excipients | Contents in Water (w/v %) | Solubility (mg/mL) |
| --- | --- | --- |
| Meglumine | 1% | 190 |
|  | 2% | >250* |
|  | 5% | >250* |
|  | 10% | >270 |
| Cremophor RH 40 | 1% | 231 |
|  | 10% | 209 |
| TWEEN 80 | 1% | 215 |
|  | 10% | 198 |
| HPβCD | 5% | <250* |
| HPMC E3 | 5% | <250* |
| Meglumine:Cremophor RH 40 (1:1, w/w) | 10% | >250* |

*The data is based on approximate solubility by visual observation, not by HPLC analysis.

Stability of Compound I-1 in Meglumine Solutions

As meglumine showed promise in enhancing solubility of Compound I-1, physical stability of Compound I-1 in meglumine solutions was tested. This study shows (Table 5) that Compound I-1 formulation at 200 mg/mL concentration in water with 3%, 4%, or 5% meglumine, or more, demonstrated good physical stability when stored at 25° C., even after storing for 13 days. This result indicates that addition of 3% meglumine would be useful for a solution formulation, especially when the concentration of Compound I-1 is high. In contrast, an aqueous formulation with a concentration of Compound I-1 of 200 mg/mL, without meglumine, started forming precipitates after storing 1 day at 25° C. The stability of solutions of Compound I-1 was found to be temperature sensitive. When stored at 5° C., solutions of Compound I-1 were not physically stable even at a 5 mg/mL solution formulation with different concentrations of meglumine (2-5%).

TABLE 5

Stability of solutions with different Meglumine concentrations (weight to volume) at 25° C.

| Compound | Vehicle | Concentration, mg/mL | Appearance |
|---|---|---|---|
| Compound I-1 | Water | About 200 | Precipitation after 1 day |
| | Meglumine, 2% | 200 | Precipitation after 2 days |
| | Meglumine, 2% | 250 | Precipitation after 1 day |
| | Meglumine, 3% | 200 | No precipitation until 3 weeks |
| | Meglumine, 4% | 200 | No precipitation until 3 weeks |
| | Meglumine, 5% | 200 | No precipitation until 3 weeks |
| | Meglumine, 5% | 250 | Precipitation after 5 days |
| | Meglumine, 5% | 300 | Precipitation after 3 days |

Example 7. Compound I-2: Preparation and Solubility Studies

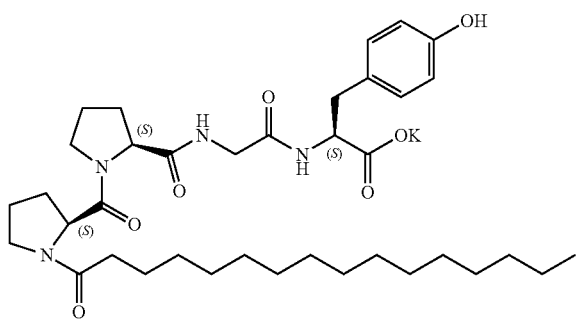

This Example shows a non-limiting manufacturing procedure of potassium salt of Compound I-1-Acid.

In particular, 5 g of Compound I-1-Acid was completely dissolved with 200 mL of methanol at 40° C. in a 500 mL flask. Then, 14 mL of KOH solution, which was pre-dissolved in methanol (38.46 mg/mL), was added into the solution of Compound I-1-Acid. The mixture was stirred for 3 hours at room temperature until it became a clear solution. The solvent was then removed by rotary evaporator to provide mono-potassium salt (Compound I-2) as a white solid.

Amorphous Compound I-2 could be obtained through the treatment of anhydrous THF at 50° C. after a dissolution and evaporation process.

Polymorphs of Compound I-2

Compound I-2 can have different crystalline forms. Two different polymorphs, Forms A2 and B2 were identified. Form A2 can be prepared as follows. Specifically, the white solid of Compound I-2 obtained above was dissolved in 30 mL THF:water (95:5, v/v). MTBE (200 mL) was then added slowly, which resulted in precipitation of a lot of white solid. The suspension was then allowed to be stirred at room temperature overnight. After which, the solid was filtered, washed with THF:water:MTBE=7.5:1:53 (25 mL*3) to remove excess KOH, and then dried under vacuum at 25° C. overnight to provide Form A2. XRPD analysis of Form A2 is shown in FIG. 10A. Thermal investigations (FIG. 10B) using TGA-MS and DSC indicates that Form A2 had two endotherm peaks at 82° C. and 92° C. due to about 6.0% of water loss. Based on the DVS isotherm curve, Form A2 was hygroscopic (about 8% water absorption), but no form change was not observed after the DVS study.

Further study also showed that Form A2 had good crystalline stability and was stable when stored at three different conditions (25° C./92.5% RH, 40° C./75% RH, 60° C.), even for 25 days.

Form B2 of Compound I-2 can be prepared as follows. About 300 mg of Compound I-2 was dissolved with 3 mL of acetone:water (1:1) at 50° C. in an 8 mL glass vial. And the solution was filtered into a clear vial, then evaporated in the fume hood to precipitate solid. XRPD indicates a crystalline form different from Form A2. Form B2 appears to be a metastable form and is a poor crystalline form.

Solubility Studies of Compound I-2

The solubility of Compound I-2 (amorphous) at room temperature was tested using a method similar to those described in Examples 4 and 5. The solubility test results are described in Table 6.

TABLE 6

Solubility of Compound I-2 (amorphous) at room temperature

| Solvents | Solubility (mg/mL) | Solvents | Solubility (mg/mL) |
|---|---|---|---|
| Methanol | >100 | Heptane | <1 |
| Ethanol | 50-100 | Cyclohexane | <1 |
| Isopropyl alcohol | 1-5 | 1,4-Dioxane | <1 |
| 1-butanol | 1-5 | DMSO | 50-100 |
| Acetonitrile | <1 | DMF | 50-100 |
| Acetone | <1 | N-methyl pyrrolidone | 50-100 |
| Methyl ethyl ketone | <1 | Water | >100 |
| Methyl isobutyl ketone | <1 | Methanol:$H_2O$ (95:5) | >100 |
| Ethyl acetate | <1 | Methanol:$H_2O$ (90:10) | >100 |
| Isopropyl acetate | <1 | Ethanol:$H_2O$ (95:5) | 25-50 |
| Methyl t-butyl ether | <1 | Ethanol:$H_2O$ (90:10) | 25-50 |
| Tetrahydrofuran | <1 | Acetonitrile:$H_2O$ (95:5) | <1 |
| 2-Methyl Tetrahydrofuran | <1 | Acetone: $H_2O$ (97:3) | <1 |
| Toluene | <1 | Tetrahydrofuran:$H_2O$ (95:5) | 50-100 |

Example 8. Salt Selection Studies of Compound I-1-Acid

In search for salt or co-crystal with extraordinary solubility in water, a salt screening was performed in ethanol, IPA, 90% IPA, acetonitrile, tetrahydrofuran (THF) and PH 12 solution (prepared using NaOH). Common techniques like evaporation and slurry were used for the screening process and non-limiting reagents for co-crystals/salts include Acetic acid, 4-Aminosalicylic acid, Ammonium chloride, Benzensulfonic acid, Caffeine, calcium chloride, Calcium hydroxide, 1R-(−)-10-Camphorsulfonic acid, 1S-(+)-10-Camphorsulfonic acid, Citric acid, Copper sulfate, 1,2-Ethane Disulfonic acid, Ethanesulfonic acid, Hydrochloric acid, 4-Hydroxybenzoic acid, 1-Hydroxy-2-naphthoic acid, Magnesium sulfate, Methanesulfonic acid, 1,5-Naphthalene disulfonic acid, 2-Naphthalenesulfonic acid, Nicotinamide, Sodium hydroxide, Sodium carbonate, Sodium hydrogen carbonate, Lithium hydroxide, Lithium carbonate, Lithium hydrogen carbonate, Phosphoric acid, p-Toluenesulfonic acid, Silver nitrate, Sodium sulfate, Sucrose, Sulphuric acid, Trifluoroacetic acid, Zinc oxide, Zinc sulfate, Adipic acid, Aspartic acid, Fumaric acid, Gallic acid, Gluconic acid, Glutamic acid, Glycine, Glycolic acid, Lactic acid, Leucine, Maleic acid, Malic acid, Malonic acid, Mandelic acid, Mucic acid, Oxalic acid, Pivalic acid, Salicylic acid, Succinic acid, Tartaric acid, Potassium sulfate, Meglumine, Arginine, Lysine, Potassium hydroxide, Potassium carbonate, Potassium hydrogen carbonate. A few examples are shown in Table 7.

TABLE 7

Examples of preparing different salt forms of Compound I-1-Acid

| No. | Reagents | Crystallization Methods | Preparation Methods |
|---|---|---|---|
| 1 | NaOH | Anti-solvent crystallization | Crystalline product was obtained by adding ethyl acetate to a solution of Compound I-1-Acid and NaOH (1:1) in 90% IPA solution and allowing it to stand at room temperature for a few days. |
| 2 | Ca(OH)$_2$ | Evaporation or anti-solvent crystallization | (a) Take Compound I-1-Acid and Ca(OH)$_2$ in the molar ratio of 1:1 in ethanol or IPA, stir the solution until it becomes transparent and then evaporate the solution at room temperature to obtain the desired form. (b) Take Compound I-1-Acid and Ca(OH)$_2$ in the molar ratio of 1:1 in ethanol or IPA, stir the solution until it becomes transparent and then add acetonitrile as an anti-solvent to the solution at room temperature to obtain the desired form. |
| 3 | Na$_2$SO$_4$ | Evaporation method | 25 mg of Compound I-1-Acid was dissolved with Na$_2$SO$_4$ in 1:1 molar ratio in 5 mL PH 12 solution to form a clear solution. The clear solution was evaporated at RT to obtain the desired product |
| 4 | CaCl$_2$ | Slurry | (a) 100 mg of Compound I-1-Acid was added to 10 mL of pH 12 solution with CaCl$_2$ in 1:1 molar ratio. The solution was stirred for 1-2 days to obtain a desired product. (b) To obtain anhydrous form, resulted crystals were heated on a hot plate at 70° C. for 10-15 min. |
| 5 | MgSO$_4$ | Slurry | (a) 100 mg of Compound I-1-Acid was added to 10 mL of pH 12 solution with MgSO$_4$ in 1:1 molar ratio. The solution was stirred for 1-2 days to obtain a desired product. (b) To obtain anhydrous form, resulted crystals were heated on a hot plate at 70° C. for 10-15 min. |
| 6 | ZnSO$_4$ | Slurry | (a) 100 mg of Compound I-1-Acid was added to 10 mL of pH 12 solution with ZnSO$_4$ in 1:1 molar ratio. The solution was stirred for 1-2 days to obtain a desired product. (b) To obtain anhydrous form, resulted crystals were heated on a hot plate at 70° C. for 10-15 min. |
| 7 | ZnO | Slurry | Take Compound I-1-Acid and ZnO in the molar ratio 1:1 and slurry in PH 12 solution (prepared using NaOH) for 4 days to obtain the desired product. |
| 8 | Glycine | Evaporation | 25 mg Compound I-1-Acid was dissolved with glycine in 1:1 molar ratio in 5 mL of PH 12 solution to form a clear solution. The clear solution was evaporated at RT to obtain the desired product. |

Formulation Example 1. Formulation A, Compound I-1 in Enteric Coated Capsules

Amorphous Compound I-1 was used for different formulations in this example.

In Formulation A, amorphous Compound I-1 was mixed with magnesium stearate in a weight ratio of about 99:1 (Compound I-1 to magnesium stearate). The mixture was then encapsulated in an enteric coated HPMC capsule. The enteric coating included a mixture of Eudragit L/S 100, triethyl citrate, talc, and ethanol.

This enteric coated capsule formulation was tested for stability and dissolution. It was found that after storing at 40° C. for 1 month at 75% RH, the formulation showed no deterioration of the amount of Compound I-1, no increase in the amount of Compound I-1 related impurities, and no change of amorphous Compound I-1 into a crystalline form (see FIG. 12), although water content of the formulation was slightly increased. Thus, this formulation can be storage stable.

An in vitro dissolution test was carried out for Formulation A following Dissolution Study Procedure A. The results showed that after 2 hours in 0.1 N HCl solution, all capsules were intact. And after placing the capsules in dissolution media with pH adjusted to 7.4 with Na$_3$PO$_4$ buffer, for all tested capsules, essentially all Compound I-1 was released within 2 hours, and for some capsules, essentially all Compound I-1 was released within 1 hour. Substantially similar results were obtained when Formulation A was tested around the time it was prepared or after storage at 40° C. for 1 month at 75% RH. Thus, Formulation A can delay release of Compound I-1 until it reaches a non-acidic environment, which can then quickly release substantially all Compound I-1. This characteristic will be beneficial for treating diseases such as inflammatory bowel diseases described herein, where delivery of active ingredients such as Compound I-1 to lower gastrointestinal tract or colon is desired.

Formulation Example 2. Formulation B, Coated API in Capsule

Amorphous Compound I-1 was used for different formulations in this example.

In Formulation B, amorphous Compound I-1 was enteric coated with an enteric coating which included a mixture of Eudragit L/S 100, triethyl citrate, talc, and ethanol. The weight ratio of Compound I-1 to the enteric coating is about 60:40. The enteric coated Compound I-1 was then encapsulated in an HPMC capsule.

This capsule formulation was also tested for stability and dissolution. It was found that after storing at 40° C. for 1 month at 75% RH, the formulation showed no deterioration of the amount of Compound I-1, no increase in the amount of Compound I-1 related impurities, and no change of amorphous Compound I-1 into a crystalline form, although water content of the formulation was slightly increased. Thus, Formulation B is also storage stable.

An in vitro dissolution test was carried out for Formulation B following Dissolution Study Procedure A. The results showed that after 2 hours in 0.1 N HCl solution, all capsules were partially disintegrated or swollen. And after placing the capsules in dissolution media with pH adjusted to 7.4 with $Na_3PO_4$ buffer, for all tested capsules, essentially all Compound I-1 was released within 2 hours, and for some capsules, essentially all Compound I-1 was released within 1 hour. Substantially similar results were obtained when Formulation B was tested around the time it was prepared or after storage at 40° C. for 1 month at 75% RH. Thus, Formulation B can also delay release of Compound I-1 until it reaches a non-acidic environment, which can then quickly release substantially all Compound I-1. Accordingly, Formulation B can also be especially suited for treating diseases such as inflammatory bowel diseases described herein, where delivery of active ingredients such as Compound I-1 to lower gastrointestinal tract or colon is desired.

Formulation Example 3. Formulation C, Granulated API in Capsule

Amorphous Compound I-1 was used for different formulations in this example.

In Formulation C, amorphous Compound I-1 was first mixed with Eudragit S 100 (Methacrylic acid copolymer), and Pharmacoat Hypromellose 606 (HPMC). This mixture was then subject to a fluid bed granulation process with top spray nozzles using ethanol as the granulating liquid. In one example, the fluidized bed granulation parameters were set as follows: inlet air temperature of 60-72° C.; outlet temperature of about 38-42° C.; product temperature of about 38-42° C.; dew point of about 10-20° C.; Air volume of about 50-150 $m^3/h$; atomizing pressure of 1.8-2.2 bar; and filter bags shaking of about 10 second shaking/60 seconds non shaking, GPCG mode. After all ethanol were sprayed, the air volume was lowered to 50 $m^3/h$ and the wet granulation was dried to a product temperature of about 38-42° C. In one example, the dried granules were screened using the Quadro Comil Model 197 Unit, equipped with round impeller, grated round 1016 micrometer screen, 0.05 inch+0.1 inch spacers, for a total of 0.15 inch, speed 450 rpm. After which, the granules were mixed with magnesium stearate and in some examples, also manually screened with a 600 micron sieve, and then encapsulated in an HPMC capsule. The weight percentages (exclusive of the HPMC capsule) are the following: Compound 1, about 75%; Eudragit S 100, about 20%; Pharmacoat Hypromellose 606 (about 4%); and magnesium stearate (about 1%).

This capsule formulation was also tested for stability and dissolution. It was found that after storing at 40° C. for 6 month at 75% RH, the formulation was storage stable, with no deterioration of the amount of Compound I-1, no increase in the amount of Compound I-1 related impurities, and no change of amorphous Compound I-1 into a crystalline form, although water content of the formulation was slightly increased.

An in vitro dissolution test was carried out for Formulation C following Dissolution Study Procedure A. The results showed that after 2 hours in 0.1 N HCl solution, all tested capsules, except one, were partially disintegrated. And after placing the capsules in dissolution media with pH adjusted to 7.4 with $Na_3PO_4$ buffer, for all tested capsules, essentially all Compound I-1 was released within 1 hour. Substantially similar results were obtained when Formulation C was tested around the time it was prepared or after storage at 40° C. for 1 month at 75% RH. Thus, Formulation C can also delay release of Compound I-1 until it reaches a non-acidic environment, which can then quickly release substantially all Compound I-1. Accordingly, Formulation C can also be especially suited for treating diseases such as inflammatory bowel diseases described herein, where delivery of active ingredients such as Compound I-1 to lower gastrointestinal tract or colon is desired.

Formulation Example 4. Formulation D, Direct Compression Tablets with Enteric Coating Amorphous Compound I-1 was used for different formulations in this example.

In Formulation D, a direct compress tablet with enteric coating was prepared using a mixture of amorphous Compound I-1, Eudragit S 100 (Methacrylic acid-methylmethacrylate 1:2 copolymer), silicified microcrystalline cellulose, and magnesium stearate. The weight percentages of the tablet are the following: Compound 1, about 40%; Eudragit S 100, about 20%; silicified microcrystalline cellulose, about 39%; and magnesium stearate, about 1%.

This tablet formulation was also tested for stability and dissolution. It was found that after storing at 40° C. for 1 month at 75% RH, the formulation was stable, with no deterioration of the amount of Compound I-1, no increase in the amount of Compound I-1 related impurities, and no change of amorphous Compound I-1 into a crystalline form, although water content of the formulation was slightly increased.

Similarly, an in vitro dissolution test was carried out for Formulation D following Dissolution Study Procedure A. The results showed that after 2 hours in 0.1 N HCl solution, all tablets were partially disintegrated. And after placing the tablets in dissolution media with pH adjusted to 7.4 with $Na_3PO_4$ buffer, about 40-65% of Compound I-1 was released at 1 hour; about 80-100% of Compound I-1 was released at 2 hours, and essentially all Compound I-1 was released within 4 hours. Substantially similar results were obtained when Formulation D was tested around the time it was prepared or after storage at 40° C. for 1 month at 75% RH. Thus, Formulation D shares similar delayed release characteristics as those of Formulations A-C. Accordingly, Formulation D is also well-suited for treating diseases such as inflammatory bowel diseases described herein, where delivery of active ingredients such as Compound I-1 to lower gastrointestinal tract or colon is desired.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. A compound having Compound I-1 in an amorphous form, Form A or Form E:

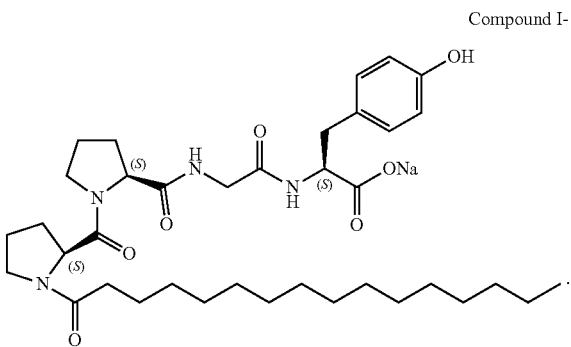

Compound I-1

2. The compound of claim 1, wherein the compound the compound I-1 in an amorphous form.

Figure 3:
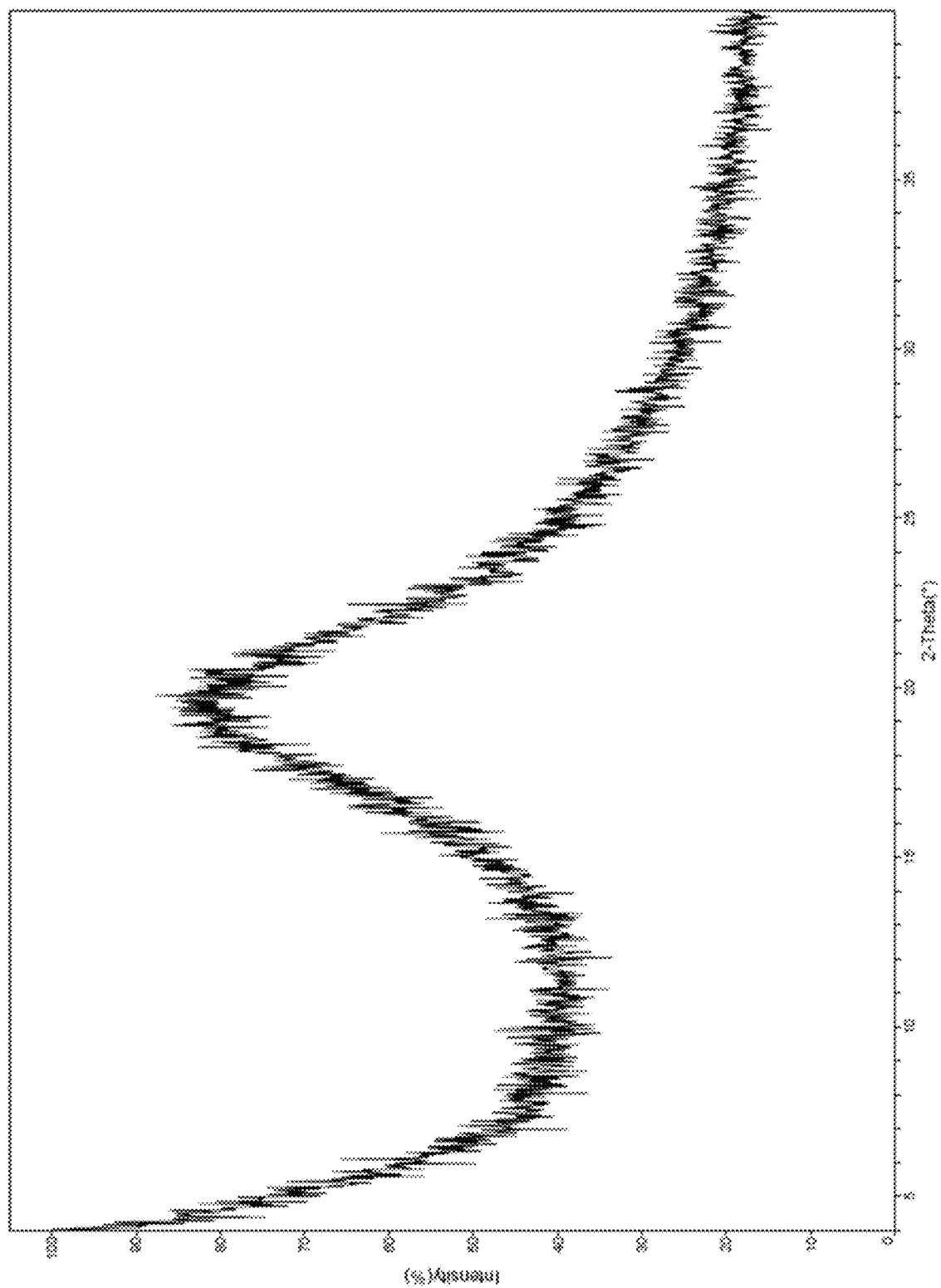

3. The compound of claim 2, wherein the compound I-1 in an amorphous form has an X-ray powder diffraction (XRPD) pattern substantially the same as shown in FIG. 3.

4. A pharmaceutical composition comprising the compound I-1 in an amorphous form,

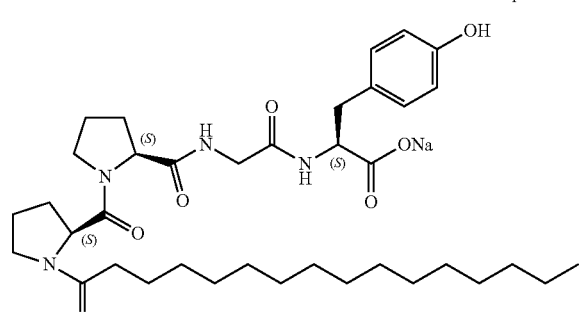

Compound I-1 wherein upon storage at 40° C. at a relative humidity of 75% or at 25° C. at a relative humidity of 60% for 6 month, the pharmaceutical composition is substantially free of the compound I-1 in a crystalline form.

5. The pharmaceutical composition of claim 4, wherein upon storage at 40° C. at a relative humidity of 75% for 6 month, the pharmaceutical composition is characterized by an X-ray powder diffraction (XRPD) pattern substantially the same as shown in FIG. 12, at the respective time point.

* * * * *